US008680020B2

(12) United States Patent
Wong et al.

(10) Patent No.: US 8,680,020 B2
(45) Date of Patent: Mar. 25, 2014

(54) GLYCAN ARRAYS ON PTFE-LIKE ALUMINUM COATED GLASS SLIDES AND RELATED METHODS

(75) Inventors: Chi-Huey Wong, La Jolla, CA (US); Chung-Yi Wu, Taipei (TW); Susan Y. Tseng, Taipei (TW)

(73) Assignee: Academia Sinica, Taipei (TW)

( * ) Notice: Subject to any disclaimer, the term of this patent is extended or adjusted under 35 U.S.C. 154(b) by 306 days.

(21) Appl. No.: 12/503,797

(22) Filed: Jul. 15, 2009

(65) Prior Publication Data
US 2010/0016171 A1   Jan. 21, 2010

Related U.S. Application Data

(60) Provisional application No. 61/080,931, filed on Jul. 15, 2008, provisional application No. 61/107,624, filed on Oct. 22, 2008.

(51) Int. Cl.
*C40B 40/12* (2006.01)
*C40B 20/04* (2006.01)

(52) U.S. Cl.
USPC ............. 506/19; 506/13; 506/42; 530/350

(58) Field of Classification Search
USPC ................................ 506/13, 19, 42
See application file for complete search history.

(56) References Cited

U.S. PATENT DOCUMENTS

| 7,019,288 | B2 * | 3/2006 | Becker | 250/288 |
| 2004/0086423 | A1 | 5/2004 | Wohlstadter | |
| 2005/0255491 | A1 | 11/2005 | Lee | |
| 2006/0286140 | A1 * | 12/2006 | Wickstrom et al. | 424/423 |
| 2007/0065949 | A1 | 3/2007 | Hutchens | |
| 2007/0213278 | A1 * | 9/2007 | Wong et al. | 514/23 |
| 2008/0070324 | A1 | 3/2008 | Floyd | |
| 2009/0035179 | A1 * | 2/2009 | Rakow et al. | 422/55 |
| 2010/0047828 | A1 * | 2/2010 | Sorensen et al. | 435/7.72 |
| 2010/0112195 | A1 * | 5/2010 | Kodas et al. | 427/98.4 |
| 2011/0124116 | A1 * | 5/2011 | Wohlstadter et al. | 436/172 |
| 2011/0237459 | A1 * | 9/2011 | Nova et al. | 506/9 |

OTHER PUBLICATIONS

Patent Cooper Ation Treaty, International Search Report; PCT/US2009/050754.

* cited by examiner

*Primary Examiner* — Teresa Wessendorf
(74) *Attorney, Agent, or Firm* — Shantanu Basu; Eckman Basu LLP

(57) ABSTRACT

Aluminum coated glass slides provide a novel glycan array platform. Specifically, aluminum coated glass slides increase sensitivity of fluorescent based assay methods. Additionally, aluminum coated glass slides allows for mass spectroscopic analysis of carbohydrates and provide a platform for examining activity of cellulases. The unique properties of ACG slides include: 1) the metal oxide layer on the surface can be activated for grafting organic compounds such as modified oligosaccharides; 2) the surface remains electrically conductive, and the grafted oligosaccharides can be simultaneously characterized by mass spectrometry and carbohydrate-binding assay; and 3) the slides are more sensitive than transparent glass slides in binding analysis.

24 Claims, 34 Drawing Sheets

US 8,680,020 B2

SEQUENCE LISTING

```
<160> NUMBER OF SEQ ID NOS: 8

<210> SEQ ID NO 1
<211> LENGTH: 31
<212> TYPE: DNA
```

-continued

```
<213> ORGANISM: Artificial Sequence
<220> FEATURE:
<223> OTHER INFORMATION: Primer

<400> SEQUENCE: 1
ggaattccat atggcaacag taaagttcaa g                                          31

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
cgggatccct tcttttgctt ctctaacatt tg                                         32

<210> SEQ ID NO 3
<211> LENGTH: 48
<212> TYPE: DNA
<213> ORGANISM: Artificial Sequence
<220> FEATURE:
<223> OTHER INFORMATION: Linker

<400> SEQUENCE: 3
gatctgatct gtacgacgat gacgataagg gatctatcga aggtcgtg                        48

<210> SEQ ID NO 4
<211> LENGTH: 48
<212> TYPE: DNA
<213> ORGANISM: Artificial Sequence
<220> FEATURE:
<223> OTHER INFORMATION: Linker

<400> SEQUENCE: 4
gatccacgac cttcgataga tcccttatcg tcatcgtcgt acagatca                        48

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
gaagatctat acttccgcag cctgatg                                               27

<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6
acgcgtcgac ttaggtttca ctgtctgtgt actg                                       34

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
gaagatctga acctgcaaaa gtggttgac                                             29
```

```
<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
acgcgtcgac ttagggctcc gcagcttcaa gcac                              34
```

GLYCAN ARRAYS ON PTFE-LIKE ALUMINUM COATED GLASS SLIDES AND RELATED METHODS

RELATED APPLICATION

This application claims the benefit of and priority to U.S. Provisional Application Ser. No. 61/080,931, filed Jul. 15, 2008 and U.S. Provisional Application Ser. No. 61/107,624, filed Oct. 22, 2008, the contents of which are incorporated by reference herein in their entirety.

BACKGROUND

Glycan arrays on novel aluminum coated glass slides, including poly-fluorophosphonated aluminum coated glass slides, allow characterization by mass spectrometry without matrix, fluorescence assessment of sugar-protein binding, and identification and study of enzymes with different efficiency and specificity.

Based on the SWISS-PROT protein database, more than 50% of human proteins are predicted to be glycosylated. Carbohydrates often exist on cell surfaces as glycoprotein or glycolipid conjugates and play important structural and functional roles in numerous biological recognition processes, for example, protein folding, secretion and stabilization, viral and bacterial infection, cancer metastasis, inflammatory response, innate and adaptive immunity, and many other receptor mediated signaling processes. Moreover, there exist many examples in which glycosylation is required for biological activities. Furthermore, many organisms such as sessile plants have evolved specific glycosylation mechanisms to detoxify harmful exogenous xenobiotics.

Despite the increasing awareness of the biological significance of carbohydrates, the study of carbohydrate-protein interactions still encounters much difficulty, largely because of the structure complexity and synthetic difficulty of carbohydrates and the low affinity of their interactions with glycan-binding proteins (GBPs). Typically the monomeric dissociation constant ($K_D$) in a carbohydrate-protein interaction is in the millimolar range; thus, carbohydrate-mediated biological responses are often through multivalent interaction on the cell surface in order to achieve high affinity and specificity.

A major challenge in cell biology is to define the interaction of oligosaccharides and proteins involved in many biological processes. However, pure oligosaccharides are difficult to obtain and there is a need for development of highly sensitive and high-throughput methods for identification and binding study of carbohydrates recognized by various receptors.

Carbohydrate microarrays are a powerful tool for the study of glycobiology and the high-throughput bioassay of epidemic diseases. A fundamental problem of this technology is how to characterize and quantify the oligosaccharides that are covalently bound to the surface. Effective immobilization of sugars on the surface is essential for surviving consecutive substrate washing when evaluating sugar-protein binding. Mass spectrometry (MS) has been reported to be a useful analytical method for the high-throughput characterization of immobilized sugars on porous glass slides.

Although a variety of substrates are commercially available for glycan arrays, they are not suitable for direct mass spectrometric analysis. These substrates include glass and polyethylene terephthalate (PET) coated with amine, carboxylate, N-hydroxysuccinimide (NHS), avidin, epoxy, aldehyde, chelating nickel groups, and so on. In fact, NHS-functionalized glass slides are commonly used for the preparation of glycan arrays. A typical example is that of sugar antigens immobilized on the surface of the glass slide, after which a sugar-binding monoclonal antibody and a fluorescence-tagged secondary antibody were incubated for studies of protein-carbohydrate interaction. Although effective, these glass slides are not ideal for use to characterize the bound sugars by mass spectrometry.

Substrates selected for matrix-assisted laser desorption-ionization time-of-flight (MALDI-TOF) MS should be conductive or semiconductive so that a uniform electric field can be produced under high vacuum. Standard stainless-steel plates are usually the choice for loading the analytes.

In MALDI MS, the energy of the pulse laser beam is absorbed by the matrix (miscible organic chemicals) to prevent sample fragmentation. MALDI-TOF MS is an excellent tool for analyzing high-molecular-weight biomolecules. However, the chemicals in the organic matrix interfere with low-molecular-weight oli-gosaccharides (typically less than 2000 Da); thus, porous silicon was chosen as the substrate for analyzing biomolecules by MS without the addition of matrix chemicals. In desorption-ionization on silicon (DIOS) MS, biomolecules of relatively low molecular weight were identified on the basis of the m/z ratio of the pseudoparent peak from MS.

SUMMARY

According to a feature of the present disclosure, an array of carbohydrates immobilized on an aluminum-coated transparent solid substrate or a PTFE-like aluminum-coated transparent solid substrate is disclosed. The array comprises a plurality of carbohydrates immobilized at discrete locations on a surface of an aluminum-coated transparent solid substrate, wherein the array is suitable for (a) performing mass spectroscopic characterization of the immobilized carbohydrates, and (b) performing analysis of binding reactions between the carbohydrates and molecules suspected of specifically binding the carbohydrates.

According to features of the present disclosure, the substrate may be conductive or semiconductive of an electrical field.

According to a feature of the present disclosure, the transparent solid substrate may be glass.

According to a feature of the present disclosure, the carbohydrate may be a glycan.

According to a feature of the present disclosure, the carbohydrates may be immobilized by a non-covalent bond.

According to a feature of the present disclosure, the carbohydrates may be polyfluorinated with a —$C_nF_{2n+1}$ (n>=4) tail.

According to a feature of the present disclosure, the polyfluorinated carbohydrates may be spotted on the surface of the PTFE-like aluminum-coated transparent solid substrate.

According to a feature of the present disclosure, the carbohydrates may be immobilized by a covalent bond.

According to a feature of the present disclosure, the carbohydrates may be modified with a phosphonic acid functional group.

According to a feature of the present disclosure, the phosphonylated carbohydrates may be immobilized on the surface of the substrate by a chelating interaction between the phosphonic acid group and the aluminum oxide on the surface of the aluminum-coated transparent solid substrate.

According to a feature of the present disclosure, the carbohydrates may be modified with a photocleavable linker and a silane functional group.

According to a feature of the present disclosure, the photocleavable linker has the general formula:

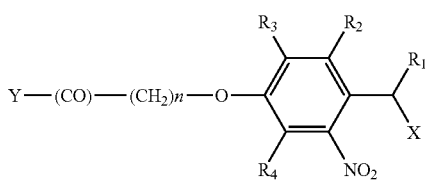

in which $R^1$ is hydrogen, $C_1$-$C_8$ alkyl; $R^2$ and $R^4$ are each independently hydrogen, C1-C8 alkoxy; $R^3$ is $C^1C^8$ alkoxy; X is O(CO)N—$(CH_2)$n-$R^5$, in which n>=3, $R^5$ is carbohydrates, Y is the solid support, like ACG slide.

According to a feature of the present disclosure, the mass spectroscopic characterization of the immobilized carbohydrates comprises a time-of-flight mass spectrometry (MS-TOF).

According to a feature of the present disclosure, the mass spectroscopic characterization of the immobilized carbohydrates comprises a matrix-assisted laser desorption-ionization time-of-flight (MALDI-TOF) mass spectrometry.

According to a feature of the present disclosure, the carbohydrates are polysaccharides, or oligosaccharides, or carbohydrate portions of a glycoconjugate, or cellobiose, or cellotriose, or cellotetraose, or GloboH, or Gb5.

According to a feature of the present disclosure, the mass spectroscopic characterization of the immobilized carbohydrates comprises characterization of the carbohydrate products of a cellulase enzyme reaction.

According to a feature of the present disclosure, the cellulase enzyme reaction is performed on immobilized carbohydrates on the array surface, wherein the cellulase enzyme is suspected of being capable of degrading the immobilized polysaccharides, or oligosaccharides, or carbohydrate portions of a glycoconjugate, or cellobiose, or cellotriose, or cellotetraose, or GloboH, or Gb5.

According to a feature of the present disclosure, the MS-TOF characterization can be performed without adding matrix.

According to a feature of the present disclosure, a carbohydrate binding assay can be performed on the array about 15 minutes following an MS-TOF characterization.

According to a feature of the present disclosure, the molecules suspected of specifically binding the carbohydrates are proteins.

According to a feature of the present disclosure, the proteins are cellulases.

According to a feature of the present disclosure, the cellulases are selected from the group consisting of 1,4-β-glucosidases, exoglucanases (1,4-β-D glucan cellobiohydrolases) and endoglucanases (1,4-β-D glucan glucanohydrolases).

According to a feature of the present disclosure, the proteins analyzed for binding to the carbohydrates immobilized on the array are labeled with a detectable label.

According to a feature of the present disclosure, the protein labels comprise fluorescent dyes.

According to a feature of the present disclosure, the fluorescent dyes comprise amine-reactive dyes.

According to a feature of the present disclosure, disclosed is a computer readable medium comprising data representing the characterization of immobilized carbohydrates on the surface of the array, or data representing the analysis of the carbohydrate binding reactions on the array surface, or both.

According to a feature of the present disclosure, a method for characterization of carbohydrates immobilized on a PTFE-like aluminum-coated transparent solid substrate is disclosed comprising:

(a) providing an array comprising a plurality of carbohydrates immobilized at discrete locations on a surface of a PTFE-like aluminum-coated transparent solid substrate; and (b) performing mass spectroscopic analysis to characterize the carbohydrates immobilized at each discrete location.

According to a feature of the present disclosure, the mass spectroscopic characterization of the immobilized carbohydrates comprises a time-of-flight mass spectrometry (MS-TOF).

According to a feature of the present disclosure, the method further comprises:

(c) performing a binding analysis of suspected carbohydrate binding moieties.

According to a feature of the present disclosure, the suspected carbohydrate binding moieties are cellulase proteins.

According to a feature of the present disclosure, the method further comprises:

(d) incubating the cellulase proteins with the bound carbohydrates immobilized on the array surface under conditions suitable for the cellulases to hydrolyze the carbohydrates.

According to a feature of the present disclosure, the method further comprises:

(e) characterizing the products of the cellulase proteins remaining immobilized on the array surface following hydrolysis by the cellulases.

According to a feature of the present disclosure, the cellulases are selected from the group consisting of 1,4-β-glucosidases, exoglucanases (1,4-β-D glucan cellobiohydrolases) and endoglucanases (1,4-β-D glucan glucanohydrolases).

According to a feature of the present disclosure, a method for analysis of binding reactions between the carbohydrates and molecules suspected of specifically binding the carbohydrates is disclosed comprising:

(a) providing an array comprising a plurality of carbohydrates immobilized at discrete locations on a surface of an aluminum-coated transparaent solid substrate or a PTFE-like aluminum-coated transparent solid substrate;

(b) contacting the array with one or more molecules suspected of binding to one or more of the plurality of carbohydrates immobilized on the array surface; and (c) identifying the presence or absence of binding reactions at one or more discrete locations on the array surface.

According to a feature of the present disclosure, the molecules suspected of specifically binding the carbohydrates are proteins labeled with a detectable label.

According to a feature of the present disclosure, the protein labels comprise fluorescent dyes.

According to a feature of the present disclosure, the fluorescent dyes comprise amine-reactive cyanine dyes.

According to a feature of the present disclosure, the binding of a molecule to a carbohydrate on the array is representative of a biological process.

According to a feature of the present disclosure, the biological process is selected from the group consisting of protein folding, protein secretion, protein stabilization, viral infection, bacterial infection, cancer metastasis, inflammatory response, innate immunity, adaptive immunity, a receptor-mediated signaling process, and biofuel production.

According to a feature of the present disclosure, the carbohydrates are polysaccharides, or oligosaccharides, or carbohydrate portions of a glycoconjugate, or cellobiose, or cellotriose, or cellotetraose, or GloboH, or Gb5.

According to a feature of the present disclosure, a mass spectroscopic characterization of the carbohydrates immobilized on the array is performed prior to the binding analysis.

According to a feature of the present disclosure, a mass spectroscopic characterization of the carbohydrates immobilized on the array is performed prior to and following the binding analysis, wherein the one or more molecules suspected of binding to one or more of the plurality of carbohydrates immobilized on the array surface comprises a cellulose protein enzyme capable of hydrolyzing one or more carbohydrates on the array, and wherein the binding reaction is performed under conditions suitable for the cellulose to hydrolyze the carbohydrate.

According to a feature of the present disclosure, the cellulases are selected from the group consisting of 1,4-β-glucosidases, exoglucanases (1,4-β-D glucan cellobiohydrolases) and endoglucanases (1,4-β-D glucan glucanohydrolases).

According to a feature of the present disclosure, a method for fabricating an array of carbohydrates immobilized on an aluminum coated transparaent solid substrate or a PTFE-like aluminum-coated transparent solid substrate is disclosed comprising: (a) immobilizing a plurality of carbohydrates at discrete locations on a surface of an aluminum coated transparaent solid substrate or a PTFE-like aluminum-coated transparent solid substrate, wherein the substrate is conductive or semiconductive of an electrical field, wherein the array is suitable for performing mass spectroscopic characterization of the immobilized carbohydrates, and wherein the array is suitable for performing analysis of binding reactions between the carbohydrates and molecules suspected of specifically binding the carbohydrates.

According to a feature of the present disclosure, the carbohydrates are immobilized by a non-covalent bond.

According to a feature of the present disclosure, the carbohydrates are polyfluorinated.

According to a feature of the present disclosure, the carbohydrates are immobilized by a covalent bond.

According to a feature of the present disclosure, the carbohydrates are modified with a phosphonic acid functional group.

According to a feature of the present disclosure, the method further comprises (b) performing a characterization of carbohydrates immobilized on the array surface by mass spectrometry, wherein observation of one or more of a high signal/noise (S/N) ratio, low laser fluence rate, or a low fragmentation of signal, in an absence of matrix material is indicative of the array being suitable for performing mass spectroscopic characterization of the immobilized carbohydrates.

According to a feature of the present disclosure, the method further comprises (c) performing a carbohydrate binding assay on the array by contacting the array with a carbohydrate-binding protein, wherein detection of specific binding at one or more discrete locations on the array is indicative of the array being suitable for performing analysis of binding reactions between the carbohydrates and molecules suspected of specifically binding the carbohydrates According to a feature of the present disclosure, the carbohydrate is selected from a sugar, or a glycoprotein, or a glycolipid, or mannose, each comprising internal or nonreducing terminal alpha-mannosyl groups and the binding molecule is Concanavalin A.

According to a feature of the present disclosure, an array for use in disease diagnosis and drug discovery is disclosed, wherein the array is fabricated by (a) immobilizing a plurality of carbohydrates at discrete locations on a surface of an aluminum coated transparent solid substrate or a PTFE-like aluminum-coated transparent solid substrate, wherein the substrate is conductive or semiconductive of an electrical field, wherein the array is suitable for performing mass spectroscopic characterization of the immobilized carbohydrates, and wherein the array is suitable for performing analysis of binding reactions between the carbohydrates and molecules suspected of specifically binding the carbohydrates..

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Figure 1:
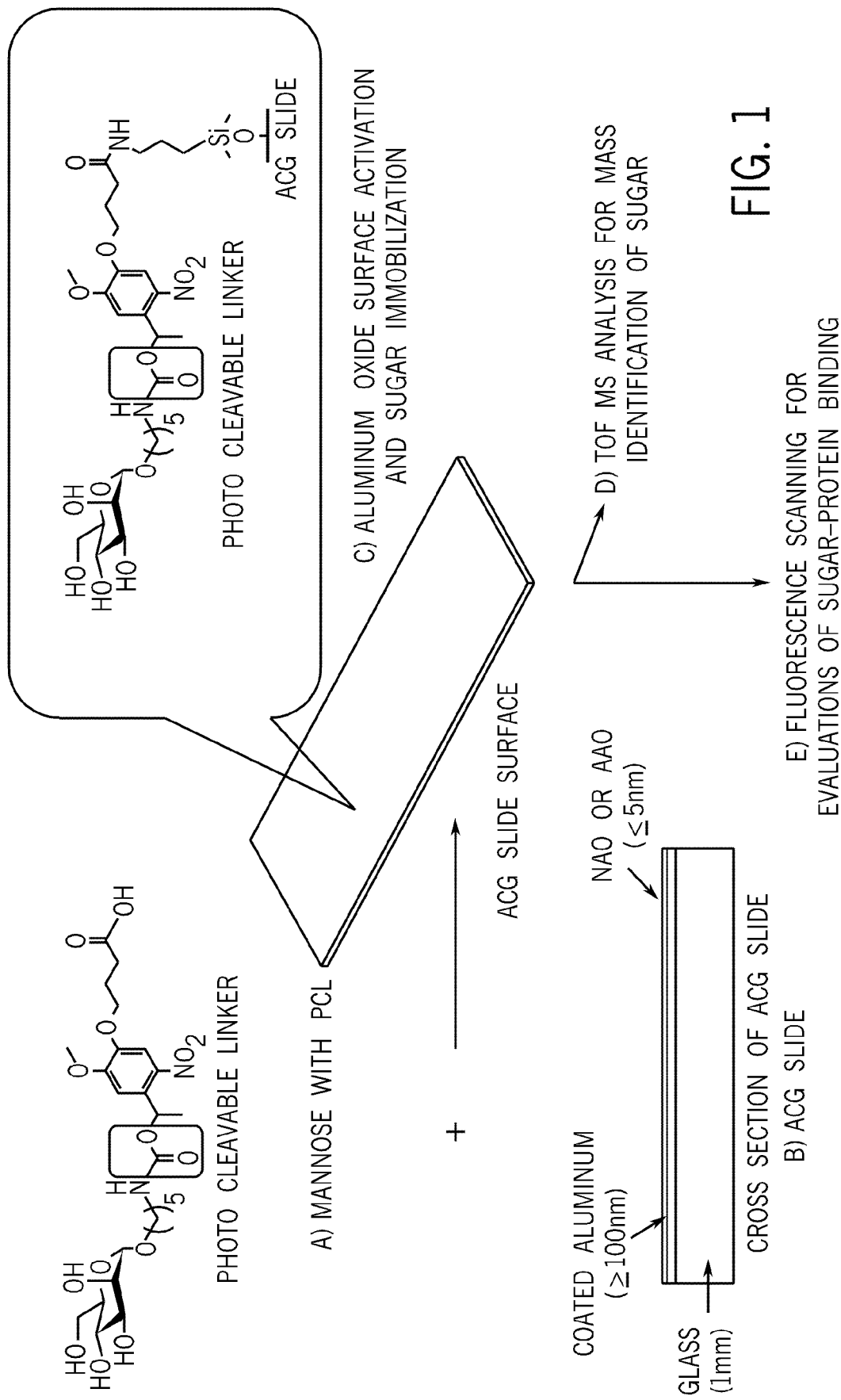
FIG. 1 is a block diagram of implementations and experimental aluminum coated glass (ACG) slide and related experimental techniques.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

This disclosure incorporates by reference U.S. Patent Publication No. 2007/0213278, filed Dec. 22, 2006.

As used herein, the term Teflon or PTFE refers to polytetrafluoroethylene.

Effective adhesion between sugar molecules and the substrate surfaces have been achieved through covalent bonding. Physical adsorption of sugar derivatives on fluorous surfaces may also be feasible for sufficient adhesion. Porous silicon plates also acted as a matrix in DIOS MS, and mass spectra were obtained with a high signal-to-noise (S/N) ratio without fragmentation. The preparation of porous silicon plates requires the usage of corrosive acid, which is not environmentally friendly, and the quality of the plates is difficult to control. On the other hand, porous aluminum oxide exists naturally on the surface of aluminum; the electrochemical anodization of aluminum-coated glass (ACG) slides can be carried out in mildly acidic aqueous solution. Silylation reactions on silicon surfaces can also be used on aluminum surfaces under proper conditions. The freshly cut surface of plate aluminum has a shiny metallic texture. When exposed to air, the surface gradually oxidizes and turns opaque as a layer of aluminum oxide (called native oxide) is formed. Native aluminum oxide (NAO) grown on aluminum surfaces has no orientation compared to that of anodized aluminum oxide (AAO). The thickness of NAO on aluminum surfaces is just a few nanometers. In contrast, the thickness of AAO could grow quickly (within 15-20 min) to the micrometer range with the growing direction aligned to an applied electric field. In a few trial experiments, pure aluminum plates were fabricated (with a thickness of 1 mm) and the AAO layer was grown to 2 mm on the surface of the plate. This surface with a thick layer of AAO became nonconductive (like ceramics) and was not suitable for our study. However, in all cases, the amorphous oxide layers on the aluminum surfaces could be modified chemically, and the substrate remained electrically conductive only when the thickness of the oxide layer on the surface was in the nanometer range.

According to implementations illustrated in FIG. 1, several new substrates with a thin layer of aluminum oxide on the surface of ACG slides were fabricated in an attempt to characterize the molecular weight of the surface-grafted oligosaccharide and simultaneously to look for its sugar-protein binding capability. Designed mannose and lactose derivatives with a built-in photocleavable linker (PCL) were synthesized and covalently bound to the activated ACG slides, as illustrated according to implementations shown in FIG. 2. Without addition of a miscible organic matrix, the sugar-immobilized ACG slides were subjected to molecular-weight identification and protein-binding evaluation.

Cellulases are of current interest because of their application to biofuel production. Cellobiose or cellotriose with fluorogenic or chromogenic groups are commonly used as substrates for the investigation of cellulase activity and specificity. However, during enzymatic hydrolysis, the fluorogenic or chromogenic leaving group generated in the reaction showed signal only at high pH, but, cellulases exhibit their optimum activity at low pH (4-6). Poly-fluorinated cellobiose was immobilized non-covalently on the PTFE-like ACG slides, and conducted the enzymatic hydrolysis at pH 4-6 in situ. The hydrolyzed products remaining on the slide surface were then identified by MS-TOF.

Moreover, the recently developed aluminum coated glass (ACG) slides were oxidized and reacted with a functionalized alkyl monoethoxysilane to form a covalent handle, followed by coupling with a glycan containing the photo-cleavable linker. This glycan array with a photo-cleavable linker on the ACG slide surfaces can be characterized by time-of-flight mass spectrometry (MS-TOF) without matrix, and used for binding evaluation of fluorescence-tagged proteins. The fluorescence intensity of sugar-protein complex on ACG-slide is higher than on glass slides. A new method is therefore disclosed for fabricating stable poly-fluorinated (also called the PTFE-like) ACG slides, and the use of these slides for non-covalent arraying glycans as substrates for the study of cellulase activities by using mass spectrometry as a detector. Moreover, by using the property of phosphonic acid to chelate with the aluminum oxide surface easily, the carbohydrate with a phosphonic acid linker was used to create covalent bonding glycan array.

According to implementations, a new generation of carbohydrate array on PTFE-like ACG slides have has been developed for immobilizing sugars. Mannose and lactose with a built-in photocleavable linker immobilized on the ACG slide surfaces were subjected to MALDI MS analysis to characterize the molecular weight of the immobilized sugars. A proportional correlation was observed between the quantity of mannose (m/z) and the fluorescence intensity of its protein binding. In protein-binding assays of mannose-ACG and Globo H-ACG slides, higher fluorescence intensity and sensitivity was observed than with glass slides, perhaps due to the material properties, surface morphologies, and binding-site architectures between proteins and the immobilized sugars on the slide surfaces.

With mass spectrometry, this glycan array can be used as an effective analytical tool to identify and differentiate various types of cellulases and their efficiency. The unique properties of aluminum oxide coated glass slides make it possible to conveniently and non-covalently or covalently array glycans via phosphonate chemistry and the glycan array can be characterized with MS spectrometry without the use of matrix.

According to implementations, FIG. 1 illustrates a novel experimental ACG slide and related methods for experimentation thereon. In a), a sugar derivative such as mannose with a built-in photocleavable linker is created, according to implementations. In b) ACG slide (75.5×25.4×1 mm$^3$) with layers of aluminum oxide (<5 nm) on the surface and pure aluminum (>100 nm) coated on the glass slide (1 mm) is shown. In c) the ACG slide was optionally activated, and the sugar derivatives were immobilized (microarrayed and manually spotted) on the surface. The slide was subjected to molecular-weight identification of the sugar by mass spectrometry in d) or further evaluated for its sugar-protein binding by a fluorescence scanner in e).

Figure 2:
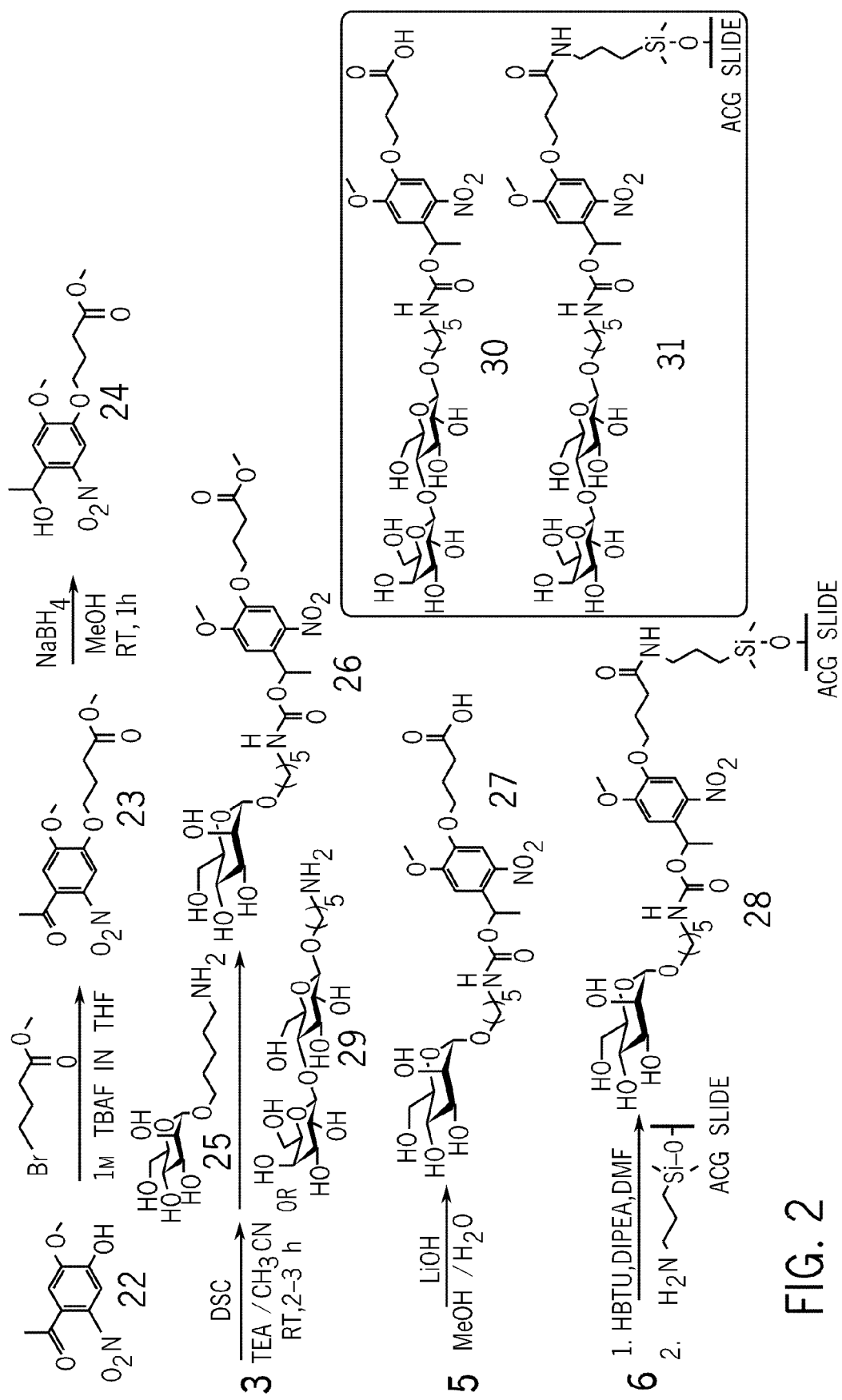
FIG. 2 is a scheme showing an implementation of the synthesis of mannose-ACG and lactose-ACG with a photocleavable linker.

According to implementations and as illustrated in FIG. 2, a scheme is shown the synthesis of mannose-ACG and lactose-ACG with a photocleavable linker; DIPEA=N,N-diisopropylethylamine, DSC=N,N'-disuccinimidyl carbonate, HBTU=2-(1-benzotriazol-1-yl)-1,1,3,3-tetramethyluronium hexafluorophosphate (TBAF=tetra-n-butylammonium fluoride, TEA=triethylamine).

Figure 15:
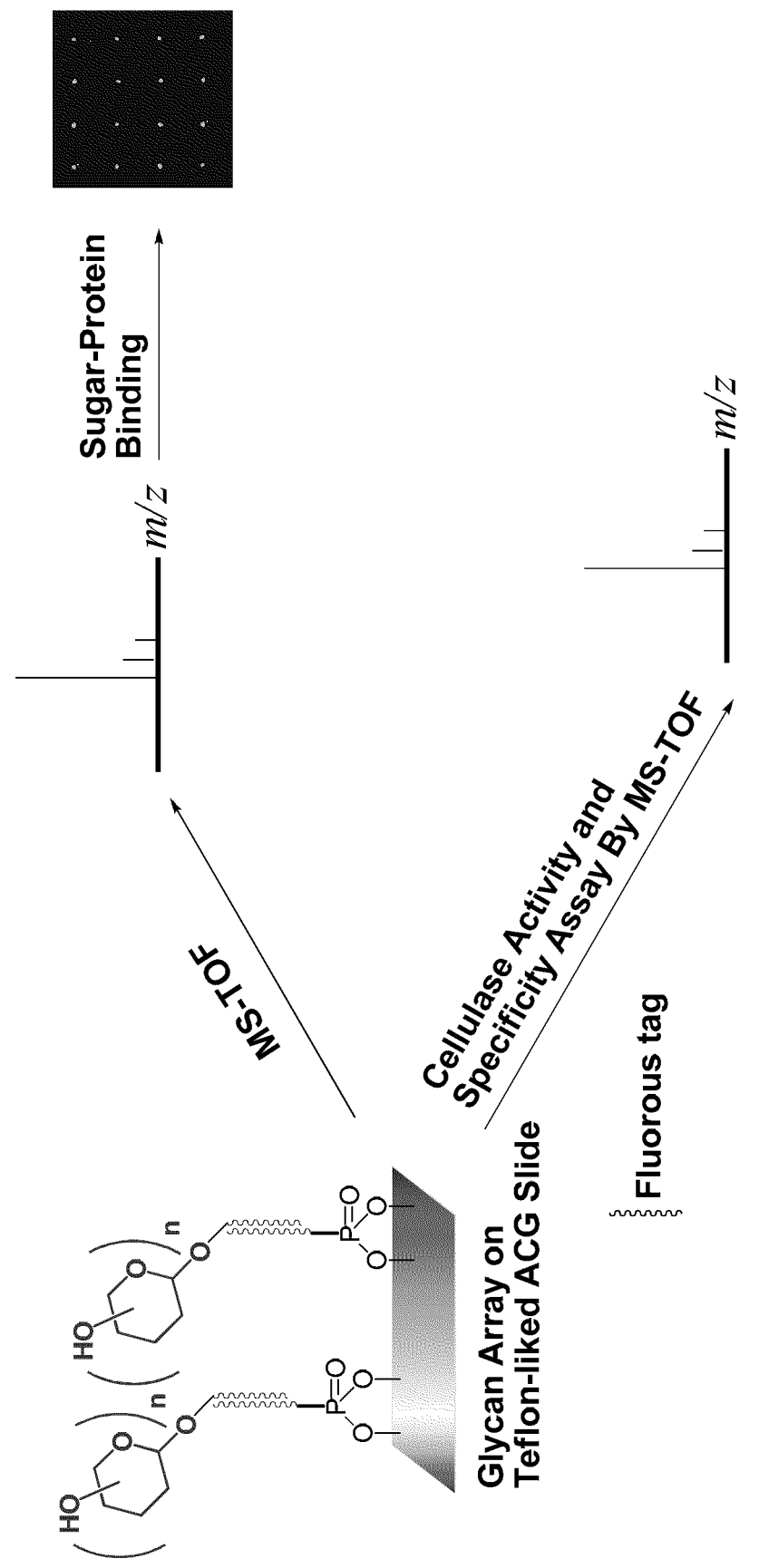
FIG. 15 is a block diagram of an implementation of the creation of non-covalent bond glycan array on the PTFE-like ACG slide.

According to implementations and as illustrated in FIG. 15, a block diagram of an implementation of the creation of non-covalent bond glycan array on the PTFE-like ACG slide is shown. According to the implementation, sugars are reversibly bonded via a poly-flourinated tail to an ACG slide. Various mass spectroscopy experiments are then performed. For example, MS-TOF is performed in a sugar-binding assay, or cellulase activity and specificity assay by MS-TOF may be performed.

Artisans will readily appreciate both the utility of the apparatuses disclosed herein, as well as the various experimental methods based on the Examples and other disclosure provided here. Such devices and methods are expressly contemplated in this disclosure.

EXAMPLES

Example 1

Surface Properties of ACG Slides

Figure 3:
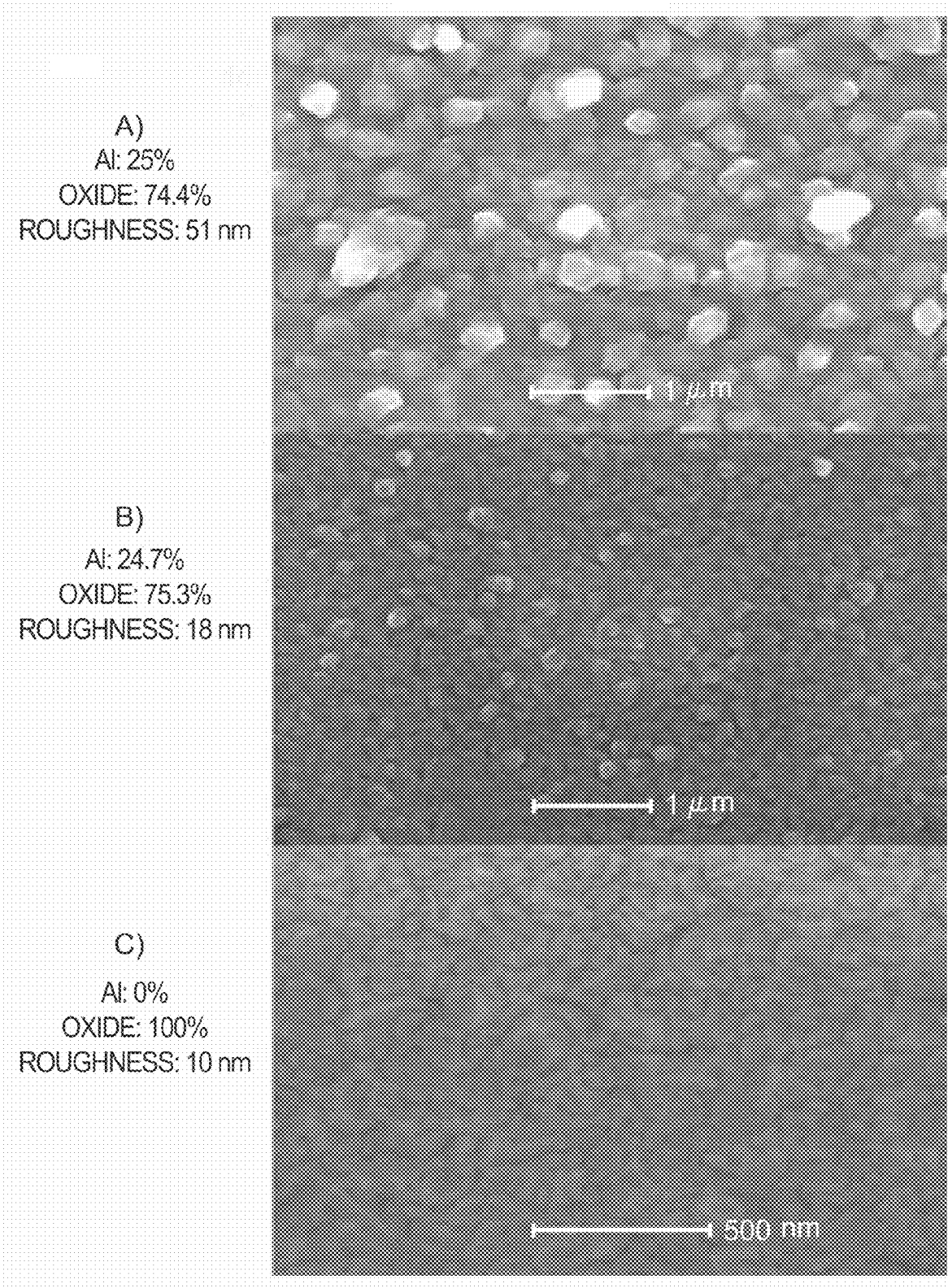
FIG. 3 are microscopy photographs of implementations of aluminum coated glass slides.

A layer of pure aluminum (99.999%) at least 100 nm thick was coated onto the micro glass slides by using various coating techniques, such as magnetron sputtering, cathode arc evaporation, and thermal coating. These slides were either used without further manipulation or electrically anodized before usage. According to implementations, FIG. 3 shows their surface morphology, composition, and roughness as determined by scanning electron microscopy (SEM), atomic force microscopy (AFM), and X-ray photoelectron spectroscopy (XPS) of an ACG slide. FIG. 3A shows aluminum deposited by cathode arc evaporation, FIG. 3B shows an aluminum coating deposited by magnetron sputtering, and FIG. 3C shows aluminum AAO/ACG slide obtained by thermal coating followed by electrochemical surface anodization.

As can be seen, the ACG slide produced by cathode arc evaporation has a coating of large granules and a high surface roughness. Slides with high surface roughness affect the surface-wetting property. The magnetron-sputtered ACG slide gave an acceptable surface roughness; however, it required a long coating time to achieve the desired coating thickness and was used only at the early stages of this study. Thermal coated ACG slides achieved the desired coating thickness in a relatively short time. It gave the smoothest surface with a surface roughness of 10 nm. With subsequent surface-anodization treatment, the ACG slide provided a stable surface for grafting. Only the anodized slide surfaces were covered with 100% aluminum oxide, as shown in FIG. 4.

Figure 4:
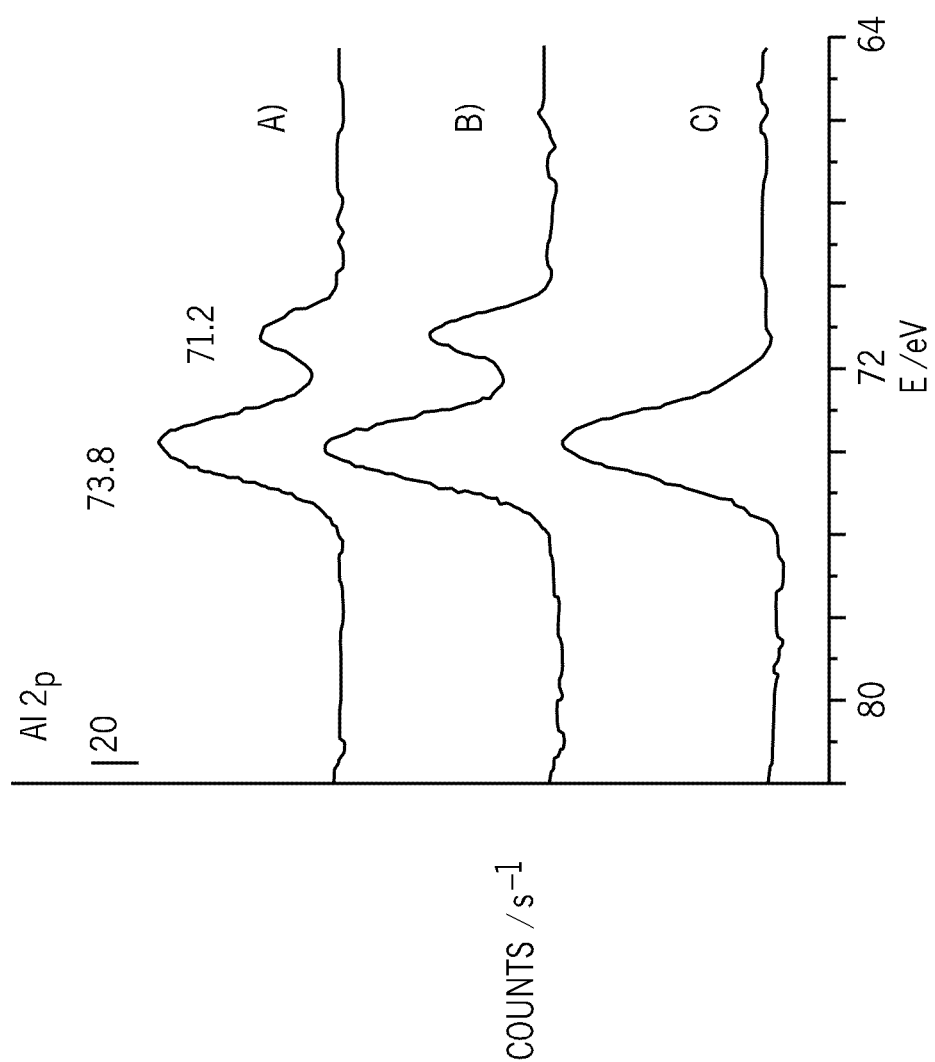
FIG. 4 are graphs of experimental data illustrating the surface composition of ACG slides made by various methods.

According to implementations of experimental data shown in FIG. 4, XPS spectra of the surface composition of a) an NAO/ACG slide obtained by cathode arc evaporation, b) an NAO/ACG slide obtained by magnetron sputtering, and c) an AAO/ACG slide obtained by thermal coating followed by surface anodization are shown. The binding energy for C(1 s) at 284.5 eV and O(1 s) at 531 eV were used to calibrate the binding energy of these spectra. The electrical resistance of the ACG slide (end-to-end distance) was measured between 1.6 and 4 Ω. These slides became electrically nonconductive when the oxide layer grew thick. The depth of penetration for XPS was 20-50 Å, and the thickness of the oxide layer (either NAO or AAO) in this study was estimated from the cross-section to be no more than 5 nm.

The thickness of coated aluminum on the glass slide needs to be >100 nm so that the substrate remains non-transparent within the visible region. When a transparent substrate was used, part of the fluorescent light passed through the substance, and the scanner detected only a portion of the Cy3 fluorescence. The instrument detected more fluorescent light when a nontransparent ACG slide was used as the background substrate.

Figure 5A:
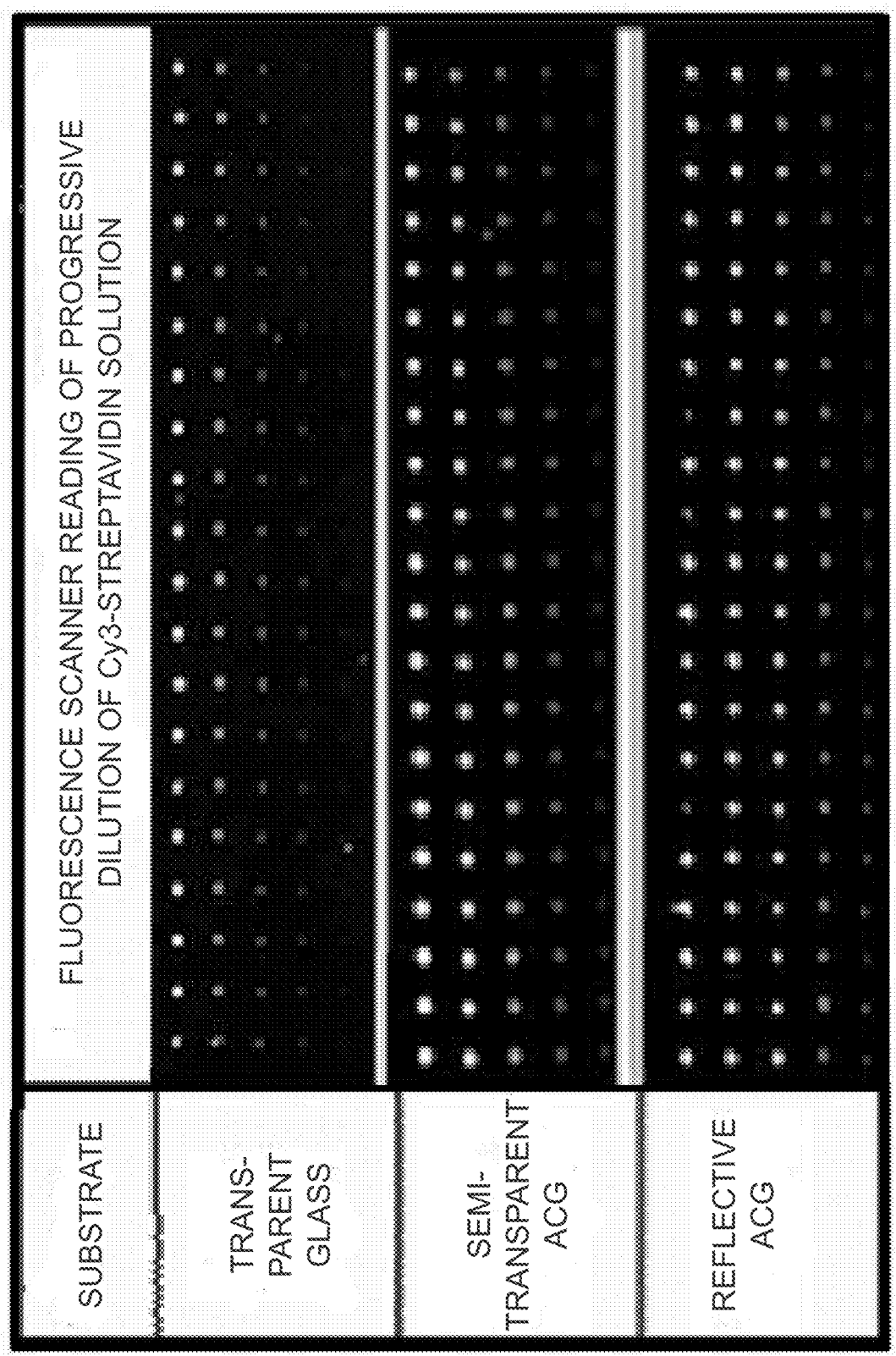
FIG. 5 are visual representations of implementations of the optical properties of the micro glass slide, the semitransparent ACG slide, and the totally reflective (nontransparent) ACG slide.
Figure 5B:
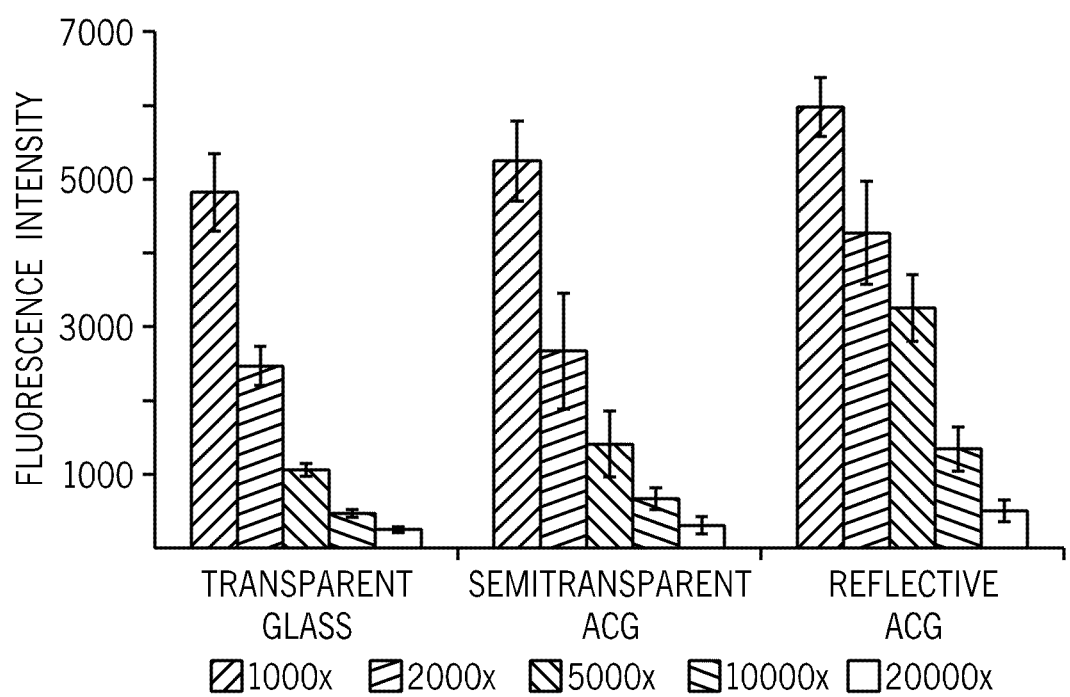

FIG. 5 shows data the optical properties of ACG slides compared to those of the micro glass slide. The thickness of the coated aluminum on the semitransparent ACG slides was just a few nanometers, and that of the reflective ACG slides was approximately 300 nm. FIG. 5 shows the optical properties of the micro glass slide, the semitransparent ACG slide, and the totally reflective (nontransparent) ACG slide. In FIG. 5A, a series of Cy3-streptavidin solutions of 1 mg/mL diluted 1000×, 2000×, 5000×, 10000×, and 20000× was spotted on each of these slides, air-dried, and analyzed with an array-WoRx fluorescence spectrometer. A light source of wavelength 540 nm was provided by the instrument. Fluorescence of wavelength 595 nm was emitted from the slide surface and detected by the detector. The scanner detected the fluorescence only up to 5000× dilution for the transparent micro glass slide, but up to 10000× and 20000× times dilution, respectively, for the semitransparent ACG slide and the totally reflective ACG slide, in which the thickness of the coated aluminum varied from a few nanometers in the former to greater than 100 nm in the latter. FIG. 5B shows implementations of experimental data wherein the actual calculated fluorescence intensity for each substrate is shown.

Example 2

Surface Activation

Figure 6:
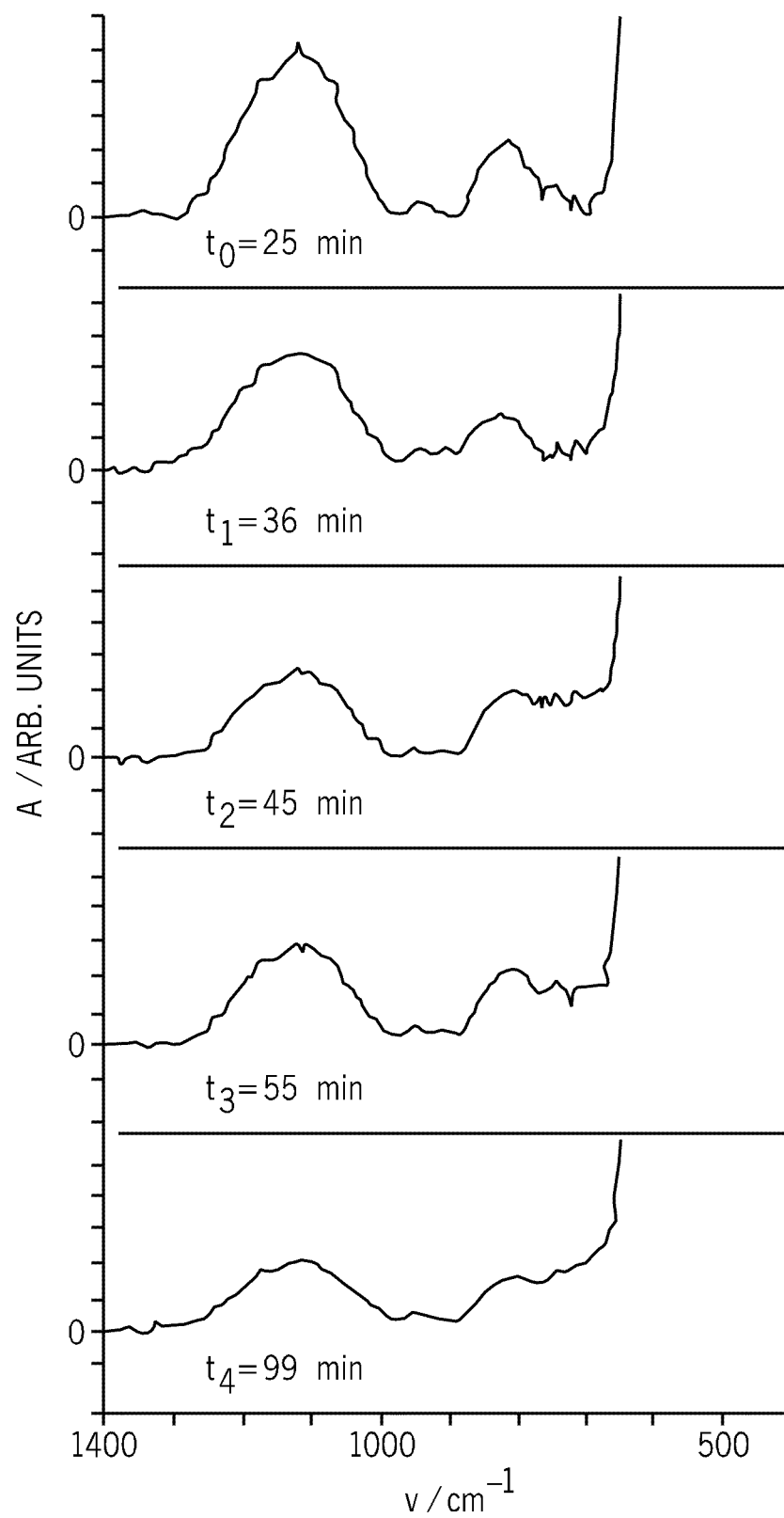
FIG. 6 are graphs of implementations of experimental data showing ATR/FTIR spectra of Al—OH on an ACG slide.

In the screening experiments, plasma of oxygen, argon, and mixed gases of oxygen and argon were tested for slide-surface activation. The residues (CO, $CO_2$, and $H_2O$) were removed under vacuum. It is the removal of this surface contamination that contributed to the success of grafting the desired organic compounds chemically. The surface was gauged with an attenuated total reflectance Fourier transform infrared (ATR/FTIR) spectrometer. The ATR/FTIR spectra showed Al—OH peaks at around 800-1100 $cm^{-1}$, as illustrated in FIG. 6, indicating that the surface had converted into Al—OH after the surface-cleaning process. According to implementations, the plasma treatment uses just enough plasma energy to clean and "tickle" the surface of the ACG slide to remove the organic contamination, but still hold the alumina layer without etching the underlying surface. The activation process was successfully completed by using a mere 6.8 W (at 680 V) of energy for 10 min under a gas-flow pressure of 270-300 mTorr. Argon plasma turned out to be the most effective for grafting sugar derivatives, as observed in later experiments. As shown in FIG. 6, the Al—OH peak intensity in the 800-1100 $cm^{-1}$ region decreased significantly from 25 to 99 min after plasma treatment.

The hydrophilic surface after plasma treatment gradually became hydrophobic, possibly because the oxide layer on the surface reformes. Disappearance of Al—OH from the substrate surface was traced by ATR/FTIR spectroscopy. The Al—OH peak intensity in the 800-1100 $cm^{-1}$ region decreased significantly over a matter of hours, as shown in FIG. 6. According to implementations, the ACG slides are activated with 3-aminopropyldimethylethoxysilane (APDMES) immediately after plasma treatment. This activated ACG surface was used to immobilize the sugar derivative of mannose and lactose with a PCL in the next step of the reaction.

Figure 7:
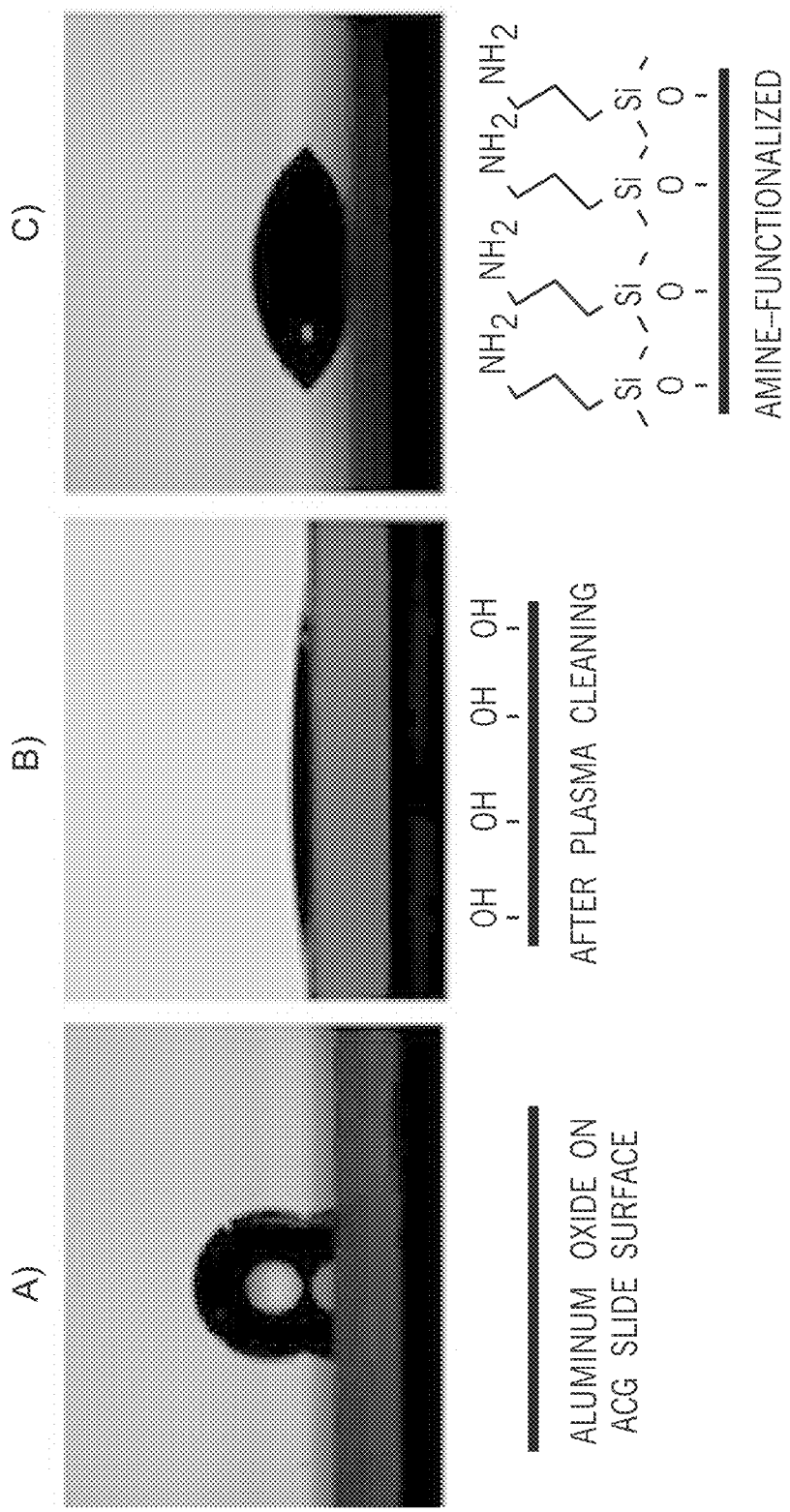
FIG. 7 are photographs of the water contact angle on ACG slides demonstrating the efficacy of activation.

As shown in FIG. 7, the water contact angle on the surface changed during surface activation. According to FIG. 7, the typical changes in water contact angle for ACG slides are shown. FIG. 7A shows a solvent-cleaned ACG slide; FIG. 7B shows an ACG slide treated with plasma; and FIG. 7C shows an ACG slide activated with 3-amino-propyldimethylethoxysilane. These samples were made and measured as an example with the nontransparent magnetron-sputtered ACG slide. Therefore, measurement of the contact angle can be used as a quick check of the completion of the activation process. Substrates with a high surface roughness tend to give smaller contact angles.

Example 3

Mannose with PCL Immobilized on the Activated Surface of the ACG Slide

As shown in FIG. 2, compound 27, which has a carboxy functional group, was synthesized. A solution of HBTU and compound 27 was manually spotted and microarrayed on the activated surface of the ACG slide. Amide formation on the surface of the ACG slide took place overnight at room temperature. All salt residues, as well as unbound mannose derivative, were washed away thoroughly with methanol and deionized water. After all these preparations, the substance was ready for mass identification and protein-binding evaluation.

Example 4

Mass Spectrometric Analysis of the Sugar Derivative Grafted on the ACG Slides The matrix-free porous silicon surfaces (DIOS) produced molecular-ion peaks with negligible sample fragmentation. The ACG slide dimensions (75.5×25.4×1 $mm^3$) fit well in the ultraflex mass spectrometry instrument; slides at each step of the treatment were analyzed, as shown in FIGS. 8 and 9.

Figure 8:
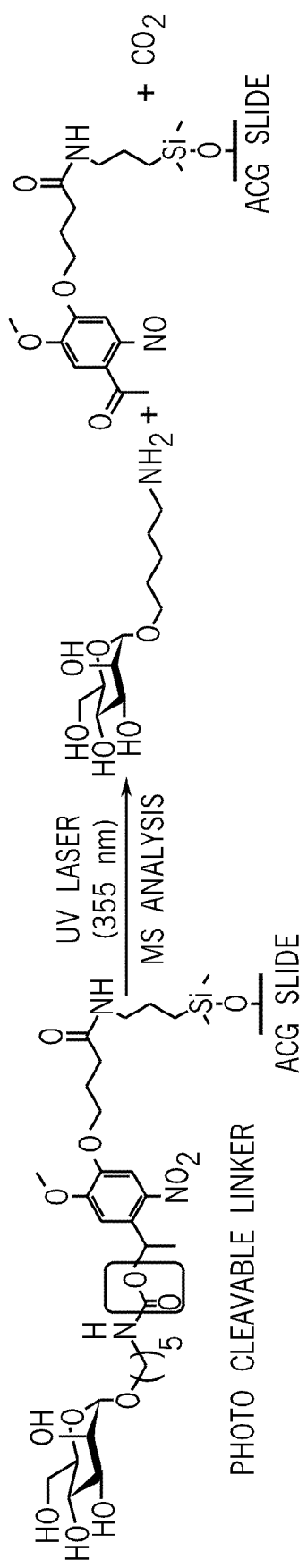
FIG. 8 is an implementation of a scheme for selective bond cleavage and detection of a sugar (mannose) derivative by ultraflex TOF mass spectrometry.

FIG. 8 is an implementation of a scheme for selective bond cleavage and detection of a sugar (mannose) derivative by ultraflex mass spectrometry.

Figure 9A:
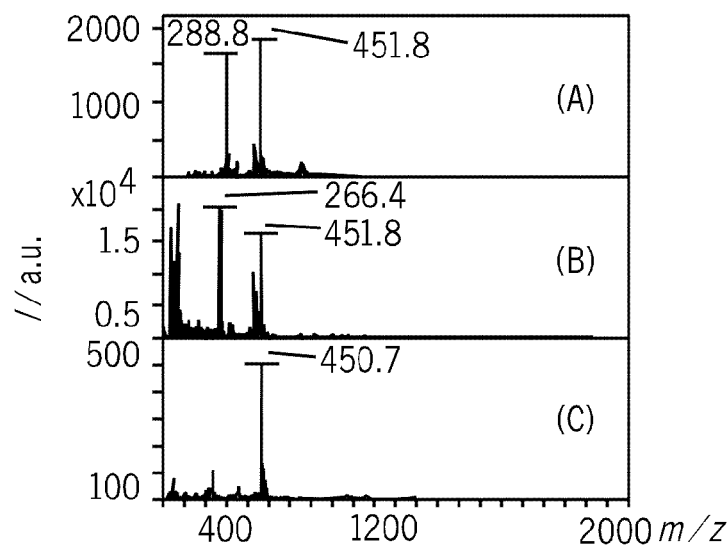
FIG. 9 shows implementations of mass spectroscopy data on a pure aluminum plate and an ACG slide.
Figure 9B:
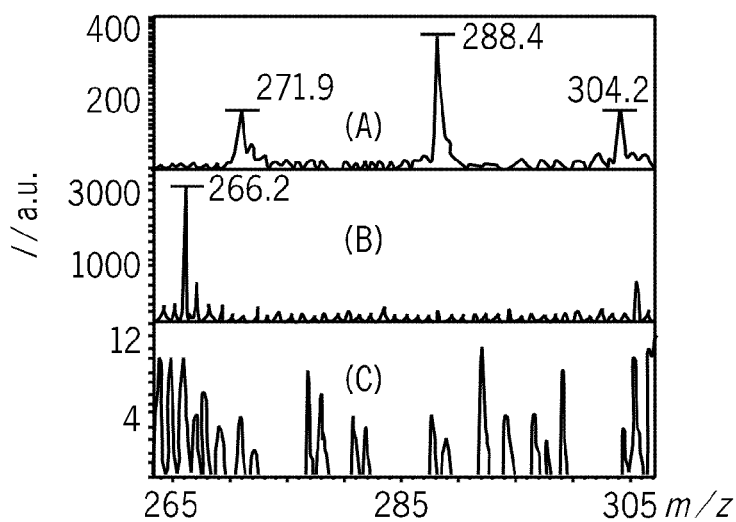

FIGS. 9A and 9B show the MS data for the early experiments on a pure aluminum plate and ACG slide, whereby the mannose peak intensities were relatively low. FIG. 9A shows the Ultraflex TOF mass spectra of mannose with PCL grafted on (A) a 99.999% pure aluminum plate (i mm thick) and (B) an ACG slide formed by cathode arc evaporation. (C) represents the background signal for cathode arc evaporation of the ACG slide. FIG. 9B shows the Ultraflex TOF mass spectra of FIG. 9A at the m/z region of interest.

Figure 9C:
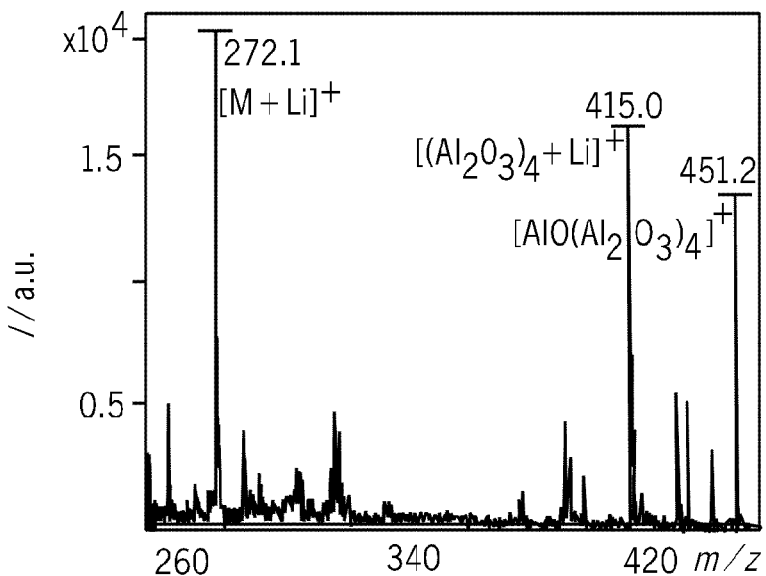

FIG. 9C shows TOF mass spectrum of mannose with PCL grafted on an ACG slide formed by cathode arc evaporation at the m/z region of interest. More specifically, FIG. 9C shows the MS data of the ACG slide produced by cathode arc evaporation, for which the surface-activation conditions were optimized and the peak intensity of the mannose derivative was high. Although the substrates gave large background peaks at m/z 415 and 451 (FIGS. 9A and 9C), the molecular weight of the mannose derivative (265) was detected quite easily by its adducts with proton (m/z 266), lithium (m/z 272), sodium (m/z 288), and sometimes potassium (m/z 304) ions.

It is theorized that under high vacuum, UV excimer laser energy vaporizes aluminum oxide clusters to the gas phase; ultraviolet photon ionization produces sparse mass spectra with relatively light aluminum oxide clusters. The majority of the oxide clusters in the gas phase under vacuum consisted of $AlO(Al_2O_3)_n$, even though the aluminum oxide clusters could exist in many different forms. In FIGS. 9A and 9C, the large background peaks that occurred at m/z 451 and 415 are speculated to belong to the oxide clusters $[(Al_2O_3)_4+Li]^+$ and $[AlO(Al_2O_3)_4]^+$.

Example 5

Semiquantitative Comparison of the Content of Mannose with Its Protein-Binding Capability The optimization of the plasma gas treatment on the same type of ACG slide was evaluated by the fluorescence intensity of the immobilized sugar-protein binding. FIG. 10 was obtained by selecting the type of gas used for plasma cleaning. ACG slides produced by cathode arc evaporation were exposed to oxygen, argon, or a mixture of oxygen and argon plasma gases prior to aminosilane grafting. A 10×10 block (100 spots) of the mannose derivative (sugar complex solution, 160 mm) was microarrayed onto the substrate surfaces. The sugar complex solution was also manually spotted on each of these slides (1 mL per spot) specifically for mass identification. Therefore, these slides were analyzed first by mass spectrometry and then subjected to biotinylated ConA binding followed by Cy3-tagged streptavidin detection. FIG.

10A a)-d) shows the protein-binding assays of the arrayed slides; FIG. 10C shows the fluorescence intensities of substrates versus those of the commercially available glass slide. The intensity difference shown in FIG. 5 demonstrates the absolute effect of the physical properties of the substrate. The intensity difference in FIG. 10C resulted from the effects of both the physical properties of the specific substrates and the binding-site architectures between the immobilized sugar and its binding proteins. Both sets of data indicate that argon plasma treatment of the ACG slide surface produced the best substrate for mannose grafting, hence the mannose-protein binding.

Figure 10A:
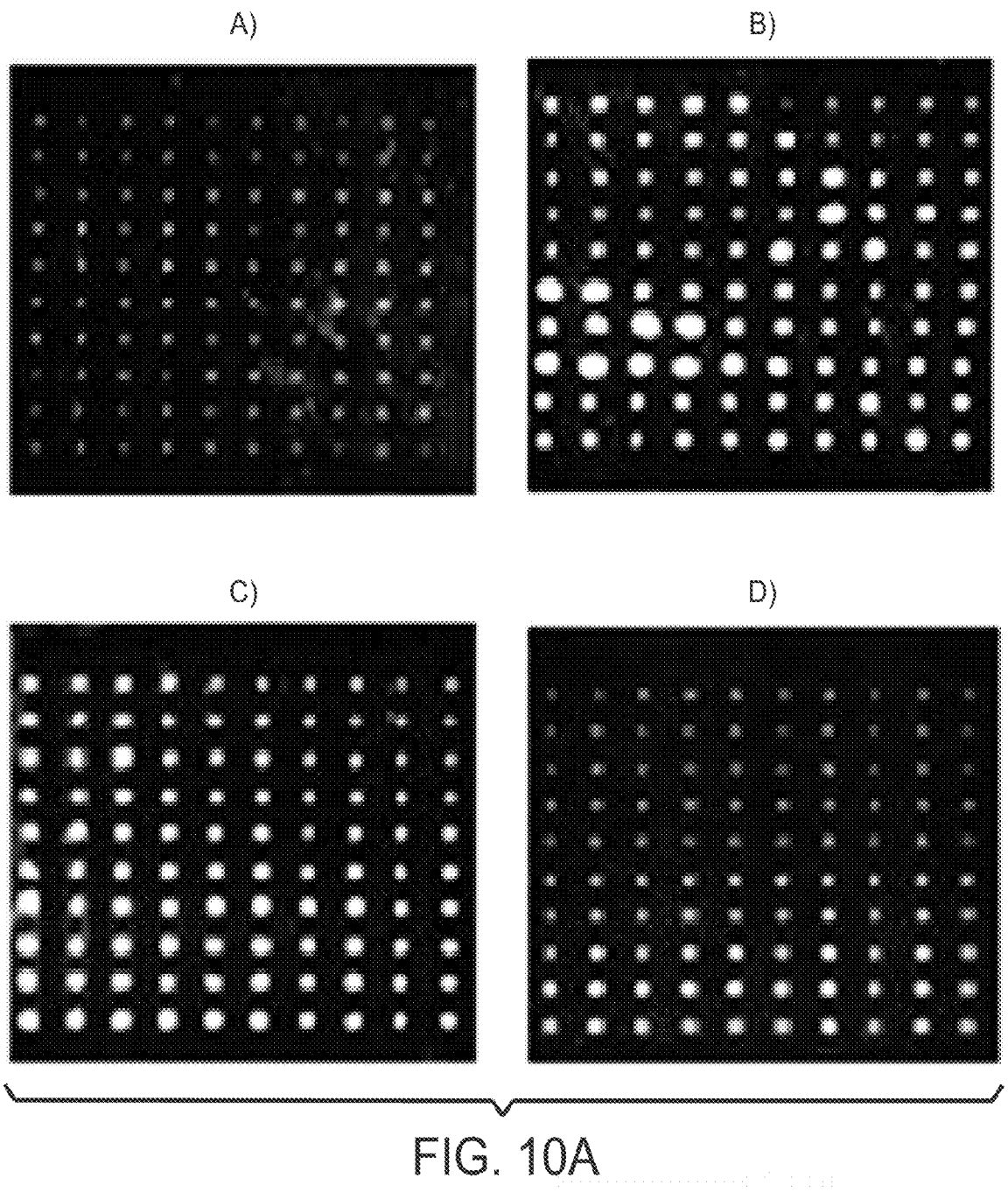
FIG. 10 shows implementations of protein-binding assays of ACG slides formed by cathode arc evaporation upon treatment with a) oxygen plasma (Al-1), b) argon plasma (Al-2), and c) a mixture of oxygen and argon plasma (Al-3) prior to APDMES grafting.
Figure 10B:
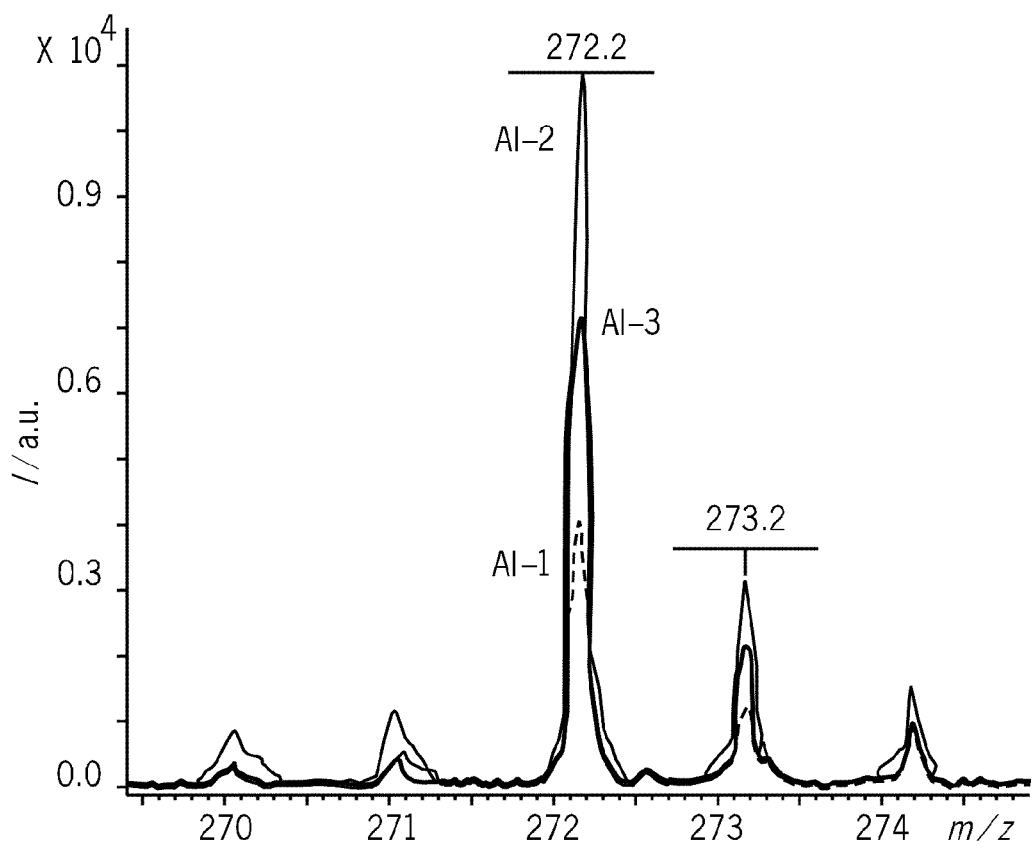
Figure 10C:
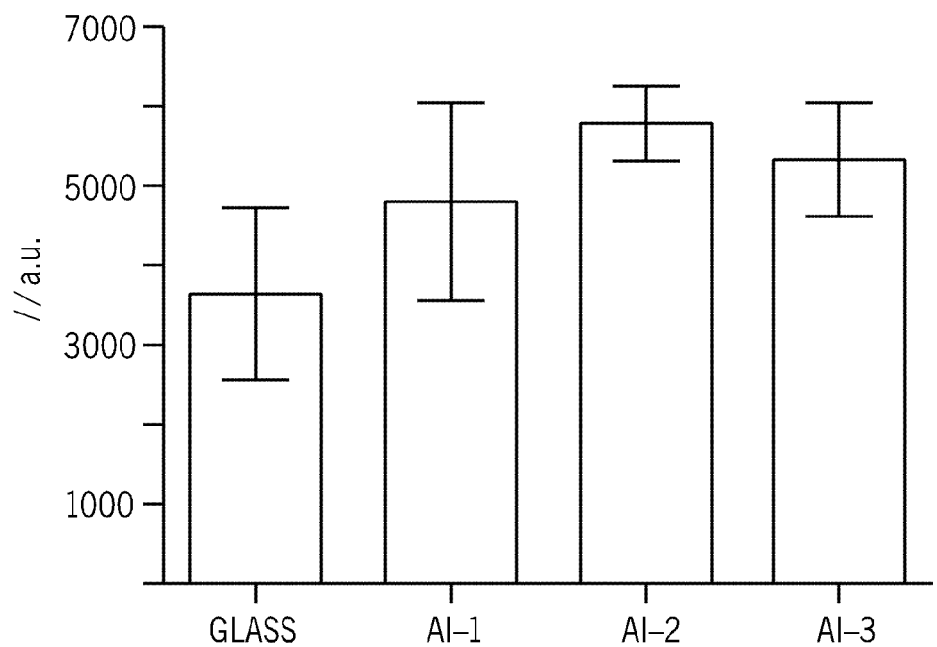

FIG. 10A shows protein-binding assays of ACG slides formed by cathode arc evaporation upon treatment with a) oxygen plasma (Al-1), b) argon plasma (Al-2), and c) a mixture of oxygen and argon plasma (Al-3) prior to APDMES grafting. In d), protein-binding assay of the commercially available $NH_2$-glass slide from Corning Glass (#40004) are shown. FIG. 10B shows the signal intensities from MALDI mass spectra for the mass identification of sugar. The maximum-intensity spectra (70% fluence) observed from each substance was used to create the spectra of FIG. 10B. FIG. 10C shows fluorescence intensities of a)-d) with standard errors calculated with an arrayWoRx fluorescence spectrometer. The array was made in four blocks per slide with 10×10 (100) spots per block of the same aqueous solution of sugar complex. Only the best block from each slide was chosen (as shown in b)-d)); large spots among the best blocks were eliminated for fluorescence-intensity calculations.

Figure 11:
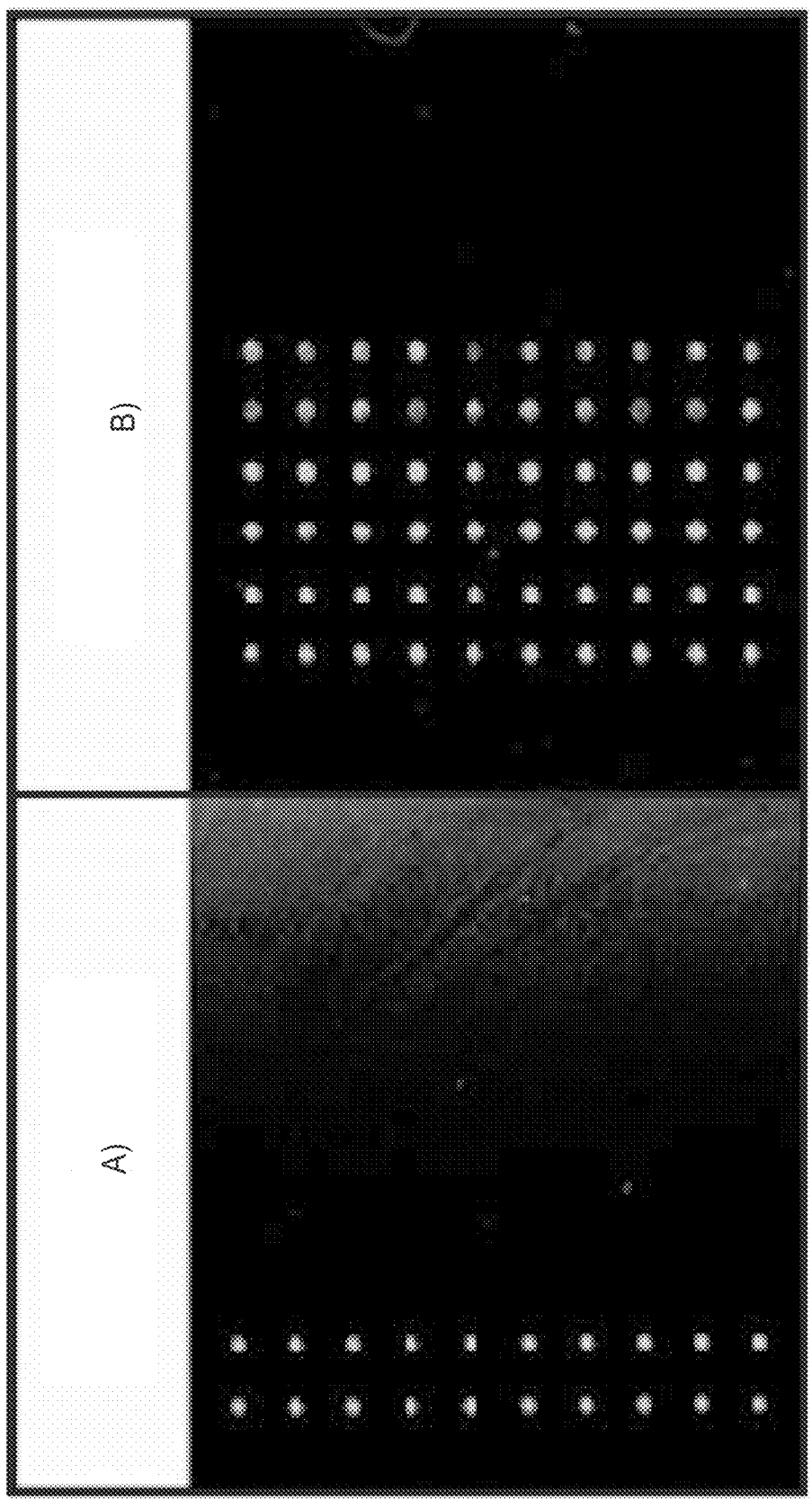
FIG. 11 are photographs of implementations of a fluorescence-tagged protein-binding assay of mannose immobilized on a glass slide and an ACG slide.
Figure 12A:
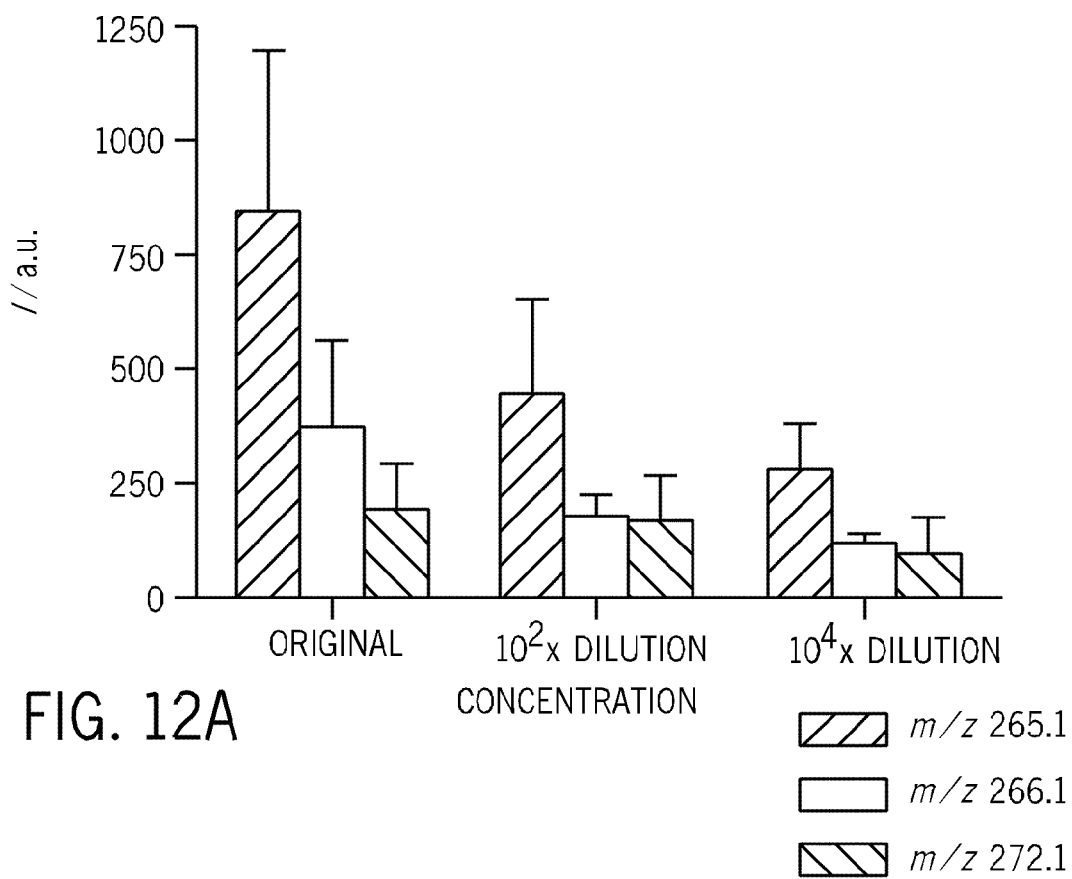
FIG. 12 are graphs of implementations of experimental data showing comparison of the peak intensities of the ultraflex TOF mass spectra of mannose with a photo cleavable linker (PCL) grafted on ACG slides with the fluorescence intensities of mannose-protein-bound ACG slide formed by thermal coating followed by electrochemical anodization on the slide surface.
Figure 12B:
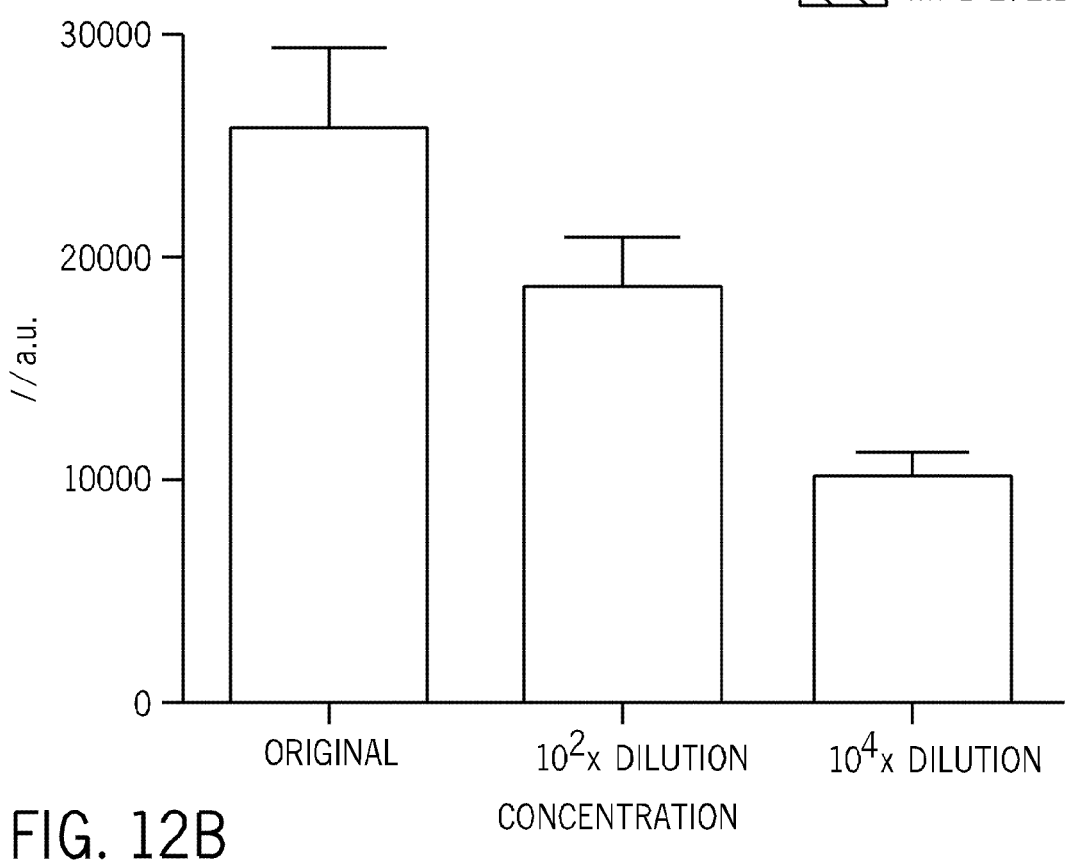

A semiquantitative comparison of the content of the immobilized mannose and the mannose-protein binding capability are given in FIGS. 11 and 12. Two different types of slide substrates were used for immobilizing mannose with the built-in PCL, that is, the $NH_2$ functionalized glass slide and the APDMES-activated $NH_2$-ACG slides that were thermally coated with aluminum followed by surface-anodization treatment. The mannose-ACG slide was first subjected to MS analysis for molecular-weight identification and then to protein-binding evaluation along with the mannose-glass slide. FIG. 11 shows the protein-binding data resulting from the two different types of slide substrates. It clearly indicates that the mannose-ACG slide (FIG. 11b)) showed higher fluorescence of Cy3 with a better sensitivity than the glass slide (FIG. 11a)). The fluorescence intensity from the ACG slide was calculated and is given in FIG. 12B.

The differences in fluorescence intensity in FIG. 11 were caused by the difference in physical properties of the slide substrates and the difference in the degree of mannose-ConA and Cy3-streptavidin binding. This difference in turn, implies a variation in the grafting density of mannose on the substrate surface. A recent report indicated that the interaction between ConA and mannose becomes weak when the density of mannose on the substrate surface is about 100 Å apart, thus reflecting the degree of polyvalent interaction.

MS analysis of the same mannose-ACG slide (FIG. 11b)) revealed the parent peak (m/z 265) as well as the proton (m/z 266) and lithium (m/z 272) adducts. In analyzing this slide, each manually spotted (in the series of dilutions) sample was measured six times with 500 shots per measurement. The average peak intensity with standard deviation is given in FIG. 12A, which demonstrates that MS could still identify the sugar, even when the concentration of the solution for grafting was diluted to 15.6 nm. The signal intensities measured by MS (FIG. 12A) are further compared to the fluorescence intensities shown in FIG. 12B. The descending trends of these two different measurements are similar. Apparently, the quantity of immobilized sugar reflects its protein-binding capability.

FIG. 11 are photographs of implementations of a fluorescence-tagged protein-binding assay of mannose immobilized on a glass slide and an ACG slide. The $NH_2$-functionalized glass slide was purchased from Corning Glass (#40004). The ACG slide was thermally coated with pure aluminum and then electrochemically anodized. The array was made in a block of 10×6 (60) spots. The solution of sugar-HBTU complex (156 mM) was prepared to 100× and 10000× dilution. Each solution was spotted in two columns (20 spots) in the block for grafting. Substrate a) shows fluorescence only in the first two columns (the solution of sugar complex), but substrate b) shows signals up to the sixth column (10000× dilution of the starting solution of sugar complex).

FIG. 12 are graphs of implementations of experimental data showing comparison of the peak intensities of the ultraflex TOF mass spectra of mannose with PCL grafted on ACG slides with the fluorescence intensities of mannose-protein-bound ACG slide formed by thermal coating followed by electrochemical anodization on the slide surface. The concentration of the mannose solution varied from 156 mM to 102 (1.56 mM) and 104× dilution (15.6 nM). In FIG. 12A, average peak intensities of mannose mass spectrometric adducts obtained at m/z 265.1 $[M]^+$, 266.1 $[M+1]+$, and 272.1 $[M+Li]^+$. In FIG. 12B, corresponding fluorescence intensities of the same mannose-ACG slide sample obtained from the fluorescence-tagged protein-binding assay is shown.

Example 6

Utility of ACG Slides on Carbohydrate Microarrays

Figure 13A:
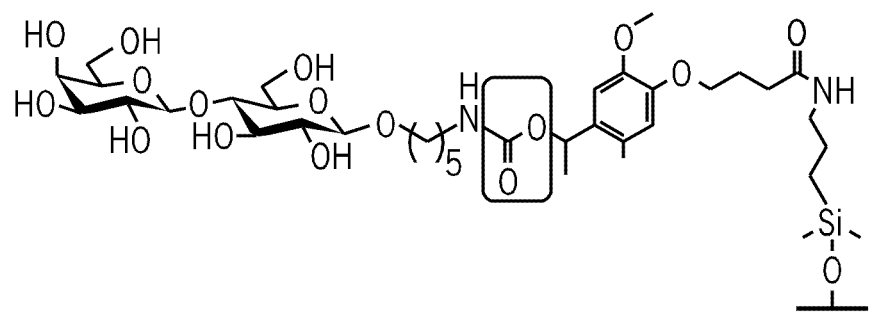
FIG. 13 shows data related to implementations of utilization of $NH_2$-ACG surfaces modified through conversion into NHS-ACG by treatment with disuccinimidyl suberate (DSS) in DMF and diisopropylethylamine.

By using the synthetic route shown in FIG. 2, lactose with PCL was also immobilized on an ACG slide, as shown in FIG. 13A. As seen in the MS analysis of this sample (FIG. 13B), the interference occurred resulting from the sparse aluminum oxide peaks at 415 and 451. However, the molecular weight of the lactose derivative (m/z 427) could still be clearly identified by its adducts with proton (m/z 428), sodium (m/z 450), and potassium (m/z 466) ions.

For further utilization of this newly fabricated substrate, the $NH_2$-ACG surface was modified through conversion into NHS-ACG by treatment with disuccinimidyl suberate (DSS) in DMF and diisopropylethylamine. With glass slides as reference, a Globo H derivative with an amine functional group was arrayed on the NHS-ACG slide (FIG. 13C) and subjected to VK9 (a mouse IgG anti-Globo H monoclonal antibody) protein-binding evaluation. The results in FIGS. 13D and 13E indicate that the ACG slide shows the highest fluorescence intensity among all three samples.

Figure 13B:
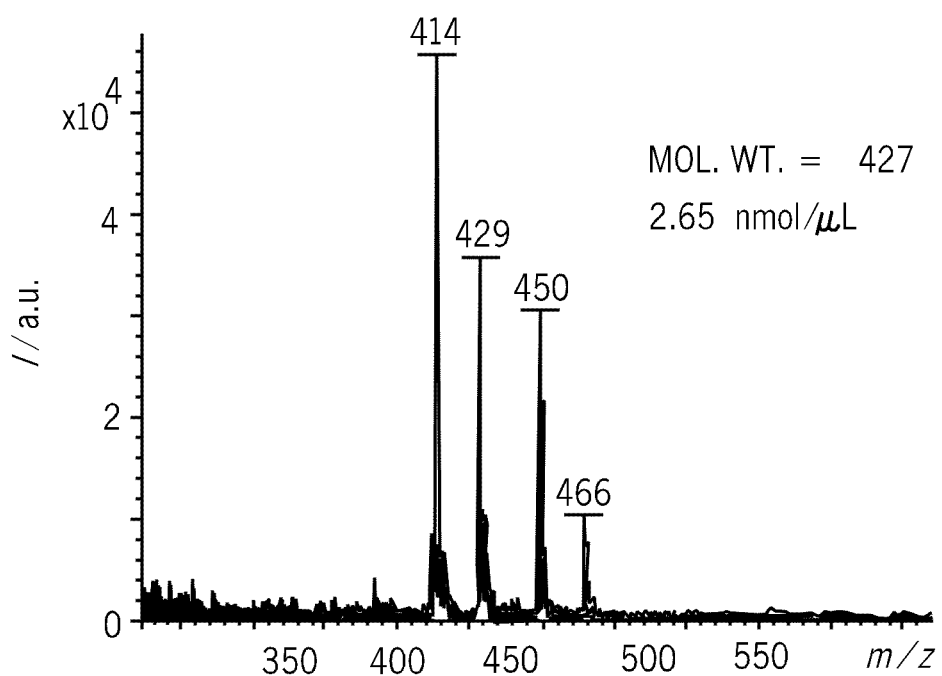

FIG. 13A shows Lactose-ACG slide with PCL. FIG. 13B shows Ultraflex TOF mass spectra obtained from the lactose-ACG slide with PCL. FIG. 13C shows Globo H-ACG slide with no PCL. FIG. 13D shows fluorescence-tagged protein-binding assay of Globo H immobilized on NHS-glass slide, $NH_2$-modified glass slide (Corning #40004), and NHS-ACG slide. Finally, FIG. 13E shows corresponding fluorescence intensities calculated from FIG. 13D with a GenePix 4000 fluorescence scanner.

Example 7

Factors Affecting Fluorescence Intensity-Substrate Property and Surface Morphology The optical properties of substrates apparently affect the fluorescence intensity. Fluorescence (Cy3) is the sole light source in a protein-binding assay. Glass as well as porous silicon both pass and reflect light to different extents. On the contrary, aluminum-coated glass can be fabricated such that it becomes completely nontransparent and minimizes the "waste" of light provided by the light source.

The surface morphology of the substrate could affect the grafting density in immobilizing sugars. The NAO surface showed only 75% oxide content. On the contrary, the AAO surface contains 100% aluminum oxide, thus providing a stable surface and leading to a steady immobilizing density of the final slide for assay.

Substrate stability may also be affected by the way in which the surface is chemically treated. An example is the surface with cross-linked amines versus that with a monolayer of amine functional groups, both of which were made by activating the ACG slide with either 3-aminopropyltriethoxysilane (APTES) or 3-aminopropyldimethylethoxysilane (APDMES). Various chemical treatments of the ACG slide surface are under investigation.

Example 8

Factors Affecting Fluorescence Intensity-Binding-Site Architectures/Interactions of Proteins with Sugars Immobilized on the Substrate Surface Under our experimental conditions, both concanavalin A and streptavidin exist as tetramers of their quaternary structures. The ratio of the dimensions of mannose to ConA is about 1:400 (corresponding to their molecular weight of 265 vs. 104 kDa). Owing to the geometric constraint, only two binding sites per tetramer of biotinylated ConA are available for mannose binding on the surface. On the high-density mannose array surface, each ConA tetramer would bind two molecules of mannose, and the two mannose molecules would probably be grafted on the surface not too far away from each other. As the chain length of the mannose derivative increases, the grafted mannose becomes further away from the substrate, and a high degree of randomness of the interaction could occur when both the grafting density and the amount of immobilized sugar-protein binding increase. Furthermore, the flexible docking of the streptavidin-Cy3 complex to biotinylated ConA was allowed. A similar geometric restriction can also be illustrated for Globo H, IgG monoclonal antibody VK9 (from mouse), and its goat anti-mouse IgG protein. The binding-site architecture between sugar and proteins could affect the density of the fluorescence-tagged protein and, thus, the fluorescence intensity in the sugar-protein-binding assay.

One purpose of studying the surface immobilization of sugars is to mimic the ligand interactions that occur on the cell surface of biological entities, for example, the existence and overexpression of the sugar antigen Globo H on the surfaces of normal and malignant cells. The sugar antigens, when overly populated on the cell surfaces, could result in massive polyvalent carbohydrate-protein interactions and greatly impact the provided biological function of the living entities. This study provides a more precise quantitative measurement and comparison of such a biological system.

Example 9

Preparation of PTFE-Like ACG Slides

To prepare the PTFE-like ACG slides, triethoxysilane 1 and phosphonic acid derivatives 3 were synthesized and used for reaction with the oxidized aluminum surface. Fabrication of silane based slide involves a two-step chemical reaction. The first step was to functionalize the aluminum oxide surface to amino groups by using compound 1 (FIG. 14) as a grafting reagent. This step was conducted under a moisture-free environment to avoid side reactions. In the second step, amide bond formation took place between NHS activated polyfluoro hydrocarbon compound 2 (FIG. 14) and the amino group on the surface of the slide. On the contrary, the phosphonic acid based PTFE-like ACG slide was made in a one-step chemical reaction. An aqueous solution of 3 was reacted by sonication with the cleaned aluminum oxide surface to form a monolayer of perfluorophosphonate covalently bonded onto the surface. The covalent bond formation of phosphonic acid can be confirmed by FTIR and contact angle, as shown in FIG. 28B. These two types of slides were checked with MS-TOF spectrometry for background test, and both showed a clean baseline of the slide background. The unwanted sparse aluminum oxide peaks observed in our previous ACG slides were not seen with this method (see FIGS. 26 and 27).

As illustrated in FIG. 28A, FTIR spectrum of Pure Compound 3 (HDFDPA, 3,3,4,4,5,5,6,6,7,7,8,8,9,9,10,10,10-heptadecafluorodecylphosphonic acid) and an FTIR spectrum of ACG surface grafted compound 3. FIG. 28B illustrates the water Contact Angle ($\cong 120°$) image of the phosphonated ACG slide surface.

Figure 14:
FIG. 14 are chemical formulae of structures of compounds used in ACG-mass spectroscopy experiments.

As shown in FIG. 14, the compounds are as follows: aminopropyltriethoxysilane (APTES, 1); N-Succinimidyl 4,4,5, 5,6,6,7,7,8,8,9,9,10,10,-11,11,11-heptadecafluoroundecyl carbonate 2; (3,3,4,4,5,5,6,6,7,7,8,8,9,9,10,10,10-heptadecafluorodecyl) phosphonic Acid (HDFDPA, 3), 4 to 10 are poly-fluorinated derivatives of mannose (4), lactose (5), Gb5 (6), Globo H (7), cellobiose (8), cellolotriose (9) and cellotetraose (10).

Example 10

Creation of Non-Covalent Bond Glycan Array on the PTFE-Like ACG Slides

Figure 16:
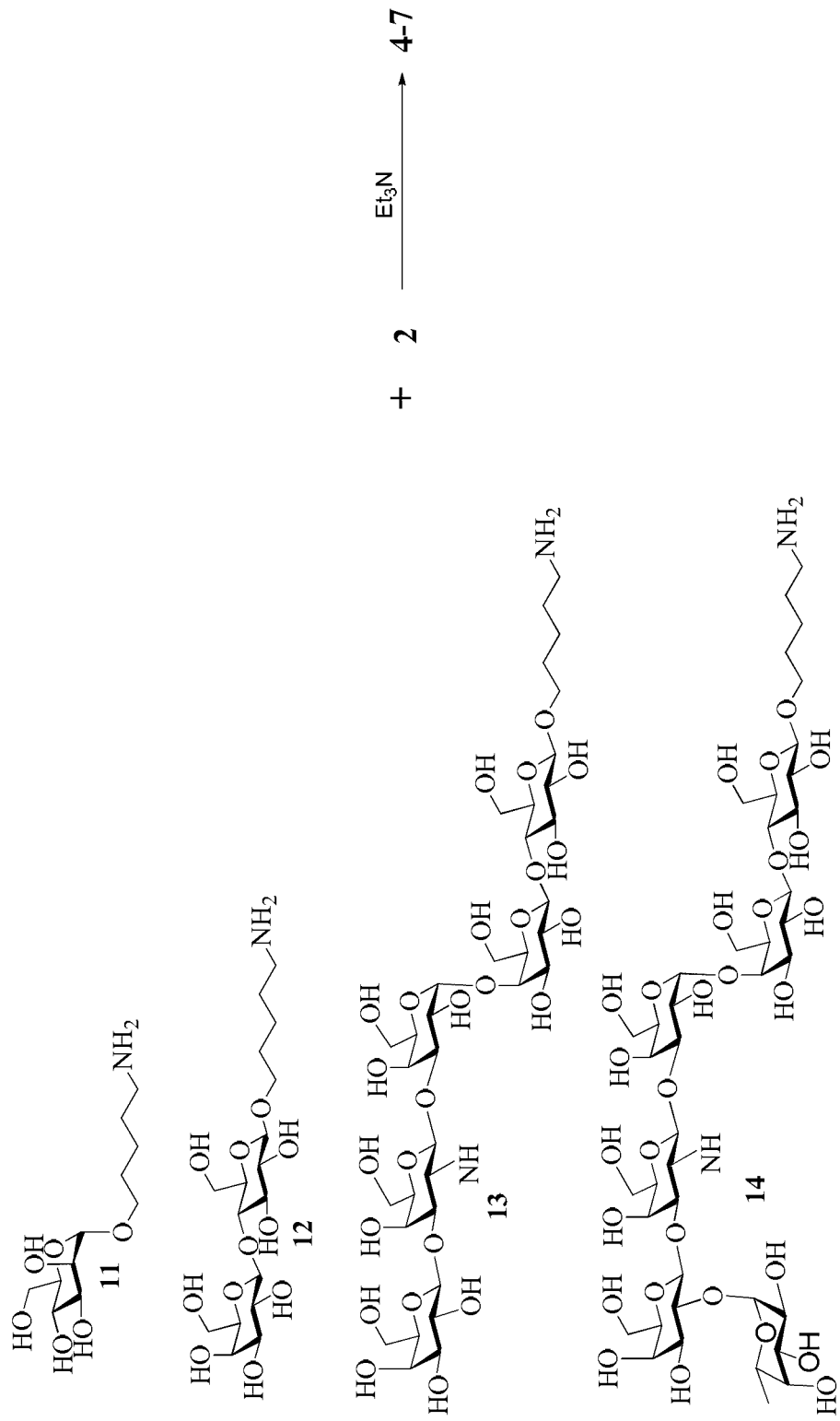
FIG. 16 is a scheme illustrating the synthesis of implementations of poly-fluorinated carbohydrates 4-7.

With this encouraging result, the phosphoric acid based slide was used to create the glycan array for the experimental procedures outlined in FIG. 15. Mannose with an amino linker 11 was reacted with compound 2 to synthesize the poly-fluorinated (—$C_8F_{17}$) tail 4 and used as the model compound, as illustrated by the scheme shown in FIG. 16. A solution of this sugar derivative was spotted robotically onto the PTFE-like ACG slide surface. After incubation, the slides were rinsed repeatedly with distilled water and subjected to MS-TOF analysis. A very clean mass spectrum was obtained. The mass spectrum of this monolayer reveals peaks at 806 and 822 for the sodium and potassium adducts, respectively. Following the MS analysis, the same slide was used for protein binding analysis by using Alexa 488-labeled Concanavalin A as a protein source. To further extend the scope of this type of glycan array, use of the compounds 12-14 that were synthesized by our laboratory previously as the starting materials. Poly-fluorinated Gb5 5, lactose 6 and Globo H 7 were synthesized, as illustrated in FIG. 16 and immobilized them onto the PTFE-like ACG slide surface for both mass analysis and protein binding assays according to the methods disclosed herein.

Figure 17A:
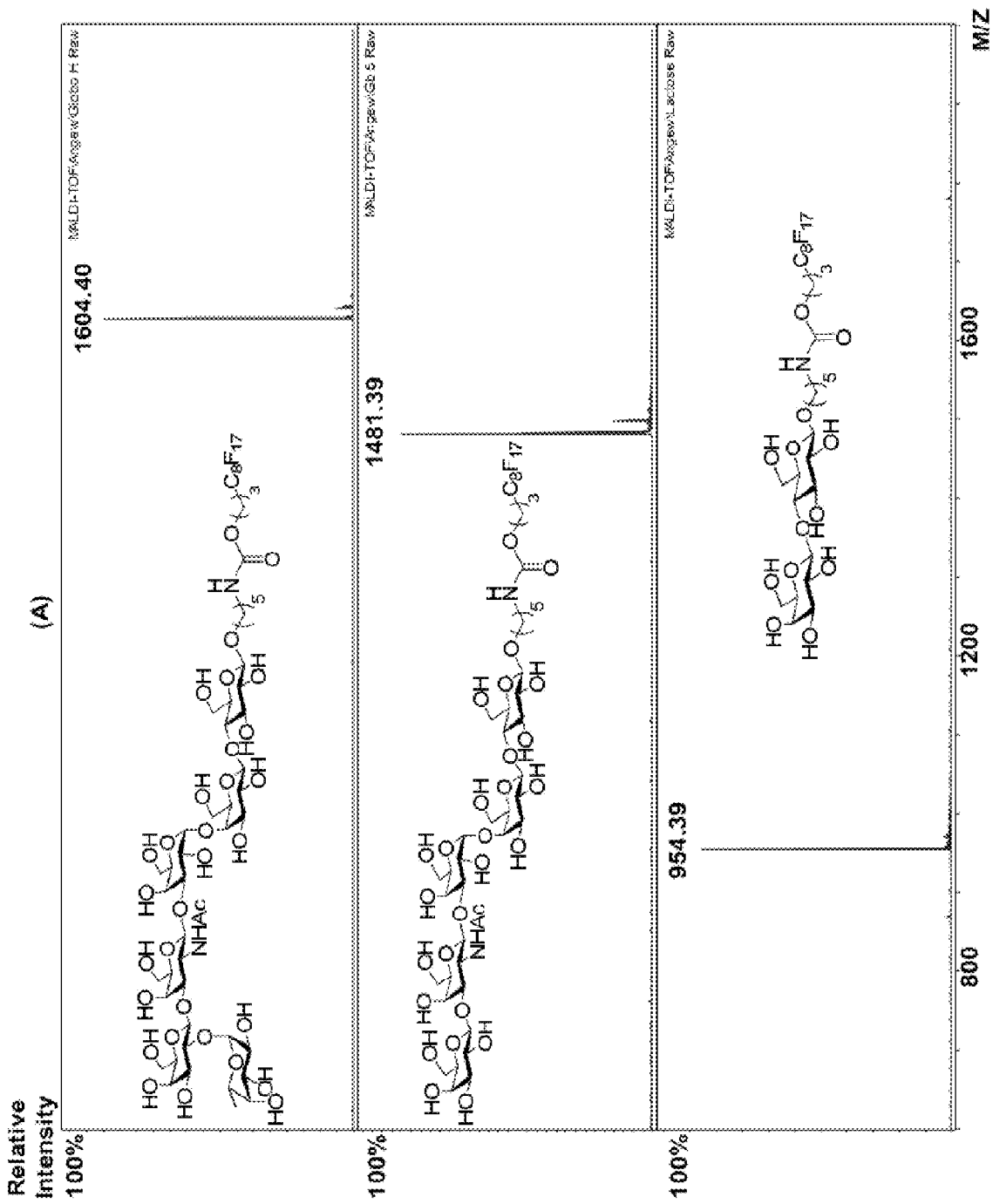
FIG. 17 are representations of implementaions of experimental data using the PTFE-like ACG slides having poly-flourinated carbohydraytes bound to them.

As shown in experimental implementations illustrated by the data shown in FIG. 17A, without adding additional matrix, no fragmented signal was found, even with the use of such labile sugar as Globo-H. FIG. 17A illustates MALDI mass spectrometric analysis data of polyfluorinated Globo H 7 (MW. 1604.40), Gb5 5 (MW. 1458.39) and lactose 6 (MW. 932.21) immobilized on PTFE-like ACG slide as their sodium adducts [M+Na]+ at 1627.44, 1481.39, and 954.39, respectively. The fluence rate is 12% without matrix addition.

Figure 17C:
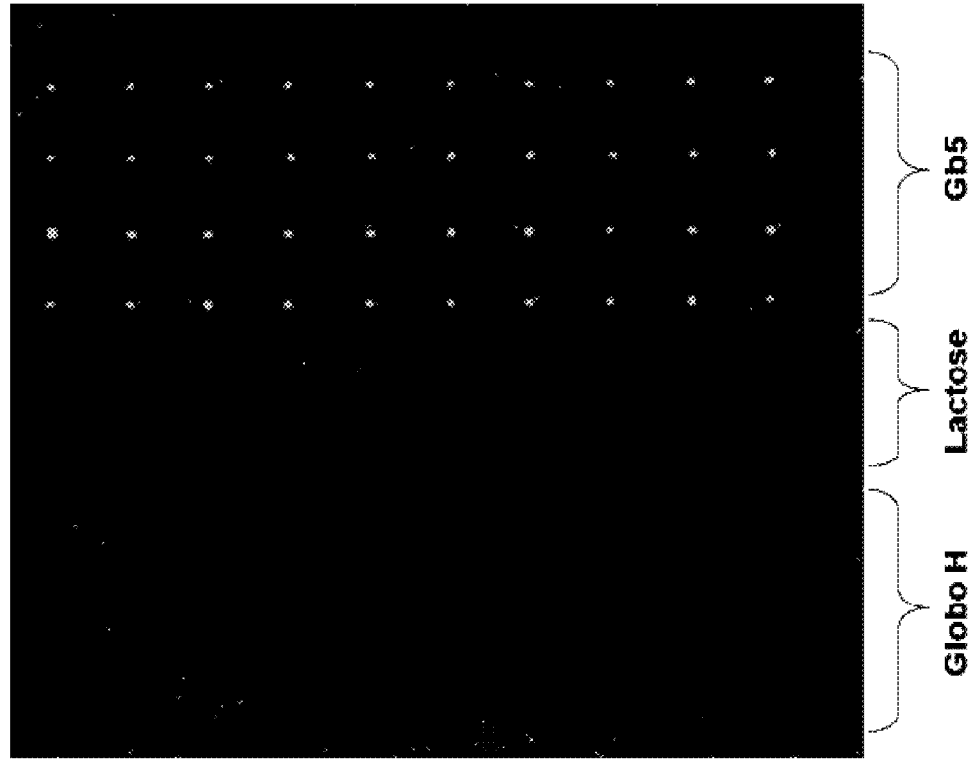
Figure 17B:
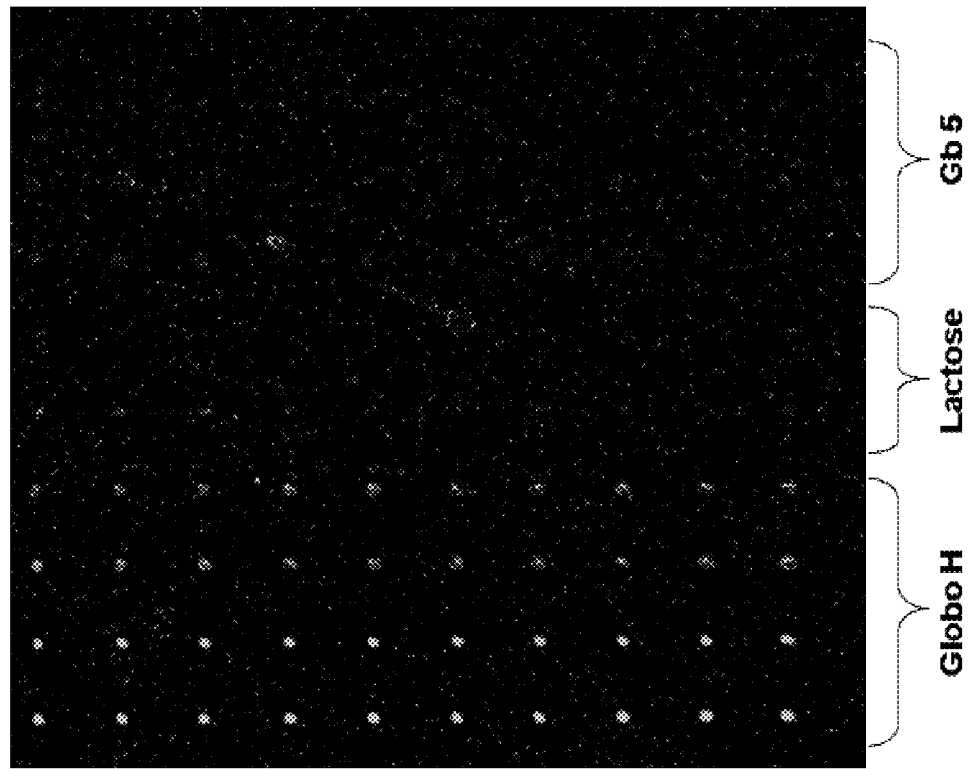

According to implementations of experimental data in FIG. 17B, these glycan arrays retained their sugar-protein binding patterns. FIG. 17B is a protein-binding assay of GloboH/VK9/anti-VK9-Cy3. FIG. 17C is a protein-binding assay of Gb5/anti-SSEA3-A488. The matrix was a 10×10 (100 spots) array of perfluorinated Globo H (left 4 columns), lactose (5th & 6th columns, served as the negative control), and Gb5 (right 4 columns).

Figure 18:
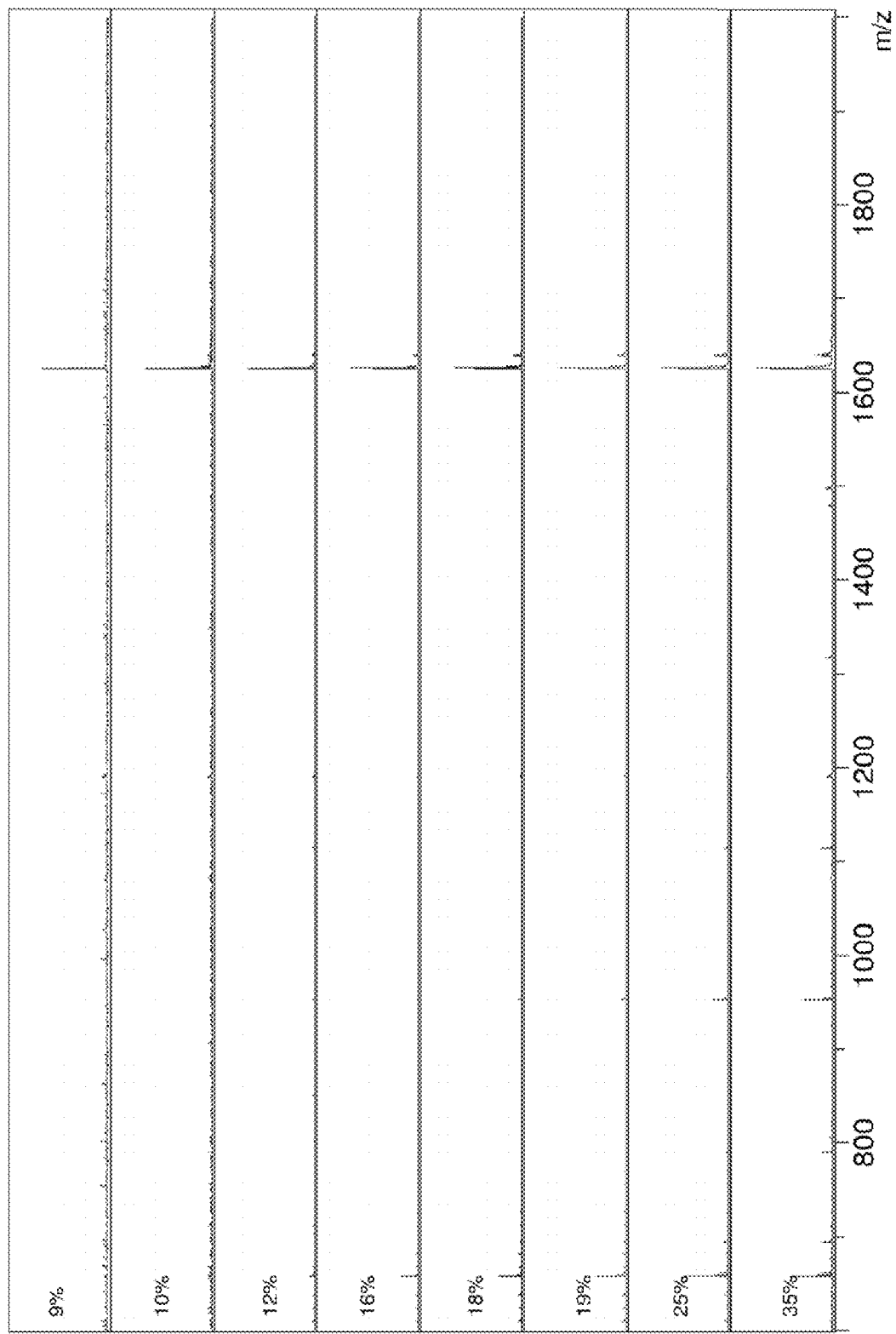
FIG. 18 are graphs of implementations of experimental data of mass spectra of Globo H on ACG slide by using different laser fluence rate without matrix addition.

The effect of laser fluence rate and matrix on this new surface was also investigated. Taking the labile carbohydrate Globo H as an example, it often loses a fucose moiety when used in MALDI-MS. By using mass spectrometry as a detector, the results were showed in table 1. Without adding matrix, a high signal to noise (S/N) ratio (22) in very low laser fluence rate (9%) is observed, and under this low laser fluence rate, no fragmented signal was found. When the fluence rate increase to 10%, the S/N ratio enhance to 40 without any fragmentation. FIG. 18 illustrates the resulting mass spectroscopy data under various laser fluence conditions without matrix added.

Figure 19:
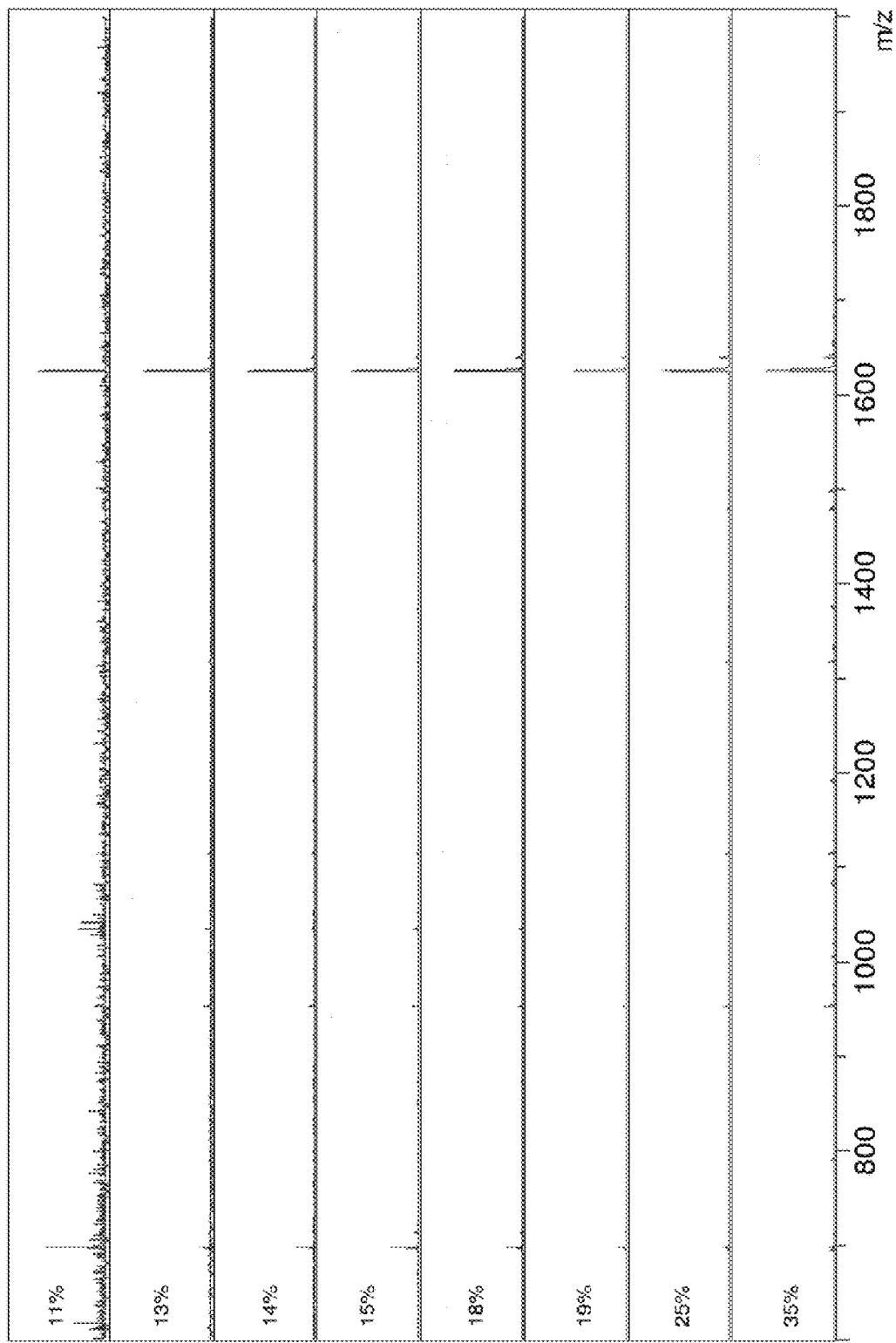
FIG. 19 are graphs of implementations of experimental data of mass spectra of Globo H on ACG slide by using different laser fluence rate with matrix.

FIG. 19 illustrates the same experiments, but with matrix. DHB was added as a matrix to check the matrix effect on the ACG surface. The S/N is only 7.3 when the fluence rate is 11%. To increase the fluence rate to 13%, the S/N is 61% with 6% fragmentation signal. The DHB matrix therefore doesn't enhance the S/N signal when low laser fluence rate be used. However, it can play a role to enhance S/N and reduce the fragmentation when the fluence rate over 25%, as shown in Table 1.

TABLE 1

S/N ratio of Globo H under different laser fluence rate with or without matrix addition. (Fluence: the laser power (or fluence rate) applied on the slide surface; GH S/N: the Signal/Noise ratio for globo H; Frag. S/N: the Signal/Noise ratio for the peak of fragmentation of globo H.)

| Matrix-assisted Desorption/Ionization | | Matrix-free Desorption/Ionization | |
|---|---|---|---|
| Fluence Rate | GH S/N | Frag. S/N | Fluence Rate | GH S/N | Frag. S/N |
| 11% | 7.3 | 0 | 9% | 22 | 0 |
| 13% | 61 | 6 | 10% | 40 | 0 |
| 14% | 157 | 13 | 12% | 218 | 5 |
| 15% | 316 | 25 | 16% | 275 | 10 |
| 18% | 1690 | 87 | 18% | 375 | 17 |
| 19% | 1956 | 108 | 19% | 741 | 64 |
| 25% | 3128 | 168 | 25% | 2184 | 356 |
| 35% | 1445 | 125 | 35% | 1514 | 373 |

Example 11

Cellulase Activity Studies

From the previous studies, poly-fluorinated carbohydrate immobilized on the PTFE-like ACG slide is easily ionized/desorbed by low laser energy. High S/N mass spectrum without fragmentation is therefore obtained, making the devices of the present disclosure suitable for glycosidase specificity and activity studies.

Enzymatic hydrolysis of the immobilized poly-fluorinated cellobiose 8 (see FIG. 14) was first conducted in situ on the phosphonic acid slide surface. Three commercially available cellulases, *Aspergillus niger* (*A. niger*), *Trichoderma reesei* (*T. reesei*), and *Trichoderma viride* (*T. viride*) were prepared separately at 5 U/mL in a sodium acetate (25 mM) buffer solution (pH 5) and loaded onto the functionalized slide which has been divided into 16 wells using Fast Frame reaction chambers. For comparison, an aliquot of enzyme solution (100 µL) was added to the solution of fluorinated cellobiose (100 µL of 0.5 mM) in eppendorfs to carry out the enzymatic hydrolysis reactions in solution. After the reaction, it was transferred to the empty wells of the same slide. Each well was rinsed separately three times with de-ionized water and the slide was dried again under high vacuum before subjecting to MS-TOF analysis.

Figure 20A:
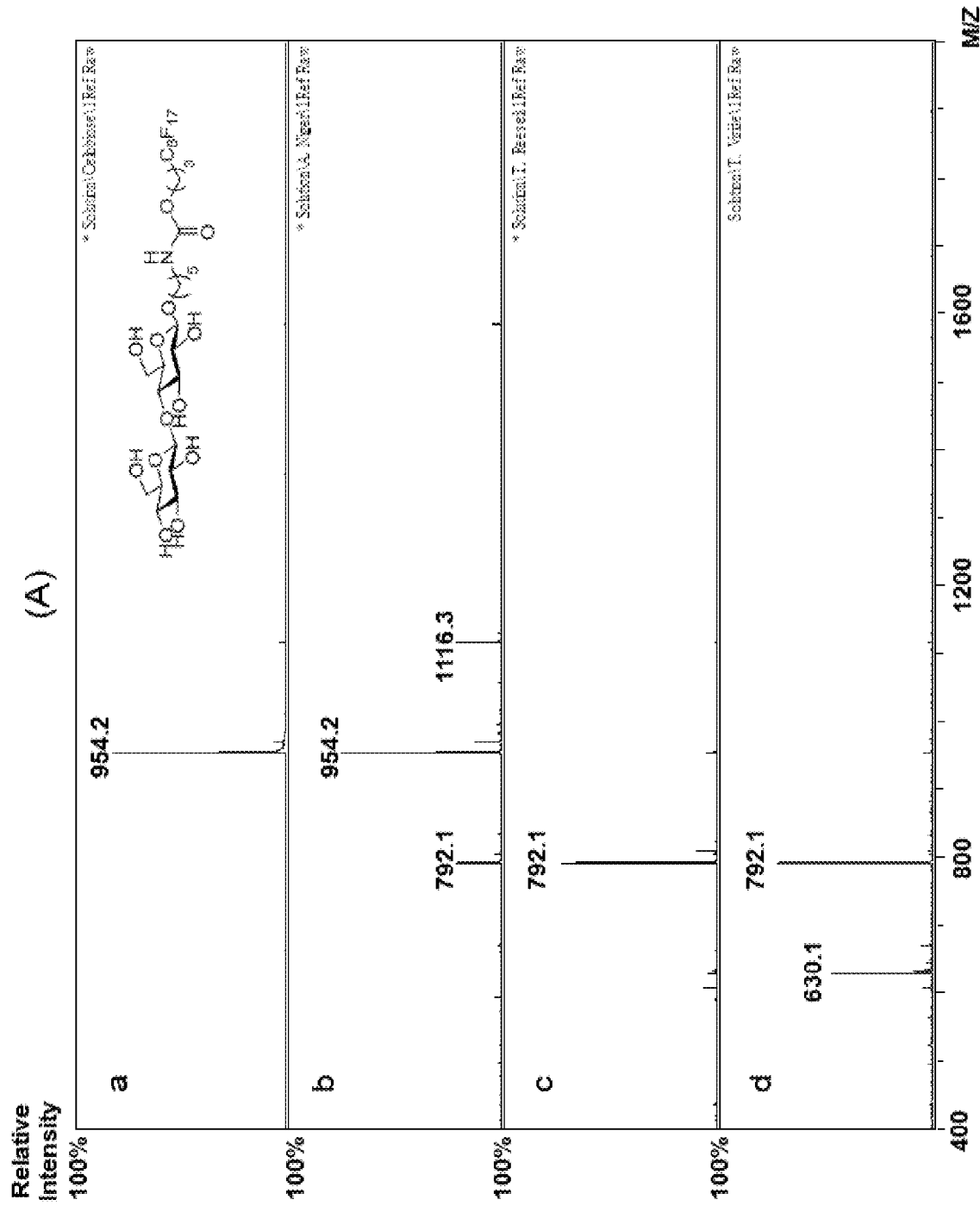
FIG. 20 are graphs of implementations of experimental data of MS-TOF data of enzymatic hydrolysis of poly-fluorinated cellobiose in solution and immobilized on PTFE-like ACG slide with the cellulase proteins from *A. niger, T. reesei,* and *T. viride;*

Under MS-TOF analysis, the clean background baseline allowed calculation of the percentage of hydrolyzed components for each sample. As shown in the MS-TOF results in FIG. 20, percentages of hydrolyzed products are calculated from the peak intensities of each spectrum. According to implementations of experimental data shown in FIG. 20, MS-TOF data of enzymatic hydrolysis of poly-fluorinated cellobiose in solution in FIG. 20A and immobilized on PTFE-like ACG slide in FIG. 20B. The control are the same experimental conditions run without enzymes in (a); (b), (c), and (d) are experimental conditions with the cellulase proteins from *A. niger* (b), *T. reesei* (c), and *T. viride* (d).

These results (FIG. 20) show the rate of hydrolysis on the ACG slide surface versus hydrolysis in solution. The unhydrolyzed cellobiose in solution were 64%, 7%, and 3%, as compared to those of 100%, 69%, and 77% on the ACG slide reacting with the cellulase from *A. niger*, *T. reesei*, and *T. viride*, respectively (Table 2).

TABLE 2

Enzymatic hydrolysis of poly-fluorinated cellobiose 8, the percentage showed hydrolyzed patterns of the reaction in solution/on the ACG slide.

| | Triose | Biose | Glucose | F-tail |
|---|---|---|---|---|
| *A. Niger* | 18/0 | 64/1 | 18/0 | 0/0 |
| *T. Reesei* | 0/0 | 7/69 | 93/25 | 0/7 |
| *T. Viride* | 0/0 | 3/77 | 58/17 | 38/6 |

Figure 21A:
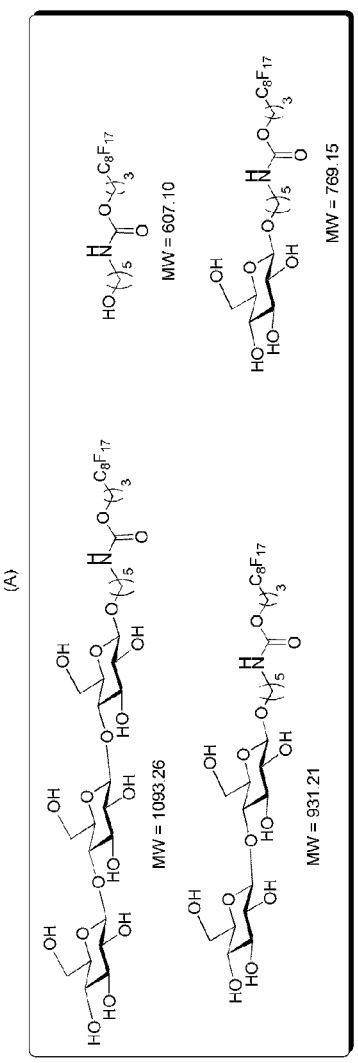
FIG. 21 are chemical structures and graphs of implementations of experimental data showing the effect of celluslases on cellotriose.
Figure 21B:
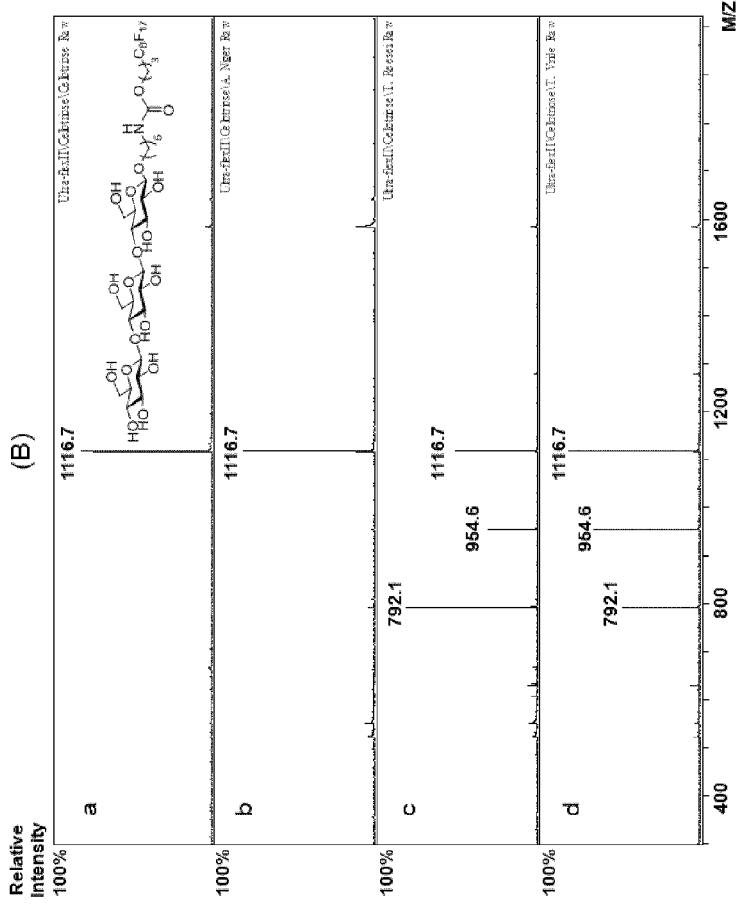

According to implementations of experimental data shown in FIG. 21A, hydrolyzed fragments of cellotriose derivatives remained on the PTFE-like ACG slide surface. FIG. 21A shows the various derivates that are possible, together with their molecular weights. FIG. 21B shows implementations of experimental MS-TOF data of enzymatic hydrolysis of poly-fluorinated cellotriose of the control run without enzymes (a), and with the cellulase proteins from *A. niger* (b), *T. reesei* (c), and *A. viride* (d).

The enzyme from *T. viride* functions the best for cellobiose in solution, and that from *T. reesei* hydrolyzed the disaccharide most effectively among the three enzyme sources on the slide. In solutions, the enzyme from *A. niger* seems to also act as a synthetase that the overall reaction produced 8% of cellotriose (MW 1093) detected as sodium adduct at m/z of 1116.3 [M+Na]+. The enzyme from *A. niger* was characterized as a typical endo-type cellulose which cleaved five glucose units in length at a time. It did not hydrolyze either cellobiose or p-nitrophenyl-β-D-glucoside. To further understand the mode of action, poly-fluorinated (—$C_8F_{17}$) cellotriose 9 (FIG. 14) was subjected to enzymatic hydrolysis in solution.

Using the same analytical procedure, the results (FIG. 21B) indicated that the enzyme from *T. reesei* hydrolyzed the cellotriose substrate most efficiently among the enzymes from three different species. For *A. niger*, the result shown in FIG. 20 and FIG. 21 indicated that this enzyme does not function well in hydrolyzing cellobiose or cellotriose. However, in solution, it hydrolyzed the poly-fluorinated cellobiose 8, and cellotriose 9 with one glucose unit at a time at a very slow reaction rate. Since this commercial enzyme is not pure, this phenomena may be due to the contamination of a small quantity of β-glucosidase in the mixture.

The cellulase from *T. viride* could effectively degrade the newspaper material and *T. reesei* could hydrolyze the crystalline form of cellulose. In general, the enzymatic hydrolysis on the ACG slide surface is more site-specific but much slower than that in solution, as indicated by the data shown in FIG. 20.

Example 12

Cellulase Specificity Studies and Define the Cellulase Type by Using Glycan Array Combined with Mass Spectrometry Cellulases are usually divided into several subclasses of isozymes based upon their function: 1,4-β-glucosidases [EC 3.2.1.74], which cleave cellobiose into individual glucose molecule, exoglucanases (1,4-β-D-glucan cellobiohydrolase [EC 3.2.1.91]), which cleaves cellobiose units from the end of the cellulose chain, and endoglucanases (1,4-β-D-glucan glucanohydrolase [EC 3.2.1.6]), which cleave the chain randomly at internal positions, creating new ends for exoglucanases. HPLC analysis of the products of hydrolysis of MUF-glucosides is often used to determine the hydrolytic specificity of these purified enzymes. From the above results, the devices and methods of this disclosure serve as another platform for studying the specificity of various types of cellulases.

To verify, the exoglucanases (L3) and endoglucanase (44A) were prepared according methods well known in the literature with minor modifications. First, enzymatic hydrolysis reactions were conducted in solution with the purified enzymes using substrates 8, 9 and 10. At the completion of the reaction, the solution mixtures were transferred to the PTFE-like ACG slide, and prepared by using the same washing procedures before being subjected to MS-TOF assay.

Figure 22:
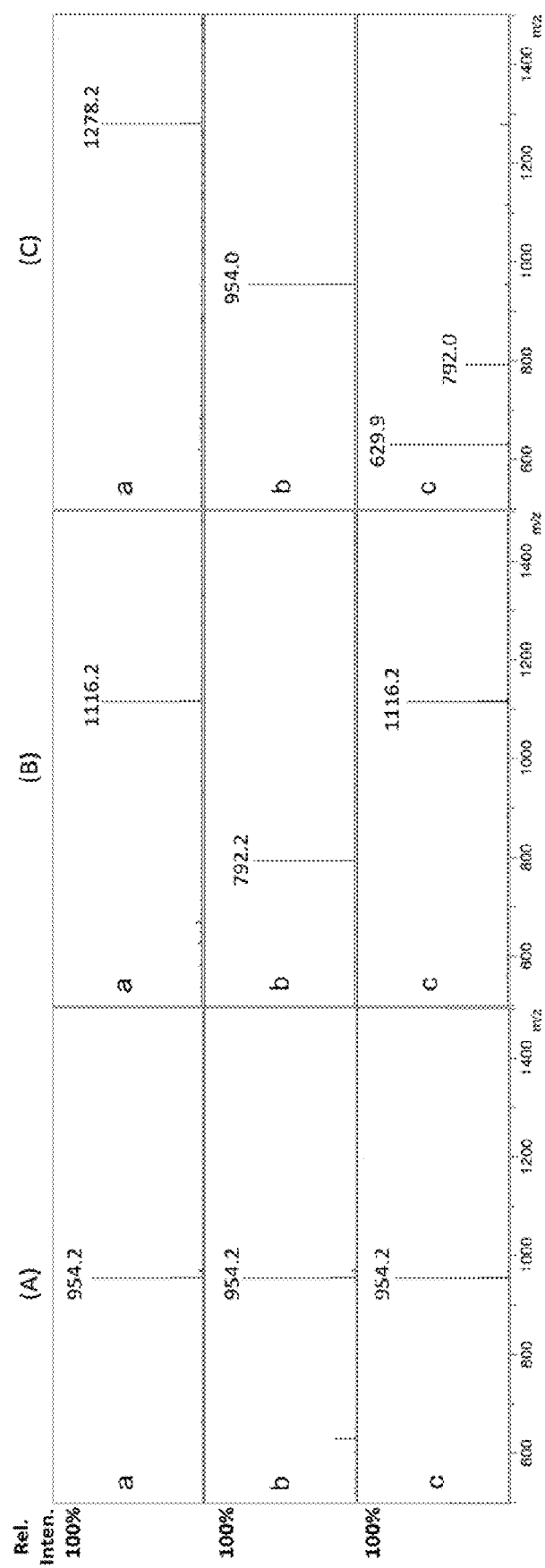
FIG. 22 is a graph of an implementation of experimental MS-TOF data of enzymatic hydrolysis of poly-fluorinated cellobiose (A), poly-fluorinated cellotriose (B) and poly-fluorinated cellotetraose (C) in solution.
Figure 23:
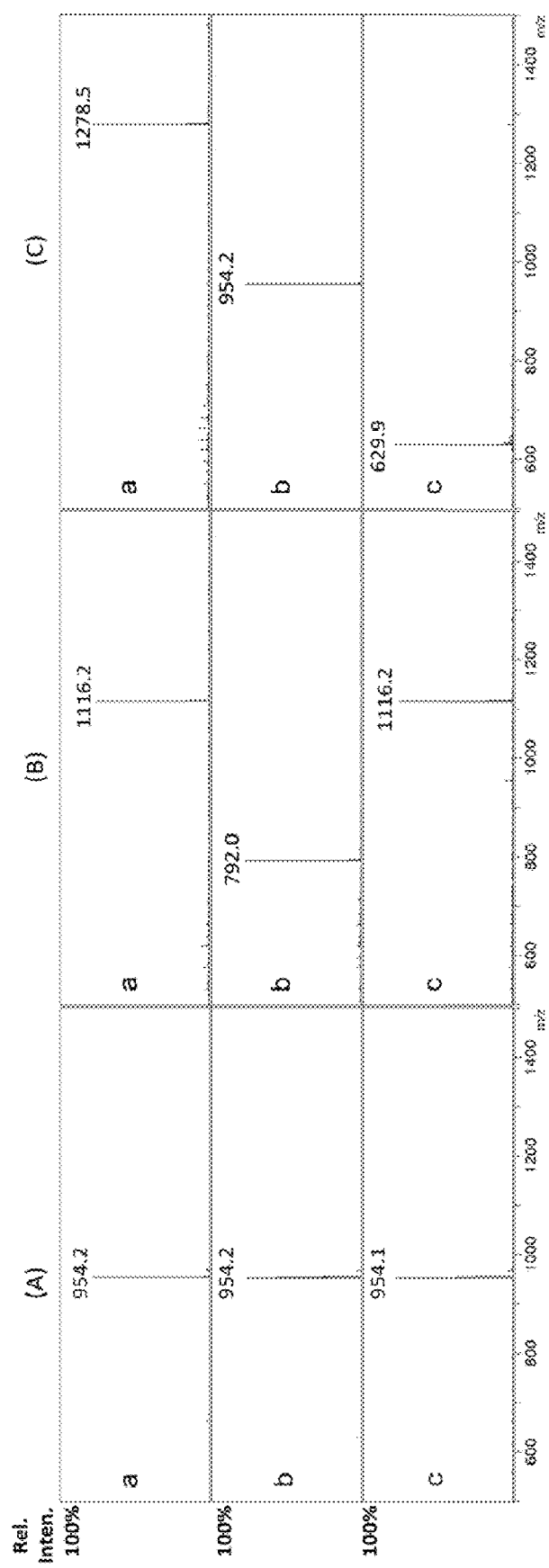
FIG. 23 is a graph of an implementation of experimental MS-TOF data of enzymatic hydrolysis of poly-fluorinated cellobiose (A), poly-fluorinated cellotriose (B) and poly-fluorinated cellotetraose (C) on an ACG glass slide.

FIG. 22 shows MS-TOF data of enzymatic hydrolysis of poly-fluorinated cellobiose (A), poly-fluorinated cellotriose (B) and poly-fluorinated cellotetraose (C) in solution. For each carbohydrate, a specific enzyme was added: (a) is the control run without enzymes, (b) is exoglucanase L3, and (c) is endoglucanase 44A. FIG. 23 shows MS-TOF data of enzymatic hydrolysis of poly-fluorinated cellobiose (A), poly-fluorinated cellotriose (B) and poly-fluorinated cellotetraose (C) on an ACG glass slide. For each carbohydrate, a specific enzyme was added: (a) is the control run without enzymes, (b) is exoglucanase L3, and (c) is endoglucanase 44A.

As shown according to the implementations of experimental data shown in FIG. 22, exoglucanase L3 cleaves cellobiose units slowly from the end of substrate 8 and cleave cellobiose quickly when compound 9 or 10 is the substrate, consistent with the definition of the exoglucanase. Endoglucanase 44A can't accept the cellobiose substrate 8 or cellotriose substrate 9, but cleaves the trisaccharide or tetrasaccharide unit of cellotetraose substrate 10.

Figure 20B:
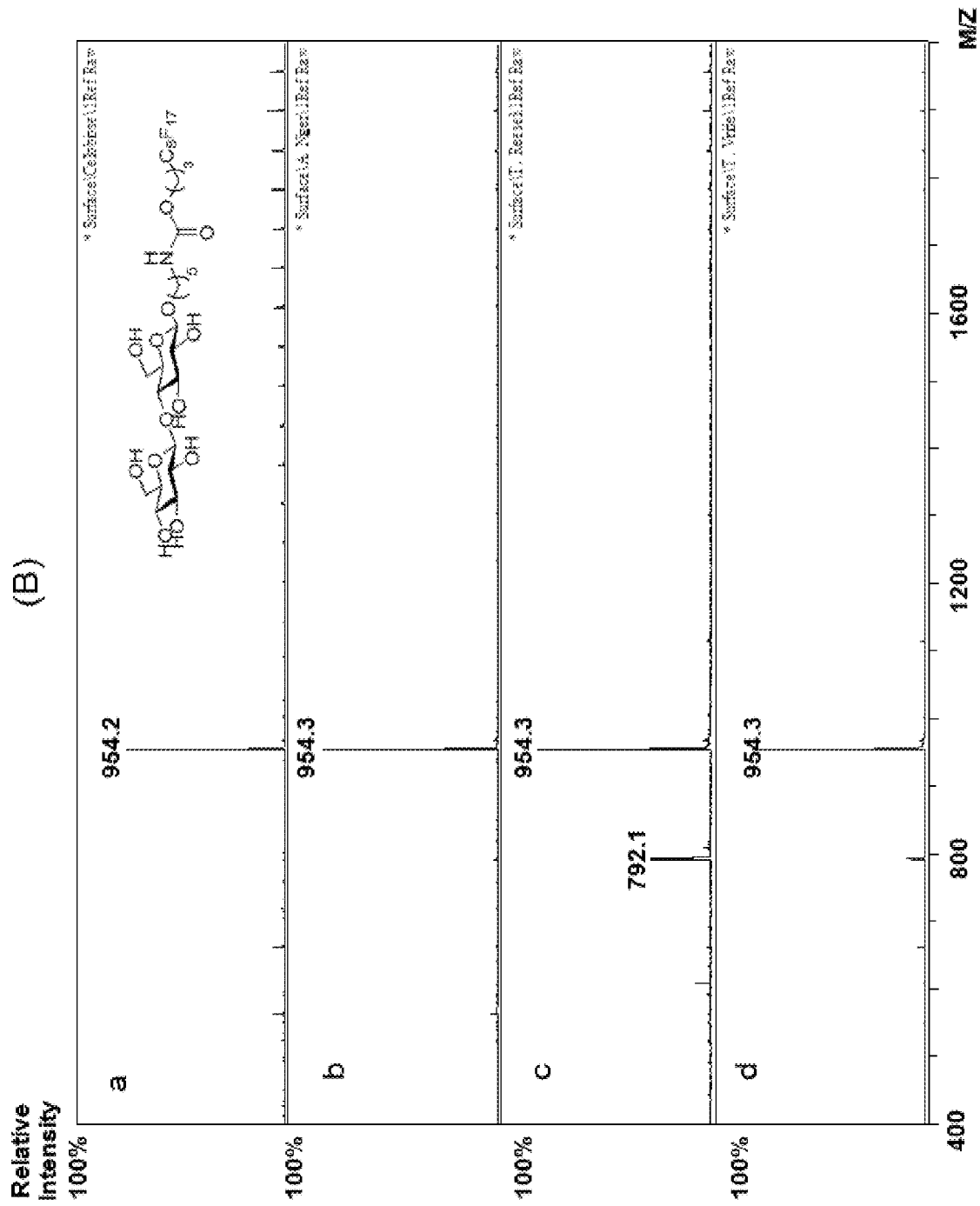

For comparison and as illustrated according to implentations shown in FIG. 23, substrate 8, 9, and 10 were immobilized on the PTFE-like ACG surface and carried out the cellulase hydrolysis on the surface directly, after the same washing procedures, these slides were subjected to MS-TOF assay. As shown in FIG. 20B, exoglucanase L3 only cleaved a fraction of cellobiose substrate 8 after 24 hours of incubation and cleaved the cellobiose quickly when compound 9 or 10 as the substrate. The endoglucanase 44A can't accept compound 8 or 9 as a substrate. However, it cleaved cellotetraose quickly when compound 10 as a substrate. In contrast to the hydrolysis reaction run in solution, endoglucanse 44A cleaved cellotetraose at a time and did not cleave cellotriose when cellotetraose 10 as a substrate. From the above results, the cellotetraose substrate 10 was the best carbohydrate to create array on the PTFE-like ACG surface for the experiments conducted. By using this array, the activity and specificity of unknown cellulase may be examined.

Example 13

Creation of Covalent Bond Glycan Array on PTFE-Like ACG Slides

There are several functionalized glass slides are commercial available for glycan array, for example glass slides coated with: amine, carboxylate, N-hydroxysuccinimide (NHS), avidin, epoxy, aldehyde, chelating nickel group, etc. When creating glycan array on these surfaces, suitable buffer and repeated blocking and washing steps are needed. According to implementations, substrates with a phosphonic acid functional group are easy to chelating on the ACG slide and can tolerate repeated washing steps. Accordingly, a novel method for effective glycan array preparation is hereby disclosed.

Figure 24:
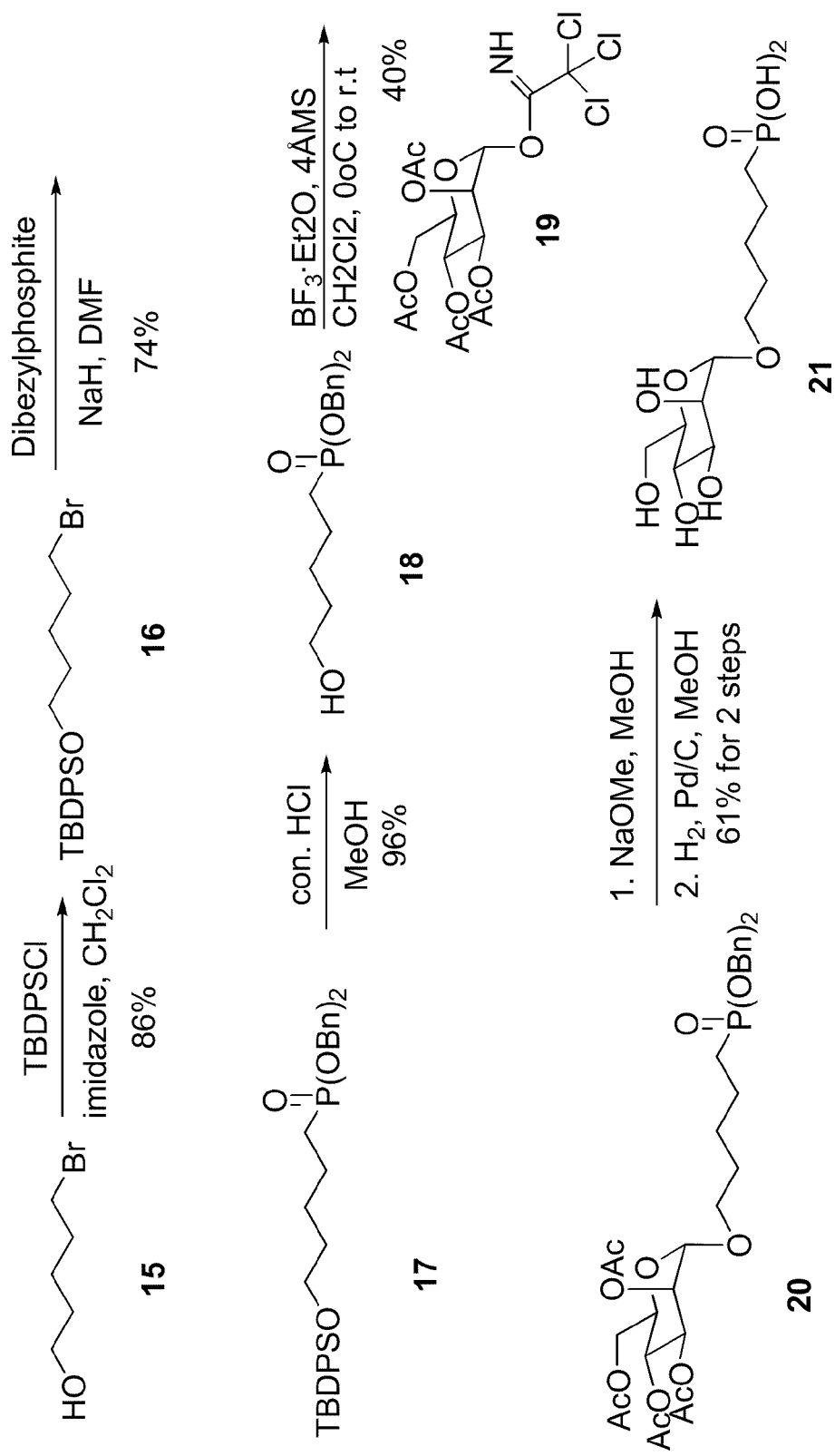
FIG. 24 is a scheme for the synthesis of mannose derivative 21.

Mannose with phosphonic acid compound 21 was synthesized via the scheme illustrated in FIG. 24. Commercial available compound 15 was protected with TBDPS group, and then bromide was changed to phosphonate by using Arbuzov reaction. After desilylation, compound 18 was obtained for the following glycosylation reaction. By using $BF_3 \cdot OEt_2$ as a promoter, compound 19 was used as the sugar donor, which yielded mannose molecule with the phosphonate group derivative 20. After global deprotection, mannose with a phosphonic acid compound 21 was obtained.

Figure 25:
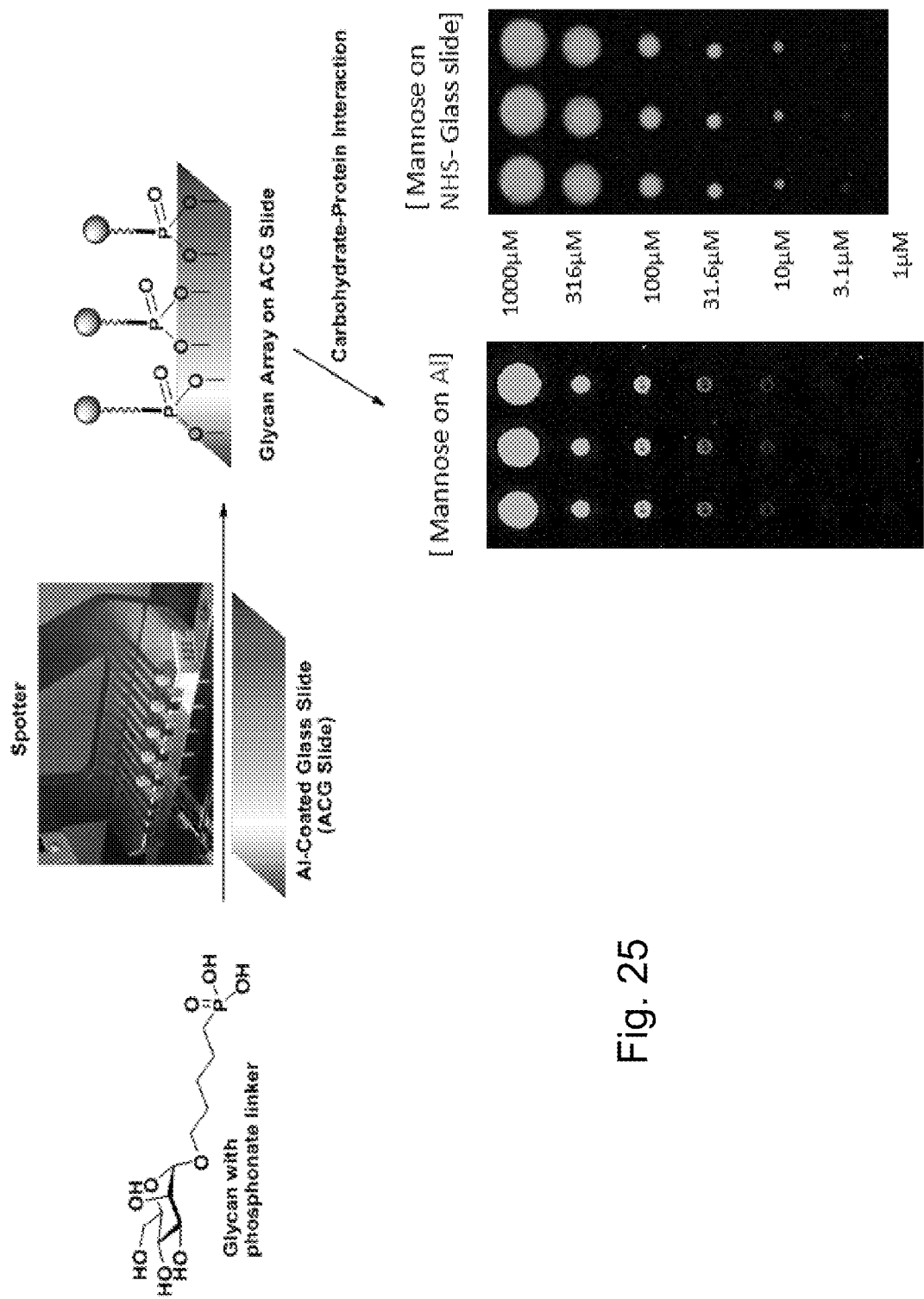
FIG. 25 is a block diagram of an implementations of a method of creation of covalent bonding glycan array on the ACG slide.

Compound 21 was dissolved in methanol. A solution of this sugar derivative was spotted robotically onto the PTFE-like ACG slide surface. After incubation, without blocking, the slides were rinsed repeatedly with distilled water, and used for protein binding analysis by using Alexa 488-labeled Concanavalin A as a protein source. Different incubation times were evaluated and 15 minutes was determined to be enough for the sugar derivative to chelate on the ACG slide. Different concentrations of compound 21 were also spotted on the ACG slide wherein the result was an ACG slide comparable to the NHS coated glass slide, as illustrated in FIG. 25.

Example 14

Materials and Methods

All chemicals and anhydrous solvents were purchased from a commercial source and used without further purification. Molecular Sieves (MS) for glycosylation were AW-300 (Aldrich). FluoroFlash® SPE cartridge was purchased from Sigma. Reactions were monitored with analytical thin-layer chromatography (TLC) in EM silica gel 60 F254 plates and visualized under UV (254 nm) and/or by staining with $KMnO_4$ or p-Anisadehyde. $^1$H NMR spectra were recorded on a Bruker ULTRASHIELD-600 PLUS (600 MHz) spectrometer at 298K. Chemical shifts (in ppm) were assigned according to the internal standard signal of CDCl$_3$ ($\delta$=7.24 ppm). $^{13}$C NMR spectra were obtained with Bruker ULTRASHIELD-600 PLUS spectrometer and were calibrated with CDCl$_3$ ($\delta$=77.00 ppm). Coupling constants (J) are reported in hertz (Hz) Splitting patterns are described by using the following abbreviations: s, singlet; brs, broad singlet, doublet; t, triplet; m, multiplet.

Substrate Materials

Micro glass slides (75.5×25.4×1 mm$^3$) were cleaned in piranha solution, a mixture of concentrated H$_2$SO$_4$ and 30% H$_2$O$_2$ (70:30 v/v), at 120° C. for 30 min, rinsed with plenty of deionized water until pH 7, and purge dried with high-quality nitrogen gas. The high-purity aluminum targets (99.999% pure) were obtained from Summit-Tech Resource Corp. (Hsin-Chu, Taiwan). These raw materials were provided to vendors Cheng-Jen Corp. (Kao-Hsiung, Taiwan) and Yujay-Tech Corp. (Chin-Ju, Taiwan) for the fabrication of ACG slides by using different coating techniques such as magnetron sputtering, cathode arc evaporation, and thermal evaporation. The fabricated ACG slides were either used directly or anodized with a DC current at 20 V (Keithley 2400 Model) at 48 C in 0.3M aqueous oxalic acid for 60-90 s. The surface properties of the fabricated ACG slides are shown in FIG. 1. The surfaces were sputtered with gold and examined by SEM (FEI XL30 SFEG, FEI Company). The surface roughness and thickness of the aluminum coating were measured by AFM (Dimension 3100 Veeco Instruments, Inc.). The surface compositions of these slides were analyzed by XPS by using an Omicron ESCA spectrometer with a monochromatic Al$_{K\alpha}$ X-ray (1486.6 eV) source under ultrahigh vacuum (1×10$^{-10}$ Torr). All spectra were calibrated by the carbon is spectrum at 284.5 eV and the oxygen is spectrum at 532 eV.

Fabrication of NH$_2$-ACG Slides

The ACG slide was washed with acetone and water consecutively on a multishaker (FMS2 FINEPCR) for 2-3 min, purge-dried with high-purity nitrogen gas, and further dried in an oven at 100° C. for 10-15 min. Surface activation was conducted by a plasma cleaner (Harrick PDC 32 G, 200-600 mTorr) with oxygen, argon, or mixed gases at room temperature for 10 min. Immediately after plasma treatment, APDMES (0.8 mL) was placed evenly on the surface (in bulk), which was covered with a sealed petri dish and heated directly on a hot plate at 658 C for 40 min1 h. When the reaction was completed, the sample slide was rinsed thoroughly, sonicated in methanol for 3 min (20% power), and purge-dried with high-purity nitrogen gas. The surface with aminosilane-grafted substrate was used for amide-linkage formation in situ with the mannose derivative compound 27 and HBTU. The commercial NH$_2$ glass slides (#40004 from Corning Inc.) were used for comparison of protein binding.

Fabrication of NHS-ACG Slides

ACG slides coated by thermal evaporation were further anodized in 0.2M oxalic acid for 90 s, rinsed with deionized water, and activated by argon plasma as usual. Without any contamination, the slide was assembled in a designed PTFE sealed, heat-transferable reaction cell, and APTES (1 mL, bulk) was immediately added to the cell. The PTFE cell was covered with a glass plate. Under moisture-free conditions, the cell was heated at 658 C for 30 min and rinsed thoroughly with methylene chloride and methanol. The slides were then purge-dried with nitrogen gas. Beforehand, a saturated solution of DSS (0.5 g; CAS #68528-80-30) in DMF (4 mL) and diisopropylethylamine (220 mL) was prepared. A portion (1.33 mL) of this saturated solution was added to each reaction cell. The NHS-ACG slide was formed within 3 h with constant swirling at room temperature. The slide was rinsed thoroughly with ethyl acetate and purge-dried with high-quality nitrogen gas. After the PTFE cell was dried and disassembled, the slide was ready for Globo H-NH$_2$ microarray.

ACG Slides Preparation—Fabrication of the Silane Based PTFE-Like ACG Slides

In a moisture-free condition, the argon plasma activated ACG slide was reacted with 3-aminopropyltriethylsilane in bulk at 65° C. for 30 minutes then washed with methylene chloride thoroughly and dried by nitrogen gas under atmospheric condition. The silanated ACG slide was immersed in a solvent mixture (DMF/IPA/DIPEA 12/6/1 volume ratio) of N-succinimidyl 3-perfluorooctylpropionate (0.05 wt %) solution for two hours at room temperature. After the reaction, the slide was rinsed with IPA thoroughly, and purged dried with nitrogen gas. Water contact angle ($\geq$115°) measurement was quickly checked for the completion of the slide fabrication.

ACG Slides Preparation—Fabrication of the Phosphonic Acid Based PTFE-Like ACG Slides.

The aluminum coated glass slide was washed by acetone and water for three times, and then dried by dry clean air. The clean slide was then activated and cleaned by oxygen plasma (Harrick plasma, PDC-32G) for 15 mins. After activation, the slide was immersed into 3,3,4,4,5,5,6,6,7,7,8,8,9,9,10,10,10-heptadecafluorodecylphosphonic acid (HDFDPA) 3 solution (1M, 65% 2-propanol in H$_2$O, pH=6.17) immediately. The solution was vibrated by gentle sonication (50 W) for 15 mins. Following the ultrasonic treatment, the slide was removed from the solution and then immersed into another pure 2-propanol solution for 15 mins. The solution was also sonicated to assist the removal of excess phosphonic acid on the slide surface. The slide was dried by dry nitrogen and reduced pressure. Upon the completion of the reaction, the slide was washed thoroughly with IPA, and nitrogen purge dried. Water contact angle ($\geq$115°) measurement was quickly checked for the completion of the slide fabrication.

Reference-Controlled NHS—Glass Slides

NHS-glass slides (from SCHOTF, North America) were used directly. The NH$_2$-glass slide (#40004 from Corning, Inc.) was modified by using the same preparation method for the NHS-ACG slide. The slide was assembled in a designed PTFE sealed, heat-transferable reaction cell. A portion (1.33 mL) of saturated DSS solution was added for reaction with the NH$_2$-glass surface. After constant swirling at room temperature for 3 h, the slide was rinsed thoroughly with ethyl acetate and purge-dried with high-quality nitrogen gas. After the PTFE cell was dried and disassembled, the slides were ready for Globo H—NH$_2$ microarray.

Chemical Materials

All chemicals employed in the synthesis of 6 were purchased from Aldrich or the specified individual chemical companies and used without any further purification.

Synthesis

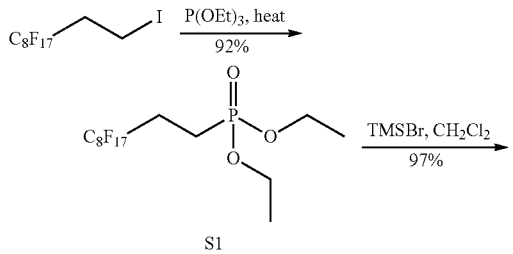

S1

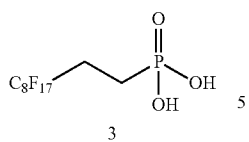

3

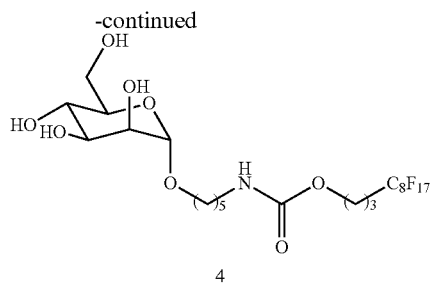

4

Preparation of 3.

Diethyl 3,3,4,4,5,5,6,6,7,7,8,8,9,9,10,10,10-heptadecafluorodecylphosphonate (S1): 1,1,1,2,2,3,3,4,4,5,5,6,6,7,7,8,8-heptadecafluoro-10-iododecane (1.02 g, 1.78 mmol) and P(OEt)$_3$ (15 ml, excess) was added to 50 ml round bottom flask. The mixture was heated to 120° C. under nitrogen for 40 hours and then purified with FluoroFlash® SPE cartridge. The remaining light yellow oil was chromatographed with Ethyl Acetate/Hexane to give product. (0.96 g, 92%). $^1$H NMR (600 MHz, CDCl$_3$): δ (ppm) 4.10-4.00(m, 4H, CH$_2$CH$_3$), 2.35-2.23 (m, 2H, CH$_2$CF$_2$), 1.92-1.86 (m, 2H, PCH$_2$), 1.25 (t, J=7.2 Hz, 6H, CH$_2$CH$_3$). $^{13}$C NMR (150 MHz, CDCl$_3$): δ (ppm) 121-106 (m, C—F coupling unsolved), 62.28 (d, $^2J_{cp}$=6 Hz, CH$_2$CH$_3$), 25.33 (t, $^2J_{cF}$=23 Hz, CH$_2$CF$_2$), 17.24 (d, $^2J_{cp}$=148 Hz, PCH$_2$), 16.38, $^3J_{cp}$=6 Hz, CH$_2$CH$_3$), HRMS calcd for C$_{14}$H$_{14}$F$_{17}$O$_3$P: [M+H]$^+$, 585.0487; found: 585.0433

3,3,4,4,5,5,6,6,7,7,8,8,9,9,10,10,10-heptadecafluorodecylphosphonic acid (3): Bromotrimethylsilane (0.74 mL, 5.75 mmol) was added via syringe to a solution of Si (1.12 g, 1.92 mmol) in anhydrous CH$_2$Cl$_2$ (15 ml) under nitrogen. The mixture was stirred for 30 hours. Volatiles were removed in vacuo completely to give white powder. The white powder can be used for next experiment directly without further purification. (0.99 g, 97%). $^1$H NMR (600 MHz, MeOD): δ (ppm) 2.48-2.42 (m, 2H, CH$_2$CF$_2$), 1.99-1.96 (m, 2H, PCH$_2$). $^{13}$C NMR (150 MHz, MeOD): δ (ppm) 121-106 (m, C—F coupling unsolved), 25.55 (t, $^2J_{cF}$=23 Hz, CH$_2$CF$_2$), 18.26 (d, $^2J_{cp}$=143 Hz, PCH$_2$). HRMS calcd for C$_{10}$H$_5$F$_{17}$O$_3$P: [M−H]$^−$, 526.9699; found: 526.9669

Preparation of Polyfluorinated Mannose 4.

2,5-dioxopyrrolidin-1-yl 4,4,5,5,6,6,7,7,8,8,9,9,10,10,11,11,11-heptadecafluoro-undecyl carbonate (S2): To a stirred solution of 4,4,5,5,6,6,7,7,8,8,9,9,10,10,11,11,11-heptadecafluoroundecan-1-ol (214 mg, 0.45 mmol) and DSC (184 mg, 0.72 mmol) in acetonitrile was added triethylamine (0.5 ml, 3.60 mmol) at 0° C under nitrogen and then the solution warmed up slowly to room temperature and stirred for 16 hours. The reaction was washed with H$_2$O three times. The organic layer was dried over Na$_2$SO$_4$, filtered and concentrated under reduced pressure. The product was purified by flash chromatography to give white solid. (242 mg, 87%). $^1$H NMR (600 MHz, CDCl$_3$): δ (ppm) 4.40 (t, 2H, J=6.3 Hz, CH$_2$O), 2.83 (s, 4H), 2.27-2.18 (m, 2H, CH$_2$CH$_2$F), 2.10-2.05 (m, 2H, FCH$_2$). $^{13}$C NMR (150 Mhz, CDCl$_3$): δ (ppm) 168.73 (NCO), 151.65 (OCO), 121-106 (m, C—F coupling unsolved), 69.87 (OCH$_2$), 25.66 (FCH$_2$), 20.12(FCH$_2$CH$_2$)

[(4,4,5,5,6,6,7,7,8,8,9,9,10,10,11,11,12,12,12-nonadecafluorododecoxycarbonyl-amino)pentyl] α-D-mannopyranoside (4): To a stirred solution of S2 (250 mg, 0.40 mmol) and 5-Aminopentyl α-D-manno-pyranoside (112 mg, 0.39 mmol) in CH$_2$Cl$_2$ was added triethylamine (0.2 mL) at 0° C. under nitrogen and then the ice bath was removed. The reaction warmed up to room temperature and stirred overnight. The solvent was removed in vacuo and the product was purified by FluoroFlash® SPE cartridge and flash chromatography to give white solid. (253 mg, 83%). 1H NMR (600 MHz, CDCl$_3$): δ (ppm) 7.97 (s, 1H, NH), 4.72 (d, J=1.6 Hz, 1H, 1-H of Man), 4.10 (t, J=6.2 Hz, 2H, O—CH$_2$), 3.82-3.80 (m, 1H), 3.77-3.76 (m, 1H), 3.73-3.70 (m, 2H), 3.69-3.66 (m, 1H), 3.59 (t, J=9.6 Hz, 1H), 3.52-3.49 (m, 1H), 3.42-3.38 (m, 1H), 3.08 (t, J=7.1 Hz, 1H, O—CH$_2$), 2.32-2.23 (m, 2H, CH$_2$CH$_2$F), 1.94-1.89 (m, 2H, FCH$_2$), 1.63-1.54 (m, 2H), 1.51-1.46 (m, 2H), 1.42-1.32 (m, 4H), $^{13}$C NMR (150 MHz, CDCl$_3$): δ (ppm) 157.44 (NCO), 120-105 (m, C—F coupling unsolved), 100.12 (1-C of Man), 73.19, 71.25, 70.87, 67.22, 67.04, 62.80, 61.51, 40.27 (CH$_2$N), 29.41, 19.10, 26.20, 25.63, 24.86, 20.07. HRMS calcd for C$_{23}$H$_{28}$F$_{17}$NO$_8$: [M+Na]$^+$, 806.1598; found: 806.1643.

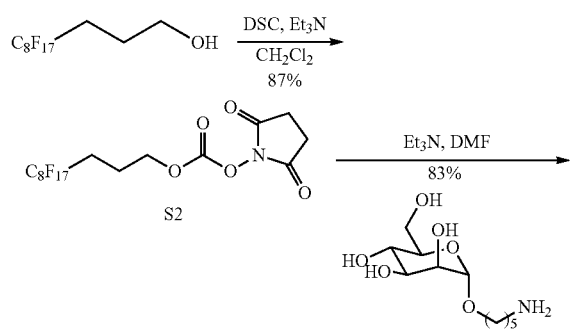

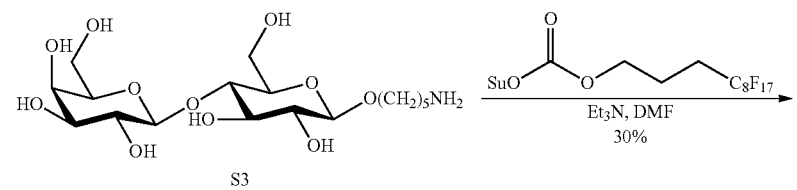

S3

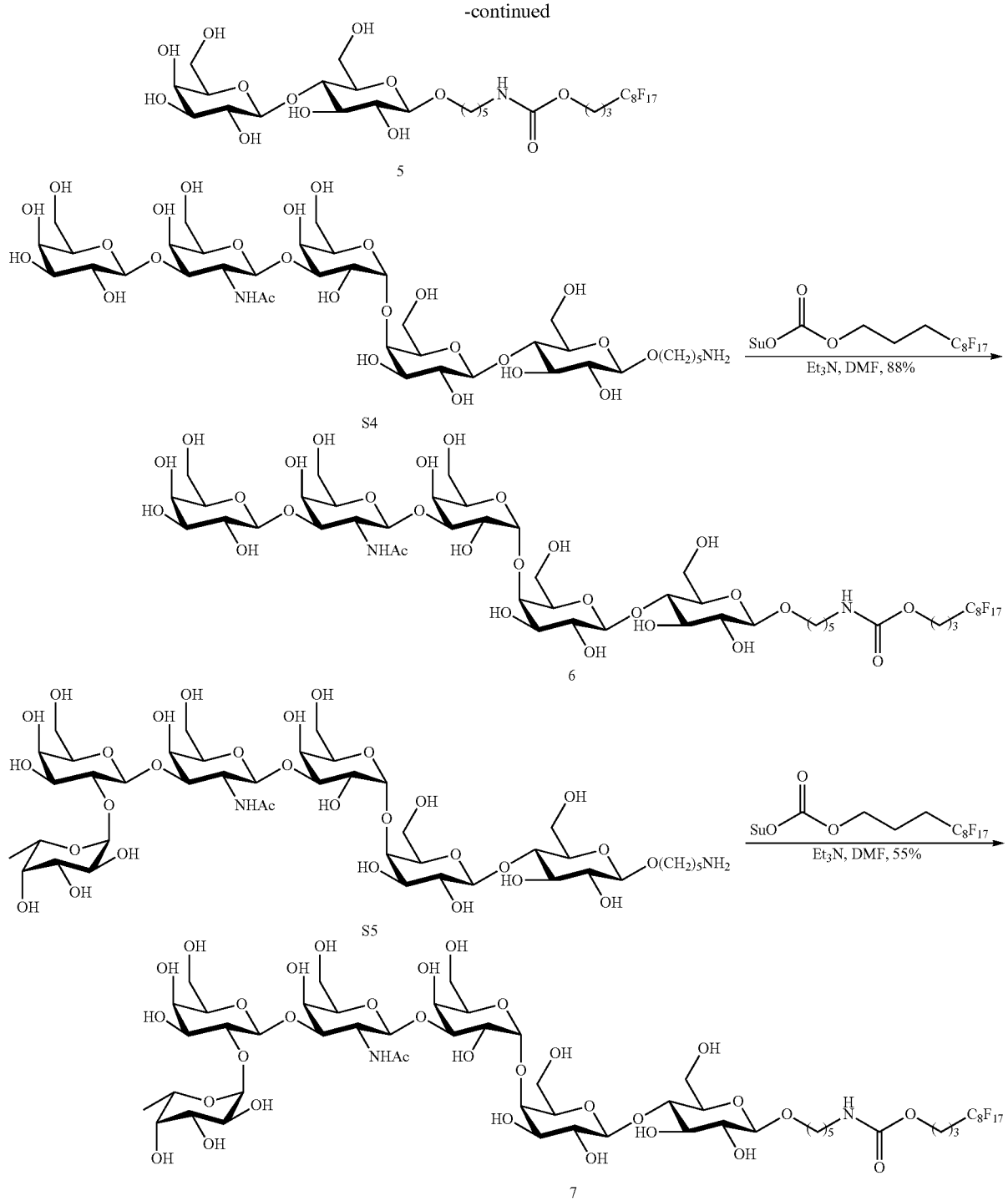

Synthesis of Polyfluorinated 5, 6, and 7.

[(4,4,5,5,6,6,7,7,8,8,9,9,10,10,11,11,12,12,12-nonadecaflourododecoxycarbonyl-amino)pentyl] β-$_D$-lactoside (5): The solution of S3 (44 mg, 0.10 mmol) and S2 (76 mg, 0.12 mmol) in DMF (5 mL) was added Et$_3$N (28 μL, 0.20 mmol) at 0° C. After stirring at room temperature overnight, the reaction mixture was concentrated in vacuo and purified by column chromatography and FluoroFlash® SPE cartridge to give 5 as white foamy solid (29 mg, 30%). Rf: 0.68 (EtOAc:MeOH=5:1). $^1$H NMR (600 MHz, MeOD): δ 4.36 (d, J=$_{7,6}$ Hz, 1H), 4.27 (d, J=7.8 Hz, 1H), 4.15 (bt, 1H), 4.10 (t, J=6.0 Hz, 2H), 3.90-3.40 (m, 12H), 3.39 (m, 1H), 3.25 (t, J=8.1 Hz, 1H), 3.09 (t, J=6.9 Hz, 2H), 2.31-2.26 (m, 2H), 1.93-1.90 (m, 2H), 1.64-1.62 (m, 2H), 1.52-1.49 (m, 2H), 1.42-1.40 (m, 2H). $^{13}$C NMR (150 MHz, MeOD): δ 157.53, 120.62-110.33 (m, C—F coupling unresolved), 103.79, 102.93, 79.38, 75.79, 75.16, 75.13, 73.52, 73.46, 71.26, 69.38, 69.00, 62.90, 61.19, 60.62, 40.36, 29.29, 29.05, 27.33 (t), 22.96, 20.18. MS (ESI) Calcd for C$_{29}$H$_{38}$F$_{17}$NO$_{13}$Na+: 954.1970 [M+Na]$^+$; found: 954-1964.

[(4,4,5,5,6,6,7,7,8,8,9,9,10,10,11,11,12,12,12-nonadecafluorododecoxycarbonyl-amino)pentyl] β-D-galactopyranosyl-(1→3)-2-acetamido-2-deoxy-β-D-galactopyra-nosyl-(1→3)-α-D-galactopyranosyl-(1→4)-β-D-galactopyranosyl-(1→4)-β-D-gluco-pyranoside (6): Compound 6 was prepared from compound S4 according to the procedure as described for 5 in 55% yields after purification by column chromatography and FluoroFlash® SPE cartridge. $R_f$: 0.18 (EtOAc:MeOH=1:1). White foamy solid. $^1$H NMR (600 MHz, MeOD): δ 4.72 (d, J=8.4 Hz, 1H), 4.44 (d, J=7.0 Hz, 1H), 4.37 (d, J=7.4 Hz, 1H), 4.31 (d, J=7.7 Hz, 1H), 4.29 (m, 1H), 4.19 (d, J=2.1 Hz, 1H), 4.13 (t, d, J=6.0 Hz, 2H), 4.09 (m, 1H), 4.01 (bs, 1H), 3.95-3.67 (m, 20H), 3.60-3.42 (m, 11H), 3.26 (t, J=8.6 Hz, 1H), 3.12 (t, J=7.0 Hz, 2H), 2.34-2.26 (m, 2H), 2.01 (s, 3H), 1.98-1.91 (m, 2H), 1.69-1.64 (m, 2H), 1.55-1.52 (m, 2H), 1.46-1.43 (m, 2H). $^{13}$C NMR (150 MHz, MeOD): δ 173.69, 157.44, 120.11-108.43 (m, C—F coupling unresolved), 105.22, 104.06, 102.91, 102.80, 101.38, 80.11, 79.83, 79.34, 78.55, 75.38, 75.11, 75.05, 74.97, 74.94, 73.46, 73.24, 73.17, 71.17, 71.07, 71.00, 69.31, 69.21, 68.87, 68.14, 68.07, 62.81, 61.21, 60.50, 60.16, 51.98, 40.26, 29.22, 28.97, 22.87, 21.95, 20.08, 19.47. MS (MALDI) Calcd for $C_{49}H_{71}F_{17}N_2O_{28}Na^+$: 1481.382 [M+Na]$^+$; found: 1481.452.

[(4,4,5,5,6,6,7,7,8,8,9,9,10,10,11,11,12,12,12-nonadecafluorododecoxycarbonyl-amino)pentyl] α-L-fucopyranosyl-(1→2)-β-D-galactopyranosyl-(1→3)-2-acetamido-2-deoxy-β-D-galactopyranosyl-(1→3)-β-D-galactopyranosyl-(1→4)-β-D-galactopyranosyl-(1→4)-β-D-glucopyranoside (7): Compound 7 was prepared from compound S5 according to the procedure as described for 5 in 88% yields after purification by column chromatography and FluoroFlash® SPE cartridge. $R_f$: 0.18 (EtOAc:MeOH=1:1). White foamy solid. $^1$H NMR (600 MHz, MeOD): δ 5.26 (d, J=3.8 Hz, 1H), 4.96 (d, J=3.8 Hz, 1H), 4.58 (d, J=7.9 Hz, 1H), 4.44 (d, J=7.0 Hz, 1H), 4.30 (d, J=7.6 Hz, 1H), 4.29 (m, 1H), 4.17-4.10 (m, 5H), 4.01 (bs, 1H), 3.93-3.69 (m, 24H), 3.68-3.53 (m, 8H), 3.44-3.41 (m, 1H), 3.26 (t, J=8.6 Hz, 1H), 3.12 (t, J=7.0 Hz, 2H), 2.32-2.28 (m, 2H), 2.04 (s, 3H), 1.97-1.93 (m, 2H), 1.69-1.64 (m, 2H), 1.56-1.52 (m, 2H), 1.47-1.42 (m, 2H), 1.27 (d, J=6.5 Hz, 3H). $^{13}$C NMR (150 MHz, MeOD): δ 173.17, 157.55, 104.20, 104.07, 102.93, 102.59, 101.54, 99.78, 80.05, 79.26, 78.81, 77.83, 76.82, 75.50, 75.21, 75.09, 74.23, 73.56, 73.41, 72.25, 71.33, 71.22, 70.25, 69.41, 69.32, 69.09, 68.37, 68.33, 66.83, 62.91, 61.31, 61.26, 60.65, 60.25, 51.82, 40.37, 29.32, 29.07, 22.97, 22.18, 20.19, 15.40. MS (MALDI) Calcd for $C_{55}H_{81}F_{17}N_2O_{32}Na^+$: 1627.440 [M+Na]+; found: 1627.526.

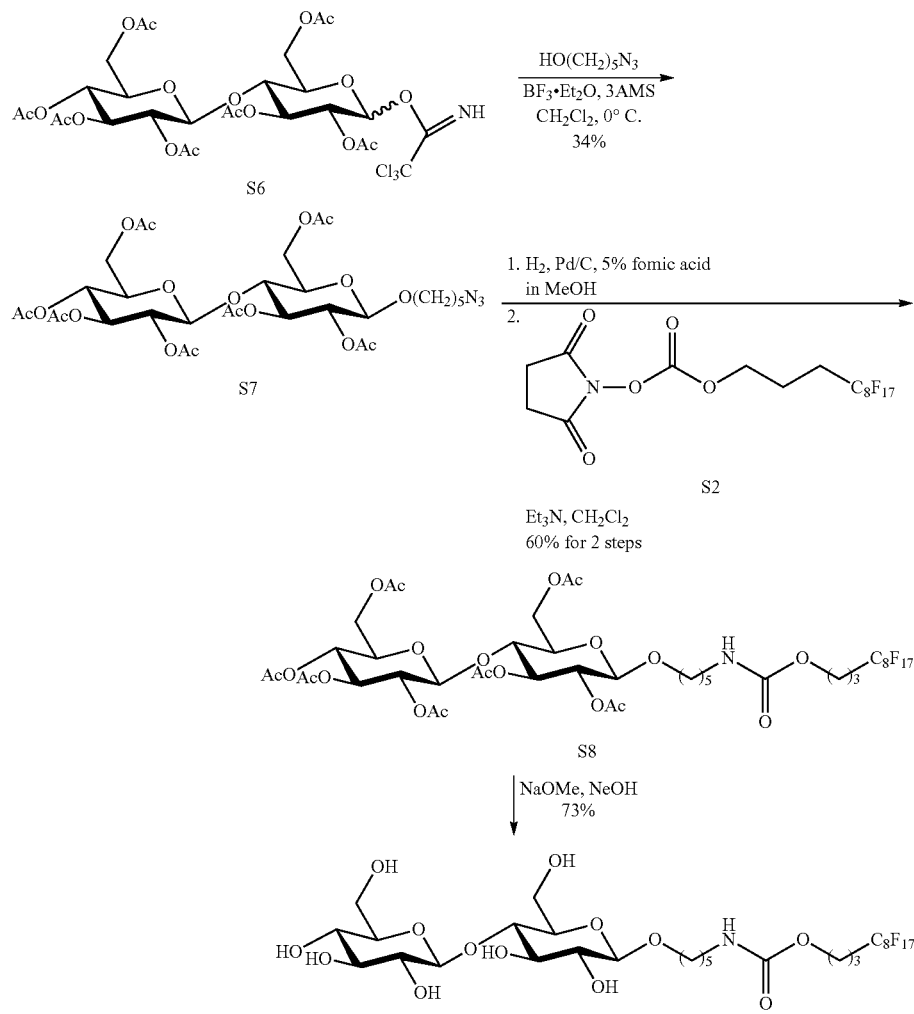

Synthesis of Polyflouro-Cellobioside 8

5-Azidopentyl 2,3,6,2',3',4',6'-hepta-O-acetyl-β-D-cellobioside (S7): A suspension of the compound S6 (1.01 g, 1.29 mmol), s-azido-1-pentanol (0.84 g, 6.47 mmol), and 3 Å molecular sieves in CH$_2$Cl$_2$ (10 mL) was stirred at room temperature for 1 h. The reaction mixture was cooled to 0° C. and treated dropwise with BF$_3$.Et$_2$O (33 μL, 0.26 mmol). After stirring at 0° C. for 2h, saturated aqueous NaHCO$_3$ was added and the reaction mixture was filtered with Celite. The mixture was diluted with CH$_2$Cl$_2$ and then washed with brine. The organic phase was dried over Na$_2$SO$_4$ and evaporated the solvent and purified by chromatography (Hexane:EtOAc=3: 1→2:1→1:1) to give S7 as a white foamy solid (330 mg, 34%). R$_f$: 0.48 (Hexane:EtOAc=1:1). $^1$H NMR (600 MHz, CDCl$_3$): δ 5.16 (t, J=9.4 Hz, 1H), 5.13 (t, J=9.4 Hz, 1H), 5.04 (t, J=9.7 Hz, 1H), 4.91-4.85 (m, 2H), 4.50-4.47 (m, 2H), 4.42 (d, J=8.2 Hz, 1H), 4.34 (dd, J=12.5, 4.3 Hz, 1H), 4.06 (dd, J=12.0, 4.7 Hz, 1H), 4.01 (dd, J=12.3, 1.9 Hz, 1H), 3.81 (m, 1H), 3.74 (t, J=9.5 Hz, 1H), 3.64-3.62 (m, 1H), 3.56 (m, 1H), 3.43 (m, 1H), 3.23 (t, J=6.8 Hz, 2H), 2.10 (s, 3H), 2.06 (s, 3H), 2.01 (s, 3H), 2.00 (s, 3H), 1.99 (s, 3H), 1.98 (s, 3H), 1.96 (s, 3H), 1.59-1.54 (m, 4H), 1.40-1.35 (m, 2H). $^{13}$CNMR (150 MHz, CDCl$_3$): δ 170.54, 170.34, 170.26, 169.86, 169.60, 169.34, 169.08, 100.81, 100.64, 76.51, 72.94, 72.67, 72.49, 71.96, 71.61, 71.56, 69.73, 67.76, 61.84, 61.54, 51.33, 28.94, 28.52, 23.14, 21.08, 20.90, 20.69, 20.57. HRMS (ESI) Calcd for C$_{31}$H$_{45}$N$_3$O$_{18}$Na$^+$: 770.2590 [M+Na]$^+$; found: 770.2570

[(4,4,5,5,6,6,7,7,8,8,9,9,10,10,11,11,12,12,12-nonadecafluorododecoxycarbonyl-amino)pentyl] 2,3,6,2',3',4',6'-hepta-O-acetyl-β-D-cellobioside (S8): A suspension of S7 (50 mg, 0.07 mmol), catalytic amount of Pd/C in 5% formic acid in MeOH (5 mL) was stirred under H$_2$ balloon for 2 h. After filtration through Celite, the filter cake was washed with MeOH. The filtrate was evaporated and co-evaporated with toluene. The residue underwent to next step without purification.

The residue described above was dissolved in CH$_2$Cl$_2$ (5 mL) and then Compound S2 (50 mg, 0.08 mmol) was added. The mixture was cooled to 0° C. Triethylamine (19 μL, 0.13 mmol) was added and the solution continued stirring at room temperature for 12 h. The reaction mixture was concentrated and purified by chromatography (Hexane:EtOAc=1:1) to give S8 as a white foamy solid (49 mg, 60% in two steps). $^1$H NMR (600 MHz, CDCl$_3$): δ 5.14 (t, J=9.5 Hz, 1H), 5.11 (t, J=9.5 Hz, 1H), 5.03 (t, J=,9.5 Hz, 1H), 4.91-4.84 (m, 2H), 4.76 (br, 1H), 4.50 (dd, J=12.0, 1.7 Hz, 1H), 4.48 (d, J=7.9 Hz, 1H), 4.40 (d, J=8.0 Hz, 1H), 4.34 (dd, J=12.5, 4.3 Hz, 1H), 4.09 (t, J=6.1 Hz, 2H), 4.05 (dd, J=12.0, 4.9 Hz, 1H), 4.01 (dd, J=12.5, 2.2 Hz, 1H), 3.80 (m, 1H), 3.73 (t, J=9.5 Hz, 1H), 3.64-3.61 (m, 1H), 3.55-3.53 (m, 1H), 3.43 (m, 1H), 3.12 (m, 2H), 2.18-2.13 (m, 2H), 2.09 (s, 3H), 2.05 (s, 3H), 2.00 (2xs, 6H), 1.98 (s, 3H), 1.97 (s, 3H), 1.95 (s, 3H), 1.92-1.88 (m, 2H), 1.56-1.52 (m, 2H), 1.49-1.44 (m, 2H), 1.34-1.29 (m, 2H). $^{13}$C NMR (150 MHz, CDCl$_3$): δ 170.51, 170.35, 170.25, 169.84, 169.62, 169.33, 169.06, 156.25, 120.18-108.01 (m, C—F coupling unresolved), 100.78, 100.62, 76.47, 72.91, 72.68, 72.45, 71.94, 71.60, 71.56, 69.77, 67.74, 63.17, 61.76, 61.52, 40.83, 29.68, 29.49, 28.92, 27.99, 27.84, 27.69, 23.02, 21.03, 20.84, 20.64, 20.53, 20.33. HRMS (ESI) Calcd for C$_{43}$H$_{52}$F$_{17}$NO$_{20}$Na$^+$: 1248.2703 [M+Na]$^+$; found: 1248.2675

[(4,4,5,5,6,6,7,7,8,8,9,9,10,10,11,11,12,12,12-nonadecafluorododecoxycarbonyl-amino)pentyl] β-D-cellobioside (8): The solution of S8 (222 mg, 0.18 mmol) and NaOMe (50 mg, 0.09 mmol) in MeOH (7 mL) was stirred at room temperature overnight. The mixture was neutralized with Amberlyst-15 ion-exchange resign for 5 min and filtered through a sintered funnel packed with Celite. The filter pad was rinsed with methanol after filtration. The combined filtrates were concentrated under reduced pressure and then purified by flash column chromatography (EtOAc:MeOH=10:1→8:1) to give 8 as a white solid (123 mg, 73%). R$_f$: 0.47 (EtOAc:MeOH=5: 1). $^1$H NMR (600 MHz, MeOD): δ 4.40 (d, J=7.9 Hz, 1H), 4.27 (d, J=7.8 Hz, 1H), 4.10 (t, J=6.1 Hz, 2H), 3.89-3.86 (m, 4H), 3.65 (dd, J=11.8, 5.7 Hz, 1H), 3.57-3.53 (m, 2H), 3.50 (t, J=9.0 Hz, 1H), 3.39-3.32 (m, 3H), 3.30 (m,1H), 3.22 (m, 2H), 3.09 (t, J=6.7 Hz, 2H), 2.32-2.23 (m, 2H), 1.94-1.89 (m, 2H), 1.66-1.61 (m, 2H), 1.53-1.48 (m, 2H), 1.43-1.38 (m, 2H). $^{13}$C NMR (150 MHz, MeOD): δ 157.51, 120.11-108.43 (m, C—F coupling unresolved), 103.20, 102.79, 79.31, 76.69, 76.43, 75.03, 73.47, 69.95, 69.29, 61.00, 60.74, 60.42, 40.32, 29.52, 28.95, 27.36, 27.21, 27.07, 22.86, 20.07. HRMS (ESI) Calcd for C$_{29}$H$_{38}$F$_{17}$NO$_{13}$Na$^+$: 954.1964 [M+Na]$^+$; found: 954.1966.

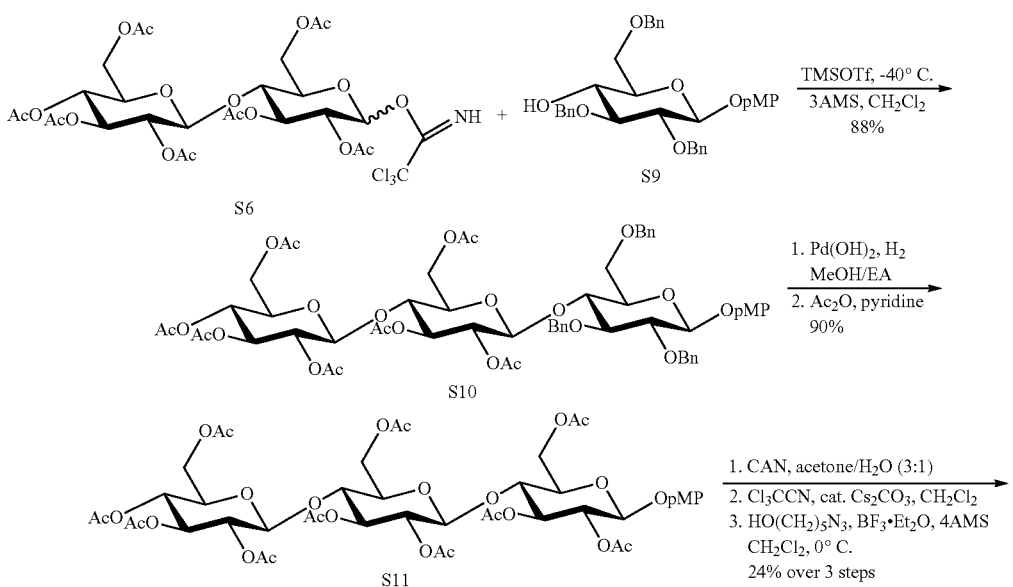

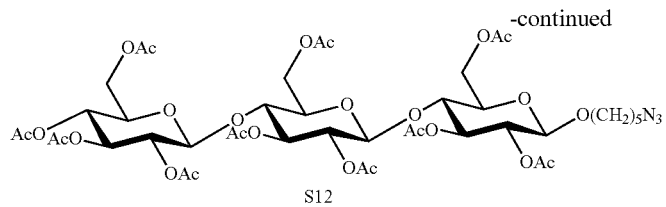

-continued

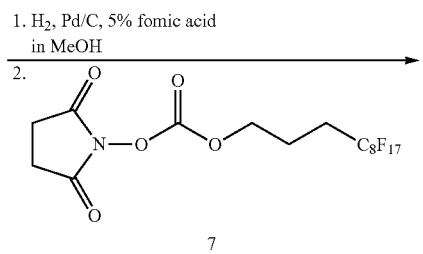

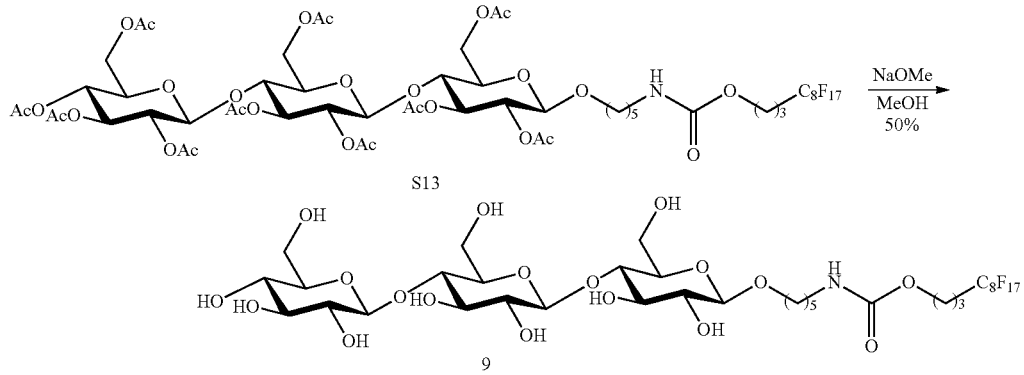

Synthesis of Polyflouro-Cellotrioside 9 para-Methoxyphenyl 2,3,4,6-tetra-O-acetyl-β-D-glucopyranosyl-(1→4)-2,3,6-tri-O-acetyl-β-D-glucopyranosyl-(1→4)-2,3,6-tri-O-benzyl-β-D-glucopyranoside (S10): According to similar procedures reported by Vesalla, a suspension of S6 (1.68 g, 2.16 mmol), S9 (1.0 g, 1.8 mmol) and 3 Å mol. sieves in CH$_2$Cl$_2$ (20 mL) was stirred at room temperature for 1 h. The reaction mixture was cooled to −40° C. and treated dropwise with TMSOTf (98 µl, 0.54 mmol). After stirring at −40° C. for 2 h, saturated aqueous NaHCO$_3$ was added and the reaction mixture was filtered with Celite. The mixture was diluted with CH$_2$Cl$_2$ and then washed with brine. The organic phase was dried over Na$_2$SO$_4$ and evaporated the solvent and purified by chromatography (Hexane:EtOAc=3:1→2:1→1:1) to give S10 as a white foamy solid (1.86 g, 88%). R$_f$: 0.55 (Hexane:EtOAc=1:1). $^1$H NMR (600 MHz, CDCl$_3$): δ 7.38-7.25 (m, 15H), 7.00 (d, J=9.1 Hz, 2H), 6.81 (d, J=9.1 Hz, 2H), 5.10-5.05 (m, 2H), 5.00-4.98 (m, 2H), 4.94-4.91 (m, 2H), 4.85-4.82 (m, 2H), 4.78 (d, J=11.6 Hz, 1H), 4.72 (d, J=11.6 Hz, 2H), 4.64 (d, J=8.2 Hz, 1H), 4.49 (d, J=12.0 Hz, 1H), 4.39 (d, J=7.9 Hz, 1H), 4.37 (dd, J=12.5, 4.3 Hz, 1H), 4.23 (dd, J=12.0, 2.0 Hz, 1H), 4.01 (dd, J=12.0, 2.2 Hz, 1H), 3.95 (t, J=9.2 Hz, 1H), 3.90 (dd, J=12.0, 4.6 Hz, 1H), 3.78 (s, 3H), 3,78-3.62 (m, 6H), 3.46-3.44 (m, 1H), 3.19-3.16 (m, 1H), 2.08 (s, 3H), 2.02 (s, 3H), 2.00 (s, 3H), 1.99 (s, 3H), 1.98 (s, 3H), 1.97 (s, 3H), 1.95 (s, 3H). $^{13}$C NMR (150 MHz, CDCl$_3$): δ 170.71 170.46, 170.42, 170.01, 169.68, 169.53, 169.22, 155.53, 151.64, 139.42, 138.34, 138.01, 128.79, 128.48, 128.38, 128.35, 128.26, 128.20, 127.86, 127.40, 127.13, 118.70, 114.71, 102.91, 101.04, 100.15, 82.77, 81.60, 76.39, 75.20, 74.92, 74.89, 73.85, 73.11, 72.67, 72.37, 72.09, 71.65, 67.99, 67.93, 61.98, 61.70, 55.85, 20.93, 20.88, 20.75.HRMS (ESI) Calcd for C$_{60}$H$_{70}$O$_{24}$Na$^+$: 1197.4149 [M+Na]$^+$; found: 1197.4142.

para-Methoxyphenyl 2,3,4,6-tetra-O-acetyl-β-D-glucopyranosyl-(1→4)-2,3,6-tri-O-acetyl-β-D-glucopyranosyl-(1→4)-2,3,6-tri-O-acetyl-β-D-glucopyranoside (S11): A suspension of S10 (1.01 g, 0.86 mmol), catalytic amount of Pd(OH)$_2$ in MeOH/EA (1/1, 10 mL) was stirred under H$_2$ balloon for 12 h. After filtration through Celite, the filter cake was washed with MeOH. The filtrate was evaporated and the residue underwent to next step without purification.

The residue described above was dissolved in pyridine (5 mL) and acetic anhydride (5 mL). The mixture was stirred at room temperature overnight. The solution was added MeOH to destroy the excess acetic anhydride and then concentrated in vacuo. CH$_2$Cl$_2$ was added and the reaction mixture was washed with 1M aqueous HCl, saturated aqueous NaHCO$_3$ and brine. The organic phase was dried over Na$_2$SO$_4$ concentrated and purified by chromatography (Hexane:EtOAc=1:1) to give S11 as a white foamy solid (794 mg, 90% in two steps). R$_f$: 0.24 (Hexane:EtOAc=1:1). $^1$H NMR (600 MHz, CDCl$_3$): δ 6.88 (d, J=9.0 Hz, 2H), 6.76 (d, J=9.0 Hz, 2H), 5.19 (t, J=9.2 Hz, 1H), 5.11-5.07 (m, 3H), 5.02 (t, J=9.7 Hz, 1H), 4.88-4.81 (m, 4H), 4.50 (dd, J=12.0, 2.0 Hz, 1H), 4.46 (d, J=8.0 Hz, 1H), 4.44 (d, J=8.0 Hz, 1H), 4.37 (dd, J=12.0, 2.0 Hz, 1H), 4.32 (dd, J=12.5, 4.3 Hz, 1H), 4.10-4.06 (m, 2H), 4.00 (dd, J=12.5, 2.0 Hz, 1H), 3.80 (t, J=9.5 Hz, 1H), 3.73 (t, J=9.5 Hz, 1H), 3.72 (s, 3H), 3.67-3.64 (m, 1H), 3.61-3.55 (m, 2H), 2.11 (s, 3H), 2.07 (s, 3H), 2.05 (s, 3H), 2.02 (s, 3H), 2.00 (s, 3H), 1.99 (s, 3H), 1.97 (2s, 6H), 1.96 (s, 3H), 1.94 (s, 3H). $^{13}$C NMR (150 MHz, CDCl$_3$): δ 170.53, 170.27, 170.23, 169.79, 169.57, 169.32, 169.10, 155.77, 150.88, 118.69, 114.53, 100.80, 100.57, 100.07, 76.44, 76.13, 72.89, 72.81, 72.77, 72.65, 72.41, 72.02, 71.75, 71.55, 71.52, 67.70, 62.15, 61.49, 55.67, 20.86, 20.80, 20.70, 20.57, 20.50. HRMS (ESI) Calcd for C$_{45}$H$_{58}$O$_{27}$Na$^+$: 1053.3058 [M+Na]$^+$; found: 1053.3051.

5-Azidopentyl 2,3,4,6-tetra-O-acetyl-β-D-glucopyranosyl-(1→4)-2,3,6-tri-O-acetyl-β-D-glucopyranosyl-(1→4)-2,3,6-tri-O-acetyl-β-D-glucopyranoside (S12): Compound S11 (866 mg, 0.84 mmol) was dissolved in acetone-H$_2$O (20 mL 3:1), and the mixture was cooled (ice-water bath). A solution of CAN (2.3 g, 4.20 mmol) in acetone/H$_2$O (10 mL 3:1) was added, and the mixture was stirred at room temperature for 30 min. The mixture was concentrated to a volume of 10 mL, diluted with $CH_2Cl_2$, washed with saturated aqueous $NaHCO_3$, dried ($Na_2SO_4$), filtered, and concentrated. The residue was then dissolved in $CH_2Cl_2$, and treated with trichloroacetonitrile (1.0 mL) and $Cs_2CO_3$ (250 mg, 0.77 mmol). After stirring at room temperature for 12 h, the reaction was washed with water, brine, dried ($Na_2SO_4$), filtered, and concentrated. A suspension of the tricholoroacetimidate compound, 5-azido-1-pentanol (0.54 g, 4.20 mmol), and 3 Å molecular sieves (1.5 g) in $CH_2Cl_2$ (10 mL) was stirred at room temperature for 1 h. The reaction mixture was cooled to 0° C. and treated dropwise with $BF_3.Et_2O$ (0.11 mL, 0.84 mmol). After stirring at 0° C. for 2 h, saturated aqueous $NaHCO_3$ was added and the reaction mixture was filtered with Celite. The mixture was diluted with $CH_2Cl_2$ and then washed with brine. The organic phase was dried over $Na_2SO_4$ and evaporated the solvent and purified by chromatography (Hexane:EtOAc=3:1→2:1→1:1) to give S12 as a white foamy solid (210 mg, 24% in three steps). $R_f$: 0.31 (Hexane: EtOAc=1:1). $^1H$ NMR (600 MHz, $CDCl_3$): δ 5.12-5.05 (m, 3H), 5.00 (t, J=9.7 Hz, 1H), 4.87-4.79 (m, 3H), 4.48 (dd, J=11.8, 2.0 Hz, 1H), 4.43 (d, J=7.9 Hz, 1H), 4.42 (d, J=7.9 Hz, 1H), 4.38 (d, J=8.0 Hz, 1H), 4.35 (dd, J=12.0, 2.0 Hz, 1H), 4.31 (dd, J=12.5, 4.3 Hz, 1H), 4.07 (dd, J=12.1, 5.2 Hz, 1H), 3.99 (dd, J=12.5, 2.0 Hz, 1H), 3.80-3.74 (m, 1H), 3.71 (dt, J=10.0, 9.5 Hz, 2H), 3.60-3.58 (m, 2H), 3.55-3.52 (m, 2H), 3.45-3.40 (m, 1H), 3.21 (t, J=6.8 Hz, 2H), 2.09 (s, 3H), 2.08 (s, 3H), 2.04 (s, 3H), 1.99 (s, 3H), 1.98 (s, 3H), 1.97 (s, 3H), 1.96 (s, 3H), 1.95 (s, 3H), 1.94 (2xs, 6H), 1.60-1.52 (m, 4H), 1.42-1.33 (m, 2H). $^{13}C$ NMR (150 MHz, $CDCl_3$): δ 170.52, 170.31, 170.21, 169.82, 169.79, 169.54, 169.31, 169.10, 100.79, 100.59, 100.55, 76.49, 76.14, 72.87, 72.67, 72.41, 71.75, 71.62, 71.53, 67.72, 62.14, 61.72, 61.48, 51.34, 28.91, 28.50, 23.12, 20.87, 20.68, 20.55, 20.48. HRMS (ESI) Calcd for $C_{43}H_{61}N_3O_{26}Na^+$: 1058.3436 $[M+Na]^+$; found: 1058.3419.

[(4,4,5,5,6,6,7,7,8,8,9,9,10,10,11,11,12,12,12-nonadecafluorododecoxycarbonyl-amino)pentyl] 2,3,4,6-tetra-O-acetyl-β-D-glucopyranosyl-(1→4)-2,3,6-tri-O-acetyl-β-D-glucopyranosyl-(1→4)-2,3,6-tri-O-acetyl-β-D-glucopyranoside (S13): Compound S13 was prepared from compound S12 according to the procedure as described for S8 in 55% yields (two steps) after column chromatography (Hexane:EtOAc=1:1→2:3). White solid. $R_f$: 0.41 (Hexane: EtOAc=1:1). $^1H$ NMR (600 MHz, $CDCl_3$): δ 5.13-5.06 (m, 3H), 5.01 (t, J=9.7 Hz, 1H), 4.88-4.81 (m, 4H), 4.79 (br, 1H), 4.50 (dd, J=11.8, 1.3 Hz, 1H), 4.44 (d, J=7.2 Hz, 1H), 4.43 (d, J=7.6 Hz, 1H), 4.38 (d, J=8.1 Hz, 1H), 4.36 (dd, J=12.0, 1.8 Hz, 1H), 4.32 (dd, J=12.5, 4.3 Hz, 1H), 410-4.06 (m, 3H), 4.02 (dd, J=12.0, 4.8 Hz, 1H), 3.99 (dd, J=12.4, 2.0 Hz, 1H), 3.79-3.74 (m, 1H), 3.72 (dt, J=11.5, 9.6 Hz, 2H), 3.63-3.58 (m, 1H), 3.56-3.50 (m, 2H), 3.43-3.40 (m, 1H), 3.11 (m, 1H), 2.20-2.10 (m, 2H), 2.10 (s, 3H), 2.09 (s, 3H), 2.05 (s, 3H), 1.99 (s, 3H), 1.98 (2xs, 6H), 1.97 (s, 3H), 1.96 (s, 3H), 1.94 (2xs, 6H), 1.91-1.86 (m, 2H), 1.54-1.52 (m, 2H), 1.48-1.43 (m, 2H), 1.34-1.26 (m, 2H). $^{13}C$ NMR (150 MHz, $CDCl_3$): δ 170.53, 170.35, 170.22, 169.81, 169.58, 169.32, 169.11, 153.25, 120.2-108.01 (m, C—F coupling unresolved), 100.79, 100.58, 100.55, 76.47, 76.14, 72.88, 72.70, 72.66, 72.39, 72.00, 71.75, 71.63, 71.54, 71.34, 69.76, 67.69, 63.67, 63.18, 62.13, 61.65, 61.48, 40.84, 29.50, 28.93, 27.99, 27.84, 27.70, 23.02, 20.89, 20.76, 20.67, 20.54, 20.48, 20.34. HRMS (ESI) Calcd for $C_{55}H_{68}F_{17}NO_{28}Na^+$: 1536.3656 $[M+Na]^+$; found: 1536.3548

[(4,4,5,5,6,6,7,7,8,8,9,9,10,10,11,11,12,12,12-nonadecafluorododecoxycarbonyl-amino)pentyl] β-D-glucopyranosyl-(1→4)-β-D-glucopyranosyl-(1→4)-β-D-gluco- pyranoside (9): Compound 9 was prepared from compound S13 according to the procedure as described for 8 in 50% yields after purification by column chromatography (EtOAc: MeOH=3:1→1:1) and FluoroFlash® SPE cartridge. White solid. $R_f$: 0.66 (EtOAc:MeOH=3:1). $^1H$ NMR (600 MHz, MeOD): δ 4.44 (d, J=8.0 Hz, 1H), 4.39 (d, J=7.8 Hz, 1H), 4.27 (d, J=7.9 Hz, 1H), 4.10 (t, J=6.1 Hz, 1H), 3.91-3.84 (m, 6H), 3.67-3.63 (m, 3H), 3.58-3.48 (m, 7H), 3.39-3.32 (m, 3H), 3.30 (m, 1H), 3.22 (m, 2H), 3.09 (t, J=6.9 Hz, 1H), 2.31-2.26 (m, 2H), 1.97-1.90 (m, 2H), 1.65-1.61 (m, 2H), 1.52-1.48 (m, 2H), 1.43-1.37 (m, 2H). $^{13}C$ NMR (150 MHz, MeOD): δ 157.71, 120.11-108.43 (m, C—F coupling unresolved), 103.44, 103.21, 103.05, 79.40, 79.00, 76.95, 76.66, 75.47, 75.25, 75.02, 73.75, 73.48, 70.19, 69.56, 63.07, 61.26, 60.58, 60.30, 40.50, 29.45, 29.20, 27.61, 27.46, 27.32, 23.10, 20.32. HRMS (ESI) Calcd for $C_{35}H_{48}F_{17}NO_{18}Na^+$: 1116.2492 $[M+Na]^+$; found: 1116.2520.

[(4,4,5,5,6,6,7,7,8,8,9,9,10,10,11,11,12,12,12-nonadecafluorododecoxycarbonyl-amino)pentyl] β-D-glucopyranosyl-(1→4)-β-D-glucopyranosyl-(1→4)-β-D-glucopyranosyl-(1→4)-β-D-glucopyranoside (10): Compound 10 was prepared from according to the procedure as described for 9 in 86% yields after purification by column chromatography. δ 4.47 (d, J=8.0 Hz, 1H), 4.46 (d, J=8.0 Hz, 1H), 4.42 (d, J=7.8 Hz, 1H), 4.30 (d, J=7.9 Hz, 1H), 4.10 (t, J=6.1 Hz, 2H), 3.91-3.89 (m, 9H), 3.68-3.63 (m, 3H), 3.60-3.50 (m, 14H), 3.39-3.25 (m, 14H), 3.12 (t, J=6.9 Hz, 2H), 2.33-2.26 (m, 2H), 1.96-1.90 (m, 2H), 1.70-1.61 (m, 2H), 1.55-1.52 (m, 2H), 1.43-1.37 (m, 2H). HRMS (ESI) Calcd for $C_{41}H_{58}F_{17}NO_{23}Na^+$: 1255.3128 $[M+Na]^+$; found: 1255.3225.

Mass Spectrometry

The immobilized slide was analyzed with a Bruker Ultraflex MALDI-TOF mass spectrometer equipped with a nitrogen pulsed laser (355 nm). Each data point was collected at the average of 500-1000 shots of the laser beam, and the laser fluence was applied at 40-95%, with the best results obtained mostly at 50-80%. A standard aqueous solution of mannose-$NH_2$ was manually deposited on a defined area of the ACG slide and used to calibrate the data obtained from the immobilized sugars on the same slide substrate. For quantitative comparison of the grafted mannose derivatives at different concentrations, all analyses were made at a single measurement of 500 shots at 80% fluence. The variation in average peak intensity with S/N ratio was plotted.

Protein-Binding Assay

Mannose-protein-binding assay of immobilized mannose with biotinylated ConA and Cy3-tagged streptavidin. The same slide used for MS analysis was washed again with distilled water under mild sonication and then rinsed with PBS (phosphate-buffered saline) buffer. Biotin-labeled ConA (Invitrogen C 21420) was diluted 500-1000 times in PBST buffer (PBS with 0.05% Tween 20). The protein solution (50 mL) was applied to each array substrate and incubated in a Whatman 16-pad incubation chamber. These slides were wrapped with foil and incubated for 1 h in a shaker at room temperature. After the incubation, the slides were washed three times with PBST buffer. Streptavidin-Cy3 (Sigma S 6402) was diluted in PBS buffer 100 times, and the slides were covered with aluminum foil and incubated again with streptavidin-Cy3 for another hour. After the second incubation, the slides were washed with PBST buffer and distilled water and then purge-dried with high-quality nitrogen gas. The array pattern was analyzed in reflective mode with 540-nm laser light by using the fluorescence light scanner, Array- WoRx, made by Applied Precision. The best block on each slide was selected for statistical fluorescence-intensity analysis.

Globo H-protein-binding assay of immobilized Globo H with monoclonal antibody VKg (IgG) from mouse and Cy3-tagged secondary antibody. The Globo H microarray slides were blocked with aqueous ethanolamine (50 mM) to remove the unreacted NHS on the slide surface. The slides were assembled again in the reaction cell and washed with PBS buffer (pH 7.4). Next, a solution of VK9 (1 mL, 50 µg/mL in each cell), the anti-Globo H monoclonal antibody (IgG) from mouse, in PBST (pH 7.4) was added to the cell. The binding experiment was conducted with constant shaking for 1 h. The slide was washed three times (with 10 minutes constant swirling each time) with PBST buffer (pH 7.4). Cy3-tagged goat anti-mouse IgG for VK9 was added to the cell, and the mixture was incubated with shaking in the dark for 1 h. The protein-bound slides were washed five times each with PBST buffer (pH 7.4), PBS buffer (pH 7.4), and water and then purge-dried with nitrogen gas.

MS-TOF Analysis and Glycan Array Preparation of 4-MS-TOF Analysis of the Poly-Fluorinated Mannose Adsorbed on the PTFE-Like ACG Slides Compound 4 was dissolved in methanol/water (6/4) solvent mixture at approximately 10 mM, 1 mM, 100 uM in series. The solutions (1 µL each) were spotted manually, and also, microarrayed on the slides with the BioDot AD3200 instrument (Agilent Technology) by robotic pin (Array It, SMP4), a deposition of approximately 1.1 nL of the solution per spots of the array. The slides were stored in 30% humidity chamber overnight then analyzed by mass spectroscopy. The blank and poly-fluorinated mannose slides, which contain both silane based and phosphonic acis based ACG slides, were analyzed with Bruker Ultraflex MALDI-TOF mass spectrometer equipped with a nitrogen pulsed laser (355 nm). Equal volume of BSA Trypsin digested (1 pmoel/µL) solution was mixed homogeneously with DHB (dihydroxybenzoic acid, 10 mg in 1:1 acetonitrile/water) solution, and was used as the standard for MS-TOF mass calibration. Each data point was collected at the average of 500 shots of the laser beam, and the laser fluence between 2 to 20% was applied. Most of the experiments were carried out under positive polarized electrical field.

Figure 26A:
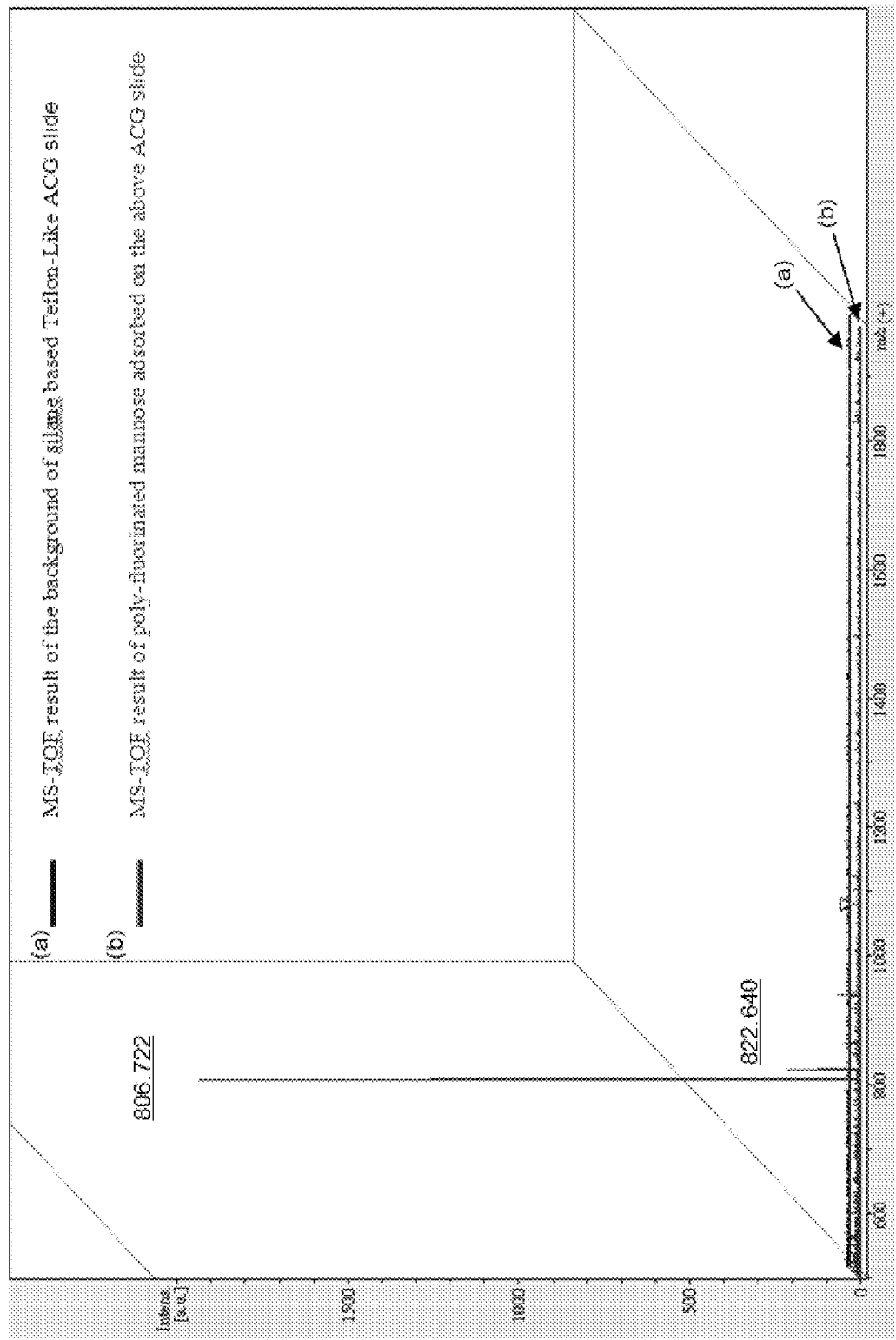
FIG. 26 are graphs of implementations of experimental data characterizing silane-based PTFE-like ACG slide by MS-TOF and protein-sugar binding.
Figure 27A:
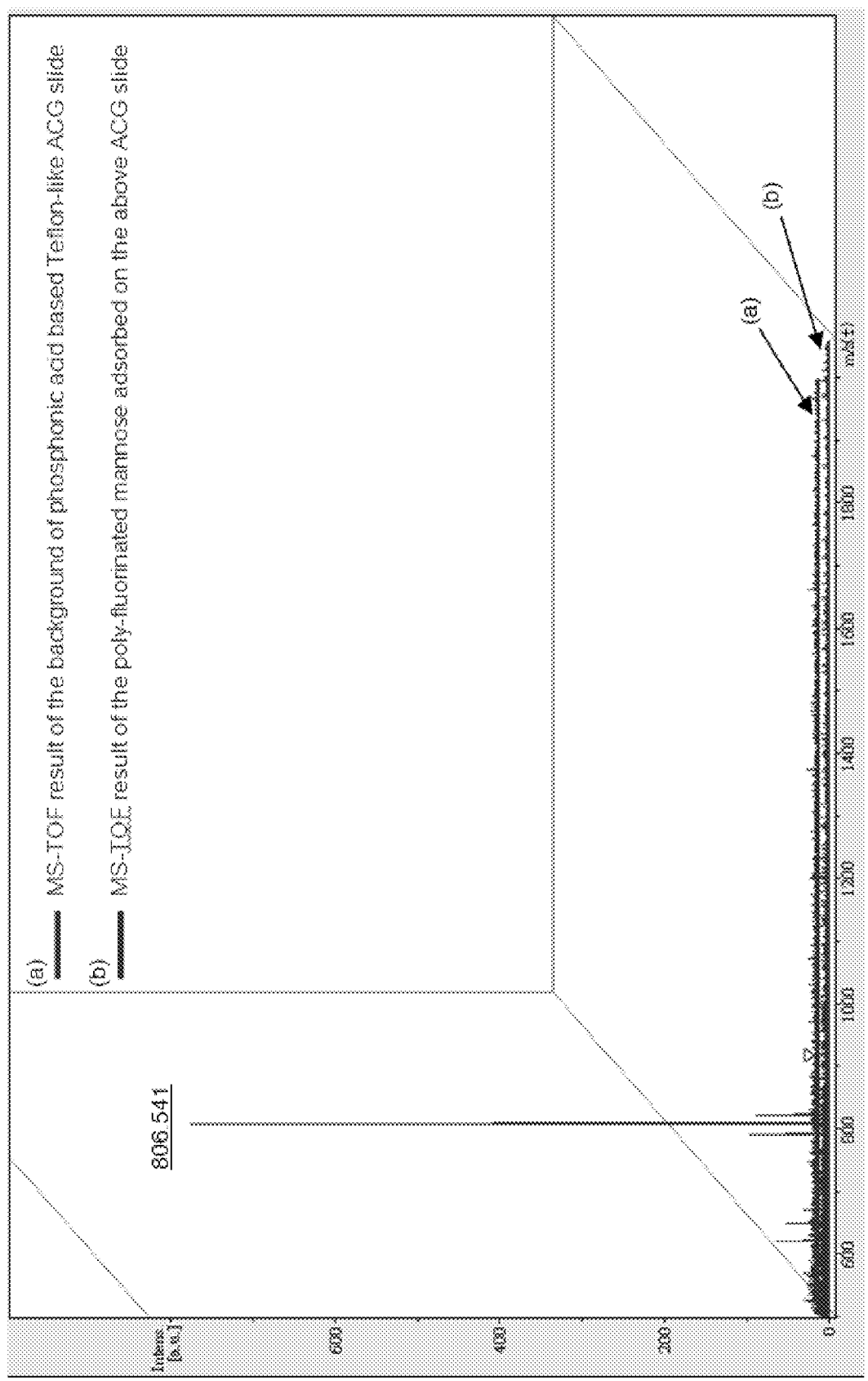
FIG. 27 are graphs of implementations of experimental data characterizing phosphonic acid-based PTFE-like ACG slides by MS-TOF and protein-sugar binding.
Figure 28:
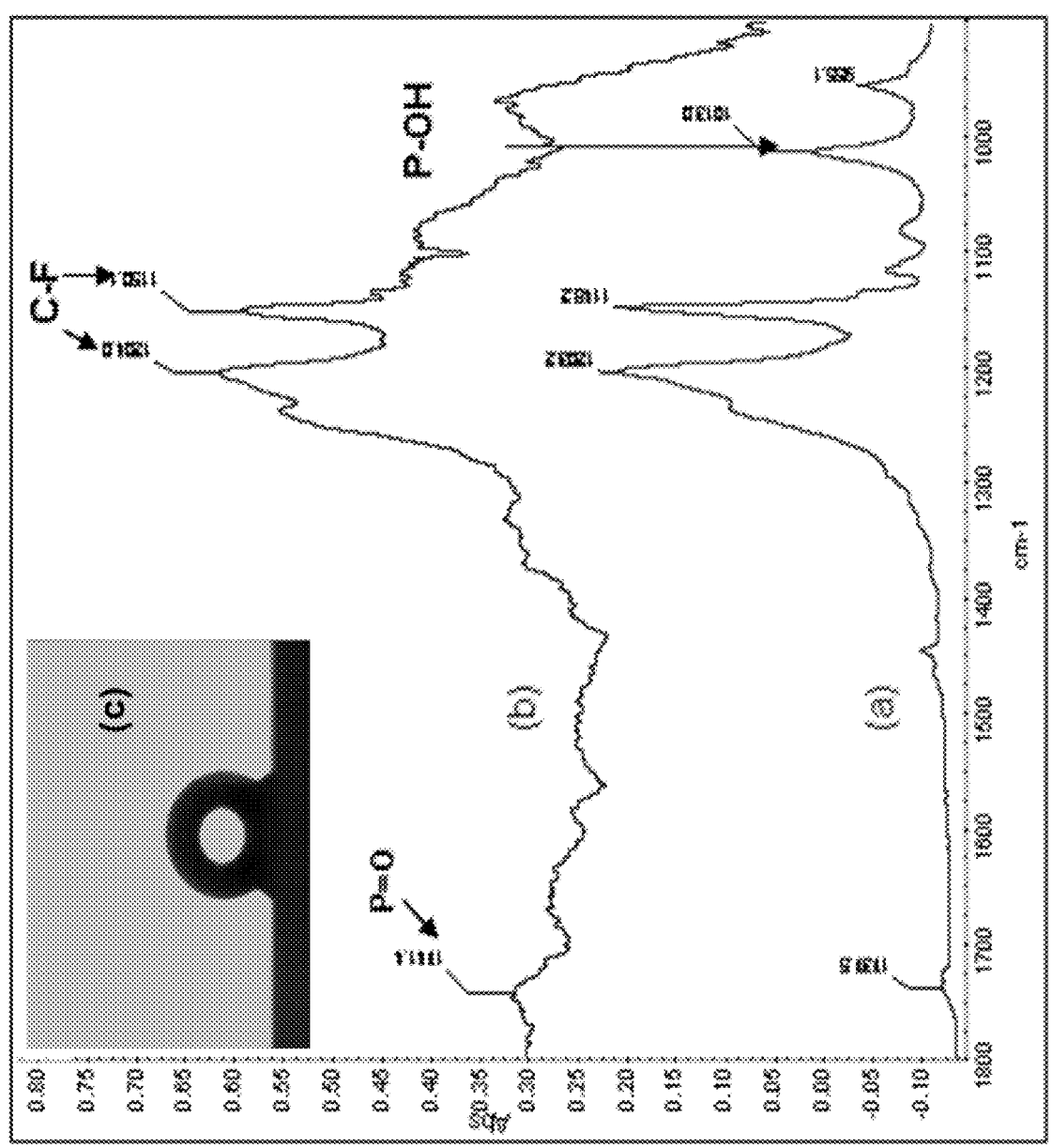
FIG. 28 are graphs of implementations of experimental an FTIR spectrum of Pure Compound 3 (HDFDPA, 3,3,4,4,5,5,6,6,7,7,8,8,-9,9,10,10,10-heptadecafluorodecylphosphonic acid) and an FTIR spectrum of ACG surface grafted compound 3.

FIG. 26A and FIG. 27A show the MS-TOF background results of these newly fabricated PTFE-like ACG slides. In FIG. 26A, (a) represents an MS-TOF result of the background of silane based PTFE-Like ACG; (b) represents an MS-TOF result of poly-fluorinated mannose adsorbed on the above ACG slide. In FIG. 27A, (a) represents an MS-TOF result of the background of phosphonic acid based PTFE-Like ACG and (b) represents MS-TOF result of poly-fluorinated mannose adsorbed on the above ACG slide. Molecular ions of mannose derivatives (Mw. 783) were observed at 806 $[M+Na]^+$, and 822 $[M+K]^+$ with very clean baseline since organic chemicals do not adhere to the PTFE-like ACG slide surface.

Figure 26B:
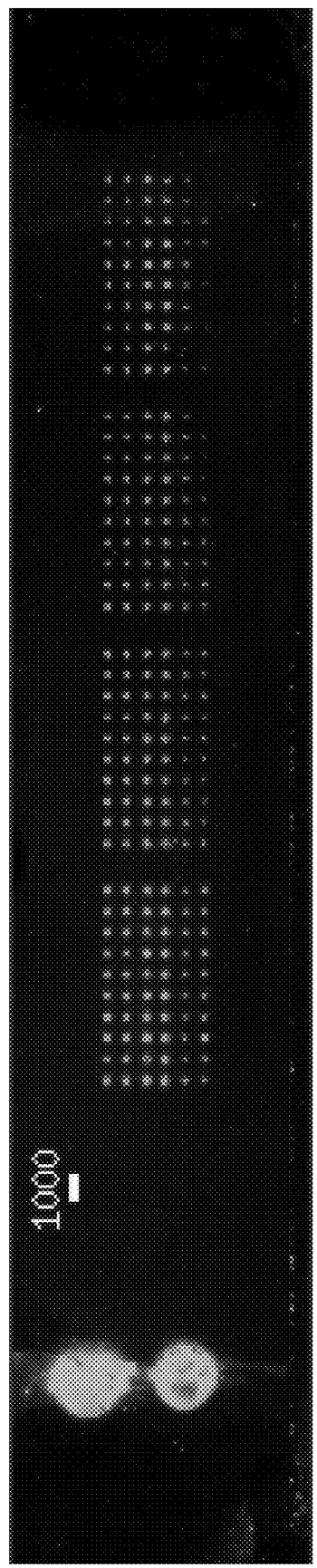
Figure 27B:
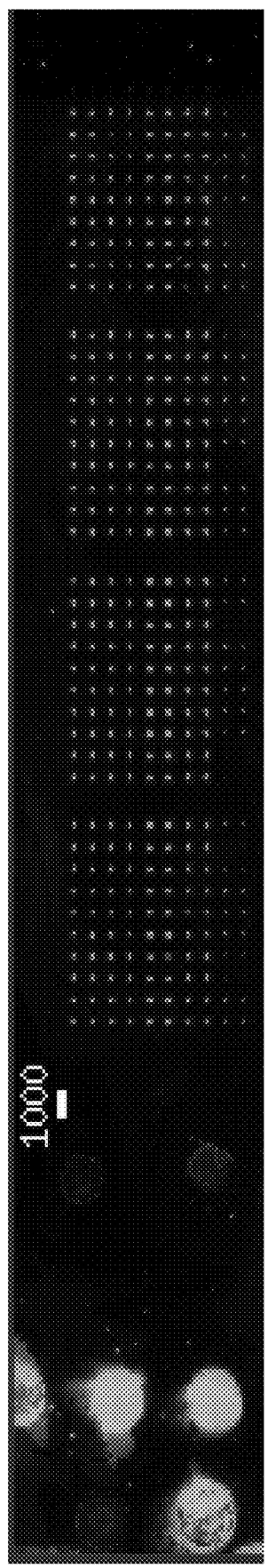

FIG. 26B and FIG. 27B give the results of poly-fluorinated mannose silane based and phosphonic acid based slides. FIG. 26B represents implementations of a microarray of silane based PTFE-like ACG slide. The mannose solutions (1.1 µL/spot) varied in concentration (from 12 mM, 1.2 mM, to 120 µM). Similarly, 27B shows a microarray of a phosphonic acid based PTFE-like ACG slide. The mannose solutions (1.1 µL/spot) varied in concentration (from 14 mM, 1.4 mM, to 140 µM). The fluorescence-tagged Con A-Mannose binding where the mannose derivatives were micro arrayed on the PTFE-like ACG Slide.

Fluorescence-tagged Con A/Mannose Binding of the Poly-Fluorinated Mannose Adsorbed on the PTFE-Like ACG Slides.

100 µL of Alex 488-tagged Concanavalin A in phosphate-BSA buffer (25 µg/mL, pH 6.5) was applied on the ACG slide surface immobilized with mannose derivative. These slides with Con A solution were incubated at room temperature for approximately 2 hours. After incubation, the slides were washed three times each with 12 ml of Phosphate-BSA buffer, PBST buffer, and de-ionized water in petri dishes with gentle swirling. Then nitrogen purge dried and analyzed by Array WoRx (Applied Precision) in reflective mode of the fluorescence light scanner at 530 nm. FIG. S1(c) and FIG. S2(c) show the results of these bioassay.

On-Chip Analysis by MALDI-TOF (Ultra-Flex II) (Reaction in Eppendorf)

Cellulase was prepared (5 U/mL in 25 mM pH 5.05 NaOAc buffer solution). Substrate was also dissolved in NaOAc buffer solution (25 mM, pH 5.05) to give 0.5 mM substrate solution. Add 100 uL cellulase solution to 100 uL substrate solution in eppendorf to have a 2.5U/mL cellulase solution with 0.25mM substrate. This solution was incubated in 37° C. for 18 hours. Add 100 µL incubated solution onto the slide loaded in FAST® Frame. Put the slide in dry box to remove the water, and then use high vacuum to remove trace water. 100 µL water was used to rinse each well of the FAST® Frame multi-slide plate to solve and remove the salt of the buffer solution. Remove any residual water on the plate by high vacuum and then analyzed the slide by MALDI-TOF Ultra-Flex II.

On-Chip Analysis by MALDI-TOF (Ultra-Flex II) (Reaction on Chip Directly)

Cellulase was prepared (5 U/mL in 25 mM pH 5.05 NaOAc buffer solution). Substrate was also dissolved in NaOAc buffer solution (25 mM, pH 5.05) to give 0.5 mM substrate solution. Add 50 µL cellulase solution to 50 µL substrate solution onto the glass slide which was loaded in FAST® Frame multi-slide plate to have a 2.5 U/mL cellulase solution with 0.25 mM substrate. The well of the plate was sealed and the whole assembly was incubated in 37° C. for 18 hours. Put the slide in dry box to remove the water, and then use high vacuum to remove trace water. 100 uL water was used to rinse each well of the FAST® Frame multi-slide plate to solve and remove the salt of the buffer solution. Remove any residual water on the plate by high vacuum and then analyzed the slide by MALDI-TOF Ultra-Flex II.

Cellulase Purification and MS-TOF Analysis of Cellulase Acitivity, Cloning, Expression and Purification of Exoglucanase and Endoglucanase The genomic DNA of *Sulfolobus solfataricus* (ATCC 35092) and *Clostridium thermocellum* (ATCC 27405) were obtained from the ATCC biological resource center. The Sso7d (NCBI accession number: AAK42090) gene fragment was amplified directly from the *Sulfolobus solfataricus* genome by polymerase chain reaction (PCR) with forward 5' GGAATFCCATATGGCAACAGTAAAGTFCAAG 3' (SEQ ID NO: 1) and reverse 5' CG GGATCCCTTCTTTTGCTTCTCTAACATTTG 3' (SEQ ID NO: 2) primers. The PCR product encoding Sso7d was digested with NdeI and BamHI and subsequently cloned into expression vector pET-28a (Novagen) to generate pET-28-Sso7d. A two sticky-ends linker, generated by denaturing and annealing with 5' GATCTGATCTGTACGACGATGAC-GATAAGGGATCTATCGAAGGTCGTG 3' (SEQ ID NO: 3) and 5' GATCCACGACCTFCGATAGATCCCT-FATCGTCATCGTCGTACAGATCA 3' (SEQ ID NO: 4) primers, was inserted into the BamHI cleaved pET-28-Sso7d to generate pET-28-Sso7d-Fxa. The functional domains of CtCbhA (NCBI accession number: X80993) gene fragment was amplified directly from the *Clostridium thermocellum* genome by polymerase chain reaction (PCR) with forward 5' GAAGATCTATACTFCCGCAGCCTGATG 3' (SEQ ID NO: 5) and reverse 5' ACGCGTCGACTTAGGTTTCACTGTCTGTGTACTG 3' (SEQ ID NO: 6) primers. The PCR product encoding CtCbhA was digested with BglII and SalI and subsequently cloned into BamHI and SalI cleaved pET-28-Sso7d-Fxa to generate pET-28-Sso7d-Fxa-CtCbhA. The functional domains of CtCel44A (NCBI accession number: D83704) gene fragment was amplified directly from the *Clostridium thermocellum* genome by polymerase chain reaction (PCR) with forward 5' GAAGATCTGAACCTGCAAAAGTGGTFGAC 3' (SEQ ID NO: 7) and reverse 5' ACGCGTCGACTTAGGGCTCCGCAGCTFCAAGCAC 3' (SEQ ID NO: 8) primers.

The PCR product encoding CtCel44A was digested with BglII and SalI and subsequently cloned into BamHI and SalI cleaved pET-28-Sso7d-Fxa to generate pET-28-Sso7d-Fxa-CtCel44A. All DNA constructs were verified by nucleotide sequencing. The correct constructs were transformed into *Escherichia coli* strain BL21 (DE3) competent cell for protein expression. The 10 ml overnight culture of a single transformant was used to inoculate 1 liter of fresh LB medium containing 30 µg/ml kanamycin at 30° C. The incubated temperature was changed to 16° C. until the cells were grown to $A_{600\ nm}$=0.8~1. One hour later isopropyl β-thiogalactopyranoside (IPTG) was added to a final concentration of 0.5 mM. After 16 h, the cells were harvested by centrifugation at 7,000×g for 15 min to collect the cell paste. The cell pellet was resuspended immediately in the lysis buffer containing 20 mM Tris-HCl, 400 mM NaCl, 10 mM imidazole, pH 7.5. The cell suspension was disrupted by Constant Cell Disruption System (CONSTANT SYSTEM Ltd., UK) and centrifuged at 17,000×g to remove cell debris. The cell-free extract was loaded onto a $Ni^{2+}$-NTA column, which had been previously equilibrated with lysis buffer. The column was washed with lysis buffer, subsequently the His6-tagged protein was eluted by a linear gradient from 10 mM to 300 mM imidazole. The purified $His_6$-tagged Sso7d fusion CtCbhA and CtCel44A proteins were concentrated and changed to stored buffer (50 mM Tris-HCl, 100 mM NaCl, pH 8.0) by 30 kDa cut-off size membrane of Amicon-Ultra-15 (Millipore, Mass., USA) for storage at −80° C.

According to implementations, the devices and methods (e.g., mass spectroscopy) of the present disclosure are operational in an environment comprising numerous general purpose or special purpose computing systems or configurations. Examples of well known computing systems, environments, or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, telephony systems, distributed computing environments that include any of the above systems or devices, and the like.

The devices and methods of the present disclosure may be described in the general context of computer-executable instructions, such as program modules, being executed by a computer. Generally, program modules include routines, programs, objects, components, data structures, etc., that perform particular tasks or implement particular abstract data types. The system may also be practiced in distributed computing environments where tasks are performed by remote processing devices that are linked through a communications network. In a distributed computing environment, program modules may be located in both local and remote computer storage media including memory storage devices. The computer programs are stored in a memory medium or storage medium or they may be provided to a processing unit through a network or I/O bus.

In one aspect, the devices and methods of the present disclosure include at least one central processing unit (CPU) or processor. The CPU can be coupled to a memory, ROM or computer readable media containing the computer-executable instructions. Computer readable media can be any available media that can be accessed by the system and includes both volatile and nonvolatile media, removable and non-removable media implemented in any method or technology for storage of information such as computer readable instructions, data structures, program modules or other data. Computer storage media includes, but is not limited to, RAM, ROM, EEPROM, flash memory, portable memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the fingerprint generation and matching systems. Communication media typically embodies computer readable instructions, data structures, program modules or other data in a modulated data signal such as a carrier wave or other transport mechanism and includes any information delivery media. By way of example, and not limitation, communication media includes wired media such as a wired network or direct-wired connection, and wireless media such as acoustic, RF, infrared and other wireless media. Combinations of any of the above should also be included within the scope of computer readable media. The computer readable media may store instructions or data which implement all or part of the system described herein.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. An array of carbohydrates immobilized on an aluminum-coated non-transparent solid substrate or a polyfluorinated aluminum-coated non-transparent solid substrate, the array comprising:
   a plurality of carbohydrates immobilized at discrete locations on a surface of the aluminum-coated non-transparent solid substrate, such that
   (a) the immobilized carbohydrates, which are polyfluorinated with a —CnF2n+1 (n>=4) tail, can be characterized by mass spectroscopy (MS) without addition of a miscible organic matrix, and
   (b) analysis of binding reactions between the immobilized carbohydrates and molecules suspected of specifically binding the carbohydrates can be performed, comprising detecting a fluorescent signal coupled to the molecules, and wherein the intensity of a fluorescent signal generated on the surface of the aluminum-coated solid substrate is detectable with higher sensitivity than on the surface of a transparent solid substrate
   wherein the substrate is conductive or semiconductive of an electrical field,
   wherein aluminum is coated on a first transparent solid substrate at a thickness greater than 100 nm to render the first transparent solid substrate into an aluminum coated non-transparent solid substrate, and
   wherein the surface of the aluminum-coated solid substrate is anodized to form a porous aluminum oxide layer of thickness less than 5 nm.

2. The array of claim 1, wherein the first transparent solid substrate is glass.

3. The array of claim 1, wherein the carbohydrate is a glycan.

4. The array of claim 1, wherein the carbohydrates are immobilized by a non-covalent bond.

5. The array of claim 4, wherein the polyfluorinated carbohydrates are spotted on the surface of the aluminum-coated non-transparent solid substrate.

6. The array of claim 1, wherein the carbohydrates are immobilized by a covalent bond.

7. The array of claim 6, wherein the carbohydrates are modified with a phosphonic acid functional group.

8. The array of claim 6, wherein the phosphonylated carbohydrates are immobilized on the surface of the substrate by a covalent bond between the phosphonic acid group and the aluminum oxide on the surface of the aluminum-coated non-transparent solid substrate.

9. The array of claim 6, wherein the carbohydrates are modified with a photocleavable linker and a silane functional group.

10. The array of claim 9, wherein the photocleavable linker has the general formula:

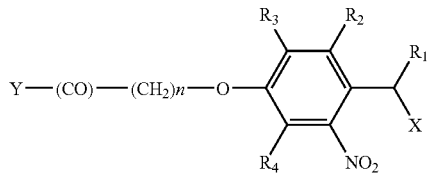

in which $R^1$ is hydrogen, $C_1$-$C_8$ alkyl; $R^2$ and $R^4$ are each independently hydrogen, $C_1$-$C_8$ alkoxy; $R^3$ is $C_1$-$C_8$ alkoxy; X is O(CO)N—(CH$_2$)n-$R^5$, in which n>=3, $R^5$ is carbohydrates, Y is the aluminum coated solid support.

11. The array of claim 1, wherein the mass spectroscopic characterization of the immobilized carbohydrates comprises a time-of-flight mass spectrometry (MS-TOF).

12. The array of claim 11, wherein the mass spectroscopic characterization of the immobilized carbohydrates comprises a matrix-assisted laser desorption-ionization time-of-flight (MALDI-TOF) mass spectrometry.

13. The array of claim 11, wherein the carbohydrates are polysaccharides, or oligosaccharides, or carbohydrate portions of a glycoconjugate, or cellobiose, or cellotriose, or cellotetraose, or GloboH, or Gb5.

14. The array of claim 13, wherein the mass spectroscopic characterization of the immobilized carbohydrates comprises: characterization of carbohydrate products of a cellulase enzyme reaction.

15. The array of claim 14, wherein the cellulase enzyme reaction is performed on immobilized carbohydrates on the array surface, wherein the cellulase enzyme is suspected of being capable of degrading the immobilized polysaccharides, or oligosaccharides, or carbohydrate portions of a glycoconjugate, or cellobiose, or cellotriose, or cellotetraose, or GloboH, or Gb5.

16. The array of claim 11, wherein a carbohydrate binding assay can be performed on the array about 15 minutes following an MS-TOF characterization.

17. The array of claim 1, wherein the molecules suspected of specifically binding the carbohydrates are proteins.

18. The array of claim 17, wherein the proteins are cellulases.

19. The array of claim 18 wherein the cellulases are selected from the group consisting of 1,4-β-glucosidases, exoglucanases (1,4-β-D glucan cellobiohydrolases) and endoglucanases (1,4-β-D glucan glucanohydrolases).

20. The array of claim 17, wherein the proteins analyzed for binding to the carbohydrates immobilized on the array are labeled with a detectable label.

21. The array of claim 20, wherein the protein labels comprise fluorescent dyes.

22. The array of claim 21, wherein the fluorescent dyes comprise amine-reactive dyes.

23. An array of carbohydrates immobilized on an aluminum-coated non-transparent solid substrate or a polyfluorinated aluminum-coated non-transparent solid substrate for use in disease diagnosis and drug discovery, wherein the array is fabricated by a method comprising:
  (a) providing a first transparent solid surface;
  (b) coating the first transparent solid substrate with aluminum at a thickness of greater than 100 nm to render the first transparent solid substrate into an aluminum coated non-transparent solid substrate;
  (c) anodizing the surface of the aluminum-coated solid substrate to form a porous aluminum oxide layer of thickness less than 5 nm;
  (d) optionally polyfluorinating the surface of the aluminum-coated solid substrate; and
  (e) immobilizing a plurality of carbohydrates at discrete locations on the surface of the aluminum coated non-transparent solid substrate or a polyfluorinated aluminum-coated non-transparent solid substrate semitransparent or non-transparent solid substrate,
  wherein the substrate is conductive or semiconductive of an electrical field end of wherein the immobilized carbohydrates can be characterized by mass spectroscopy (HS) without addition of a miscible organic matrix.

24. The array of claim 1, wherein the aluminum oxide layer on the surface of the aluminum-coated solid substrate is activated for covalently binding the carbohydrates.

\* \* \* \* \*